United States Patent
Fredricks et al.

(10) Patent No.: US 7,625,704 B2
(45) Date of Patent: Dec. 1, 2009

(54) METHODS AND COMPOSITIONS FOR IDENTIFYING BACTERIA ASSOCIATED WITH BACTERIA VAGINOSIS

(75) Inventors: David N. Fredricks, Seattle, WA (US); Tina Fiedler, Auburn, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 240 days.

(21) Appl. No.: 11/607,639

(22) Filed: Dec. 1, 2006

(65) Prior Publication Data

US 2007/0178495 A1   Aug. 2, 2007

Related U.S. Application Data

(63) Continuation-in-part of application No. 11/514,382, filed on Aug. 31, 2006, now abandoned.

(60) Provisional application No. 60/713,049, filed on Aug. 31, 2005.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/22.1; 536/24.3

(58) Field of Classification Search .............. 435/6, 435/91.2; 536/22.1, 24.3
See application file for complete search history.

(56) References Cited

U.S. PATENT DOCUMENTS 5,213,961 A * 5/1993 Bunn et al. ................ 435/6
2006/0062774 A1  3/2006 Davis et al.
2006/0172330 A1  8/2006 Osborn et al.
2007/0178495 A1 * 8/2007 Fredricks et al. ............. 435/6

OTHER PUBLICATIONS

Doyle et al. Journal of Industrial Microbiology, 1995, vol. 15, p. 67-70.*
Hayashi et al. Microbiol. Immunol. 2002. vol. 46(8), p. 535-548.*
The attached alignment search report. (Not For Printing).*
The nucleic acid sequence search reports for SEQ ID NOs 64 and 108 (Not For Printing).*
Buck et al. BioTechniques, 1999, vol. 27(3), p. 528-536.*
Fredricks et al. "Changes in Vaginal Bacterial Concentrations with Intravaginal Metronidazole Therapy for Bacterial Vaginosis as Assessed by Quantitative PCR" *Journal of Clinical Microbiology* 47(3):721-726 (2009).
Fredricks et al. "Molecular Identification of Bacteria Associated with Bacterial Vaginosis" *The New England Journal of Medicine* 353(18):1899-1911 (2005).
Fredricks et al. "Molecular Methodology in Determining Vaginal Flora in Health and Disease: Its Time Has Come" *Current Infectious Disease Reports* 7:463-470 (2005).
Fredricks et al. "Targeted PCR for Detection of Vaginal Bacteria Associated With Bacterial Vaginosis" *Journal of Clinical Microbiology* 45(10):3270-3276 (2007).
Hill et al. "Characterization of Vaginal Microflora of Healthy, Non-pregnant Women by *Chaperonin-60* Sequence-Based Methods" *American Journal of Obstetrics and Gynecology* 193:682-692 (2005).
Zhou et al. "Characterization of Vaginal Microbial Communities in Adult Healthy Women Using Cultivation-Independent Methods" *Microbiology* 150:2565-2573 (2004).

* cited by examiner

*Primary Examiner*—Kenneth R. Horlick
*Assistant Examiner*—Joyce Tung
(74) *Attorney, Agent, or Firm*—Myers Bigel Sibley & Sajovec, P.A.

(57) ABSTRACT

The present invention provides methods and compositions for identifying bacteria associated with bacterial vaginosis and diagnosing bacterial vaginosis in a subject.

3 Claims, 6 Drawing Sheets

FIGURES 2A & B
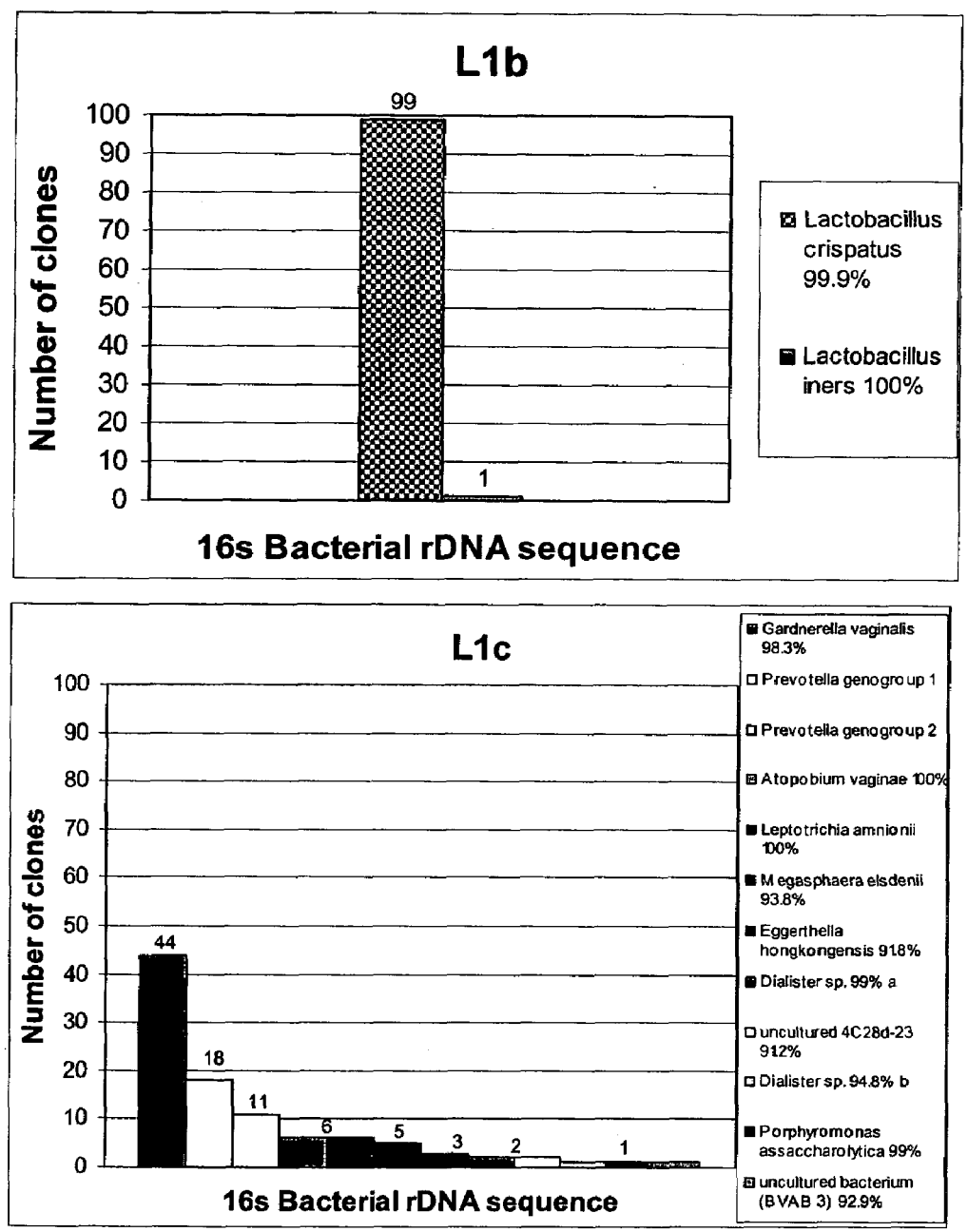

FIGURES 2C & D
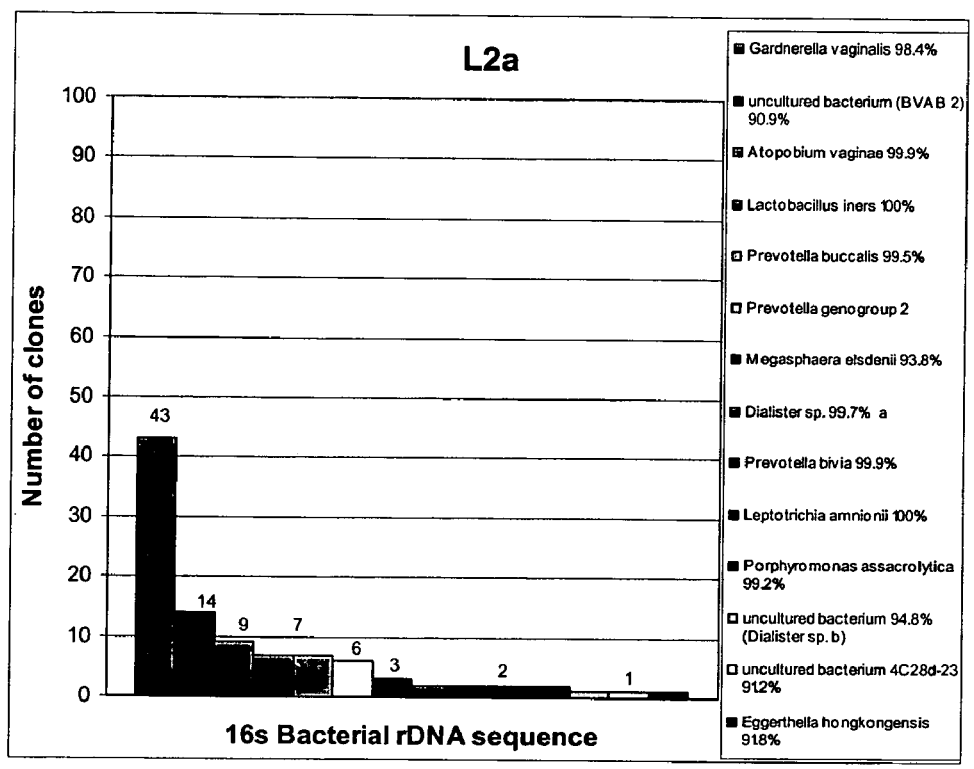
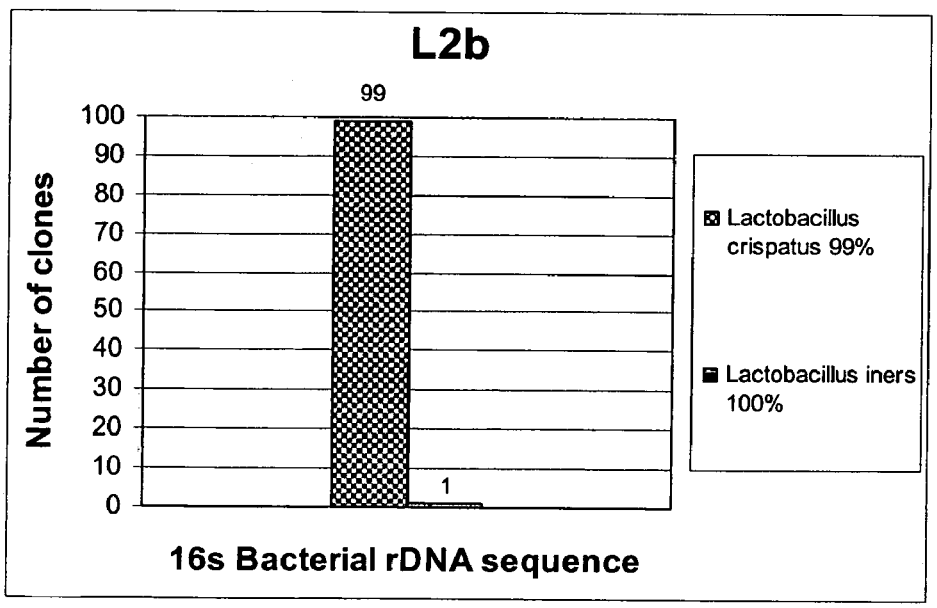

FIGURES 2E & F
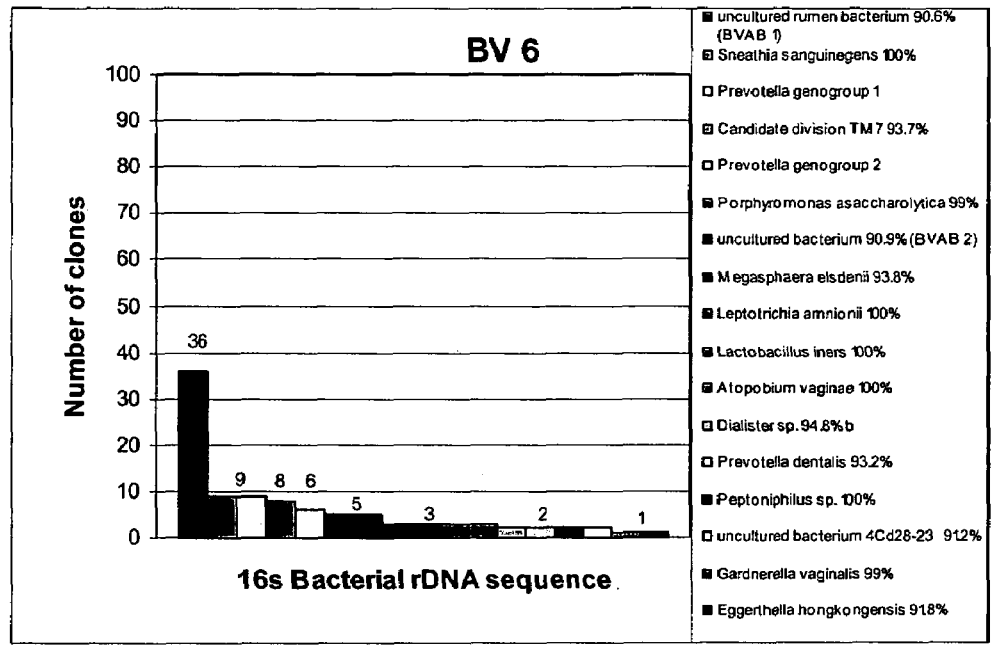
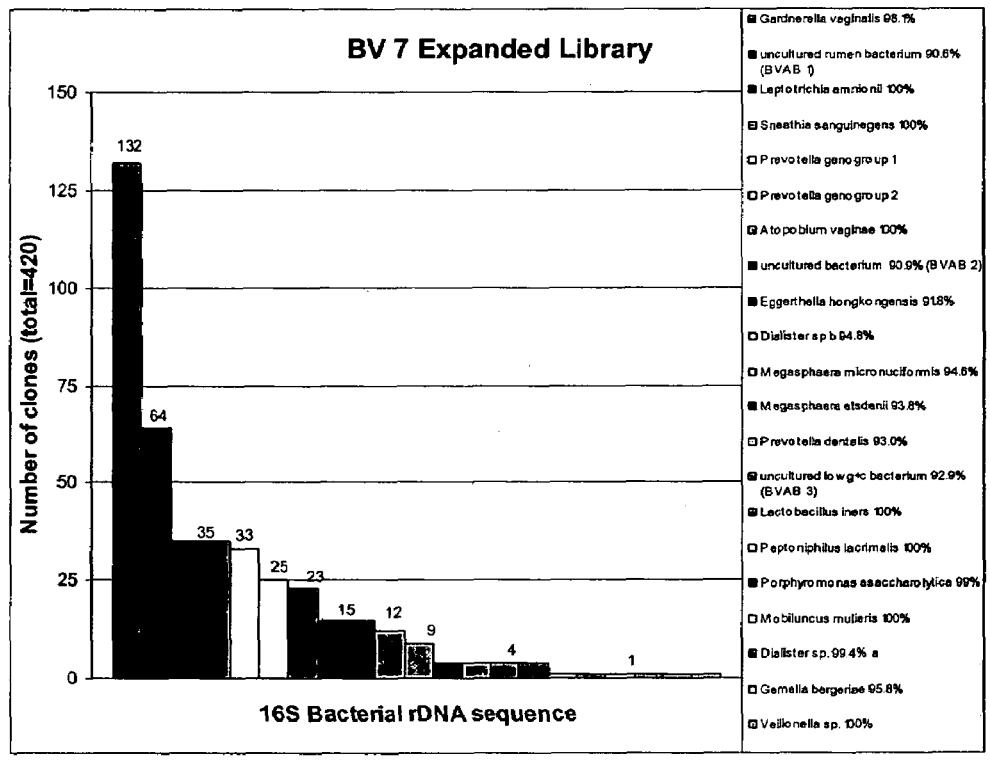

METHODS AND COMPOSITIONS FOR IDENTIFYING BACTERIA ASSOCIATED WITH BACTERIA VAGINOSIS

STATEMENT OF PRIORITY

This application is a continuation-in-part application of U.S. application Ser. No. 11/514,382, filed Aug. 31, 2006 now abandoned, which claims the benefit, under 35 U.S.C. § 119 (e), of U.S. Provisional Application No. 60/713,049, filed Aug. 31, 2005, the entire contents of each of which are incorporated by reference herein.

STATEMENT OF GOVERNMENT SUPPORT

Studies described herein were supported by National Institute of Allergy and Infectious Diseases grants R03 AI053250 and R01AI052228. The United States Government has certain rights in this invention.

FIELD OF THE INVENTION

The present invention is directed to compositions and methods of their use in the identification of bacteria associated with bacterial vaginosis.

BACKGROUND OF THE INVENTION

Bacterial vaginosis (BV) is a common condition, affecting millions of women annually[1], and is associated with numerous health problems including pre-term labor and low birth weight[2,3], pelvic inflammatory disease[4,5], and acquisition of human immunodeficiency virus[6,7]. Malodorous vaginal discharge may be the only symptom of BV, and many affected individuals are asymptomatic[8].

Studies using cultivation methods have demonstrated that women with BV experience loss of vaginal lactobacilli and concomitant overgrowth of anaerobic and facultative bacteria. Several bacteria have been implicated in BV, such as *Gardnerella vaginalis*[9] and *Mobiluncus curtisii*[10], but these species are also found in subjects without BV, and thus are not specific markers for disease[11]. For this reason, bacterial cultivation of vaginal fluid has not proven useful for the diagnosis of BV. Rather, clinical criteria or Gram stain analysis of vaginal fluid are employed for diagnosis. At least 3 of 4 elements must be present to fulfill Amsel clinical criteria for BV[12], including presence of (1) thin, homogeneous, milky, vaginal discharge; (2) vaginal fluid pH greater than 4.5; (3) positive whiff test—production of fishy odor when 10% potassium hydroxide is added to a slide containing vaginal fluid; and (4) presence of clue cells (>20% of epithelial cells with adherent bacteria) on microscopic examination of vaginal fluid[12]. An alternative diagnostic approach employs Gram stain of vaginal fluid (Nugent score)[13] to distinguish normal vaginal flora (Gram-positive rods, lactobacilli) from BV flora (Gram-negative *morphotypes*)[14].

Koch's postulates for establishing disease causation have not been fulfilled for any bacterium or group of bacteria associated with BV. BV responds to treatment with antibiotics such as metronidazole or clindamycin, but metronidazole has poor in vitro activity against *G. vaginalis* and *M. curtisii*. Relapse and persistence are common[11]. Thus, the etiology and pathogenesis of BV remain poorly understood, and management can be challenging.

Only a fraction of the bacteria present in most microbial ecosystems are amenable to propagation in the laboratory[15]. Bacteria in complex microbial communities can be identified by characterizing their ribosomal RNA genes (rDNA), an approach that has the advantage of detecting fastidious or cultivation-resistant organisms[16]. The present invention describes the identification of bacteria present in vaginal fluid samples using an approach employing molecular methods.

The present invention overcomes previous shortcomings in the diagnosis and treatment of bacterial vaginosis by providing compositions and methods of their use in identifying bacteria associated with bacterial vaginosis.

SUMMARY OF THE INVENTION

The present invention provides an isolated nucleic acid comprising, consisting essentially of and/or consisting of a nucleotide sequence selected from the group consisting of a nucleotide sequence identified as GenBank accession number AY738656 (SEQ ID NO:48), AY738657 (SEQ ID NO:49), AY738658 (SEQ ID NO:50), AY738659 (SEQ ID NO:51), AY738660 (SEQ ID NO:52), AY738661 (SEQ ID NO:53), AY738662 (SEQ ID NO:54), AY738663 (SEQ ID NO:55), AY738664 (SEQ ID NO:56), AY738665 (SEQ ID NO:57), AY738666 (SEQ ID NO:58), AY738667 (SEQ ID NO:59), AY738668 (SEQ ID NO:60), AY738669 (SEQ ID NO:61), AY738670 (SEQ ID NO:62), AY738671 (SEQ ID NO:63), AY738672 (SEQ ID NO:64), AY738673 (SEQ ID NO:65), AY738674 (SEQ ID NO:66), AY738675 (SEQ ID NO:67), AY738676 (SEQ ID NO:68), AY738677 (SEQ ID NO:69), AY738678 (SEQ ID NO:70), AY738679 (SEQ ID NO:71), AY738680 (SEQ ID NO:72), AY738681 (SEQ ID NO:73), AY738682 (SEQ ID NO:74), AY738683 (SEQ ID NO:75), AY738684 (SEQ ID NO:76), AY738685 (SEQ ID NO:77), AY738686 (SEQ ID NO:78), AY738687 (SEQ ID NO:79), AY738688 (SEQ ID NO:80), AY738689 (SEQ ID NO:81), AY738690 (SEQ ID NO:82), AY738691 (SEQ ID NO:83), AY738692 (SEQ ID NO:84), AY738693 (SEQ ID NO:85), AY738694 (SEQ ID NO:86), AY738695 (SEQ ID NO:87), AY738696 (SEQ ID NO:88), AY738697 (SEQ ID NO:89), AY738698 (SEQ ID NO:90), AY738699 (SEQ ID NO:91), AY738700 (SEQ ID NO:92), AY738701 (SEQ ID NO:93), AY738702 (SEQ ID NO:94), AY738703 (SEQ ID NO:95), AY738704 (SEQ ID NO:96), AY738705 (SEQ ID NO:97), AY738706 (SEQ ID NO:98), AY724739 (SEQ ID NO:99), AY724740 (SEQ ID NO:100), AY724741 (SEQ ID NO:1021, AY724742 (SEQ ID NO:102), bankit643633 (SEQ ID NO:103), bankit655126 (SEQ ID NO:104) and bankit655138 (SEQ ID NO:105) (Table 5). Further provided herein is a composition comprising one or more of the nucleic acids of this invention, in any combination.

Also provided herein is a bacterium, which can be isolated and/or in a population, which is a thin curved rod, comprising a ribosomal DNA comprising the nucleotide sequence of GenBank Accession No. bankit643633 (SEQ ID NO:103, bacterial vaginosis associated bacterium 1; BVAB1).

In addition, the present invention provides a bacterium, which can be isolated and/or in a population, which is a short wide rod, comprising a ribosomal DNA comprising the nucleotide sequence of GenBank Accession No. bankit655126 (SEQ ID NO:104, bacterial vaginosis associated bacterium 2; BVAB 2).

Furthermore the present invention provides a bacterium, which can be isolated and/or in a population, which is a long lancet-shaped rod, comprising a ribosomal DNA comprising the nucleotide sequence of GenBank Accession No. bankit655138 (SEQ ID NO:105, bacterial vaginosis associated bacterium 3; BVAB 3).

In additional embodiments, the present invention provides a method of detecting BVAB1 in a sample, comprising: a)

contacting the sample with a first oligonucleotide primer comprising the nucleotide-sequence of primer BVAB1-1019F (Uncxb1-649F, SEQ ID NO:3, forward primer) and a second oligonucleotide primer comprising the nucleotide sequence of primer BVAB1-1280R (Uncxb1-908R, SEQ ID NO:4, reverse primer) under conditions whereby amplification of nucleic acid in the sample can occur; and b) detecting amplification of nucleic acid specific for BVAB 1, thereby detecting BVAB 1 in the sample.

Additionally provided is a method of detecting BVAB 2 in a sample, comprising: a) contacting the sample with a first oligonucleotide primer comprising the nucleotide sequence of primer BVAB2-619F (Uncxb2-619F, SEQ ID NO:5, forward primer) and a second oligonucleotide primer comprising the nucleotide sequence of primer BVAB2-1024R (Uncxb2-1023R, SEQ ID NO:6, reverse primer) under conditions whereby amplification of nucleic acid in the sample can occur; and b) detecting amplification of nucleic acid specific for BVAB 2, thereby detecting BVAB 2 in the sample.

A method is also provided herein of detecting BVAB 3 in a sample, comprising: a) contacting the sample with a first oligonucleotide primer comprising the nucleotide sequence of primer BVAB3-999F (Uncxb3-1000F, SEQ ID NO:7, forward primer) and a second oligonucleotide primer comprising the nucleotide sequence of primer BVAB3-1278R (Uncxb3-1278R, SEQ ID NO:8 reverse primer) under conditions whereby amplification of nucleic acid in the sample can occur; and b) detecting amplification of nucleic acid specific for BVAB 3, thereby detecting BVAB 3 in the sample.

The present invention further provides a method of detecting BVAB1 in a sample, comprising: a) contacting the sample with a nucleic acid comprising the nucleotide sequence of Uncxb1-134-F1 (SEQ ID NO:42) under conditions whereby nucleic acid hybridization can occur; and b) detecting nucleic acid hybridization, thereby detecting BVAB 1 in the sample.

Also provided herein is a method of detecting BVAB 2 in a sample, comprising: a) contacting the sample with a nucleic acid comprising the nucleotide sequence of Uncxb2-1244-Cy3 (SEQ ID NO:43) under conditions whereby nucleic acid hybridization can occur; and b) detecting nucleic acid hybridization, thereby detecting BVAB 2 in the sample.

Further provided herein is a method of detecting BVAB 3 in a sample, comprising: a) contacting the sample with a nucleic acid comprising the nucleotide sequence of Uncxb3-1244-Cy3 (SEQ ID NO:44) under conditions whereby nucleic acid hybridization can occur; and b) detecting nucleic acid hybridization, thereby detecting BVAB 3 in the sample.

In further embodiments, the present invention provides a method of diagnosing bacterial vaginosis in a subject, comprising: 1) contacting a gynecological sample from the subject with one or more oligonucleotide primer pairs comprising, consisting essentially of and or consisting of nucleotide sequences selected from the group consisting of:
a) BVAB1-1019F/BVAB1-1280R (SEQ ID NOS:3 and 4, detects BVAB 1);
b) BVAB2-619F/BVAB2-1024R (SEQ ID NOS:5 and 6, detects BVAB-2);
c) BVAB3-999F/BVAB3-1278R (SEQ ID NOS:7 and 8, detects BVAB 3);
d) G.vag 644F/G.vag 851R (SEQ ID NOS:9 and 10, detects *Gardnerella Vaginalis*);
e) Ato-442F/Ato-1017R (SEQ ID NOS:11 and 12, detects *Atopobium* sp.);
f) Egger-621F/Egger-859R (SEQ ID NOS:13 and 14, detects *Eggerthella* sp.);
g) Lepto-395F/Lepto-646R (SEQ ID NOS:15 and 16, detects *Leptotrichia* sp.);
h) MegaE-456F/MegaE-667R (SEQ ID NOS:19 and 20, detects *Megasphaera* Type I);
i) MegaM-453F/MegaM-666R (SEQ ID NOS:17 and 18, detects *Megasphaera* Type II);
j) TM7-641F/TM7-1020R (SEQ ID NOS:21 and 22, detects BVAB-TM7);
k) P.lacri-999F/Pepton-1184R (SEQ ID NOS:23 and 24, detects *Peptoniphilus Lacrimalis*);
l) Pepton-1003F/Pepton-1184R (SEQ ID NOS:25 and 24, detects *Peptoniphilus Sp.*);
m) M.curt-44OF/M.curt-1026R (SEQ ID NOS:26 and 27, detects *Mobiluncus Curtisii*);
n) Mobil-577F/M.mulie-1026R (SEQ ID NOS:28 and 29, detects *Mobiluncus Mulieris*);
o) PrevG1-468F/PrevG1-857R (SEQ ID NOS:30 and 31, detects *Prevotella* G1);
p) PrevG2-648F/PrevG2-871R (SEQ ID NOS:32 and 33, detects *Prevotella* G2);
q) L.crisp-452F/L.crisp-1023R (SEQ ID NOS:34 and 35, detects *Lactobacillus crispatus*);
r) L.iners-453F/L.iners-1022R (SEQ ID NOS:36 and 37, detects *Lactobacillus iners*); and
s) any combination of (a)-(r), under conditions whereby amplification of nucleic acid in the sample can occur; and 2) detecting amplification of nucleic acid specific for one or more bacteria selected from the group consisting-of:
i) BVAB 1;
ii) BVAB 2:
iii) BVAB 3:
iv) *Gardnerella vaginalis;*
v) *Atopobium* sp.;
vi) *Eggerthella* sp.;
vii) *Leptotrichia* sp.;
viii) *Megasphaera* Type I;
ix) *Megasphaera* Type II;
x) BVAB-TM7;
xi) *Peptoniphilus lacrimalis;*
xii) *Peptoniphilus*sp.;
xiii) *Mobiluncus curtisii;*
xiv) *Mobiluncus mulieris;*
xv) *Prevotella* G1;
xvi) *Prevotella* G2;
xvii) *Lactobacillus crispatus;*
xviii) *Lactobacillus iners;* and
xix) any combination of (i)-(xvii), thereby diagnosing bacterial vaginosis in the subject.

An additional aspect of this invention is a method of detecting BVAB2 and/or *Megasphaera* in a sample, comprising: a) contacting the sample with a first primer pair specific for nucleic acid comprising the nucleotide sequence of SEQ ID NO:104 (BVAB2) and a second primer pair specific for a nucleic acid comprising the nucleotide sequence of SEQ ID NO:64 (*Megasphaera*) under conditions whereby nucleic acid amplification can occur; and b) detecting amplification of nucleic acid of (a), thereby detecting BVAB2 and/or *Megasphaera* in the sample. In some embodiments of this method, the first primer pair can comprise the nucleotide sequence of forward primer Uncxb2-619F (SEQ ID NO:5) and the nucleotide sequence of reverse primer Uncxb2-1023R (SEQ ID NO:6) and the second primer can comprise the nucleotide sequence of forward primer MegaE-458F (SEQ ID NO:19) and the nucleotide sequence of reverse primer MegaE-666R (SEQ ID NO:20).

A further aspect of the present invention is a method of detecting BVAB2 and/or *Megasphaera* in a sample, comprising: a) contacting the sample with a first probe that hybridizes with a nucleic acid comprising the nucleotide sequence of SEQ ID NO:104 (BVAB2) and a second probe that hybridizes with a nucleic acid comprising the nucleotide sequence of SEQ ID NO:64 (*Megasphaera*) under conditions whereby nucleic acid hybridization can occur; and b) detecting nucleic acid hybridization of the first probe and/or second probe, thereby detecting BVAB2 and/or *Megasphaera* in the sample. In some embodiments of this method, the first probe can comprise the nucleotide sequence of SEQ ID NO:44 (Uncxb2-1244-Cy3) and the second probe can comprise the nucleotide sequence of SEQ ID NO:108 (Mega_485-506).

Also provided herein is a method of detecting BVAB1 in a sample, comprising: a) contacting the sample with a probe that hybridizes with a nucleic acid comprising the nucleotide sequence of SEQ ID NO:103 under conditions whereby nucleic acid hybridization can occur; and b) detecting nucleic acid hybridization, thereby detecting BVAB1 in the sample. In some embodiments of this method, the probe can comprise the nucleotide sequence of SEQ ID NO:43 (Uncxb1-134-F1).

Further provided herein is a method of detecting BVAB2 in a sample, comprising: a) contacting the sample with a probe that hybridizes with a nucleic acid comprising the nucleotide sequence of SEQ ID NO:104 under conditions whereby nucleic acid hybridization can occur; and b) detecting nucleic acid hybridization, thereby detecting BVAB2 in the sample. In some embodiments of this method, the probe can comprise the nucleotide sequence of SEQ ID NO:44 (Uncxb2-1244-Cy3).

In additional embodiments, the present invention provides a method of detecting BVAB3 in a sample, comprising: a) contacting the sample with a probe that hybridizes with a nucleic acid comprising the nucleotide sequence of SEQ ID NO:105 under conditions whereby nucleic acid hybridization can occur; and b) detecting nucleic acid hybridization, thereby detecting BVAB3 in the sample. In some embodiments of this method, the probe can comprise the nucleotide sequence of SEQ ID NO:45 (Uncxb3-1244-Cy3).

Further provided is a method of detecting BVAB1 in a sample, comprising: a) contacting the sample with a primer pair specific for a nucleic acid comprising the nucleotide sequence of SEQ ID NO:103 under conditions whereby amplification of nucleic acid in the sample can occur; and b) detecting amplification of nucleic acid specific for BVAB1, thereby detecting BVAB1 in the sample. In some embodiments of this method, the primer pair can comprise a forward primer comprising the nucleotide sequence of SEQ ID NO:3 (Uncxb1-649F) and a reverse primer comprising the nucleotide sequence of SEQ ID NO:4 (Uncxb1-908R).

A further aspect of this invention is a method of detecting BVAB2 in a sample, comprising: a) contacting the sample with a primer pair specific for a nucleic acid comprising the nucleotide sequence of SEQ ID NO:104 under conditions whereby amplification of nucleic acid in the sample can occur; and b) detecting amplification of nucleic acid specific for BVAB2, thereby detecting BVAB2 in the sample. In some embodiments of this invention, the primer pair can comprise a forward primer comprising the nucleotide sequence of SEQ ID NO:5 (Uncxb2-619F) and a reverse primer comprising the nucleotide sequence of SEQ ID NO:6 (Uncxb2-1023R).

Also provided herein is a method of detecting BVAB3 in a sample, comprising: a) contacting the sample with a primer pair specific for a nucleic acid comprising the nucleotide sequence of SEQ ID NO:105 under conditions whereby amplification of nucleic acid in the sample can occur; and b) detecting amplification of nucleic acid specific for BVAB3, thereby detecting BVAB3 in the sample. In some embodiments of this invention, the primer pair can comprise a forward primer comprising the nucleotide sequence of SEQ ID NO:7 (Uncxb3-1000F) and a reverse primer comprising the nucleotide sequence of SEQ ID NO:8 (Uncxb3-1278R).

A further embodiment of the invention is a method of diagnosing bacterial vaginosis in a subject, comprising: A) contacting a gynecological sample from the subject with one or more primer pairs selected from the group consisting of: a) a primer pair specific for a nucleic acid comprising the nucleotide sequence of SEQ ID NO:103 (BVAB1); b) a primer pair specific for a nucleic acid comprising the nucleotide sequence of SEQ ID NO:104 (BVAB2); c) a primer pair specific for a nucleic acid comprising the nucleotide sequence of SEQ ID NO:105 (BVAB3); d) a primer pair specific for a nucleic acid comprising the nucleotide sequence of SEQ ID NO:57, SEQ ID NO:58, SEQ ID NO:59, SEQ ID NO:60 and/or SEQ ID NO:87 (*Gardnerella vaginalis*); e) a primer pair specific for a nucleic acid comprising the nucleotide sequence of SEQ ID NO:49 and/or SEQ ID NO:50 (*Atopobium* sp.); f) a primer pair specific for a nucleic acid comprising the nucleotide sequence of SEQ ID NO:48 (*Eggerthella* sp.); g) a primer pair specific for a nucleic acid comprising the nucleotide sequence of SEQ ID NO:51 and/or SEQ ID NO:102 (*Leptotrichia* sp.; *Sneathia* sp.); h) a primer pair specific for a nucleic acid comprising the nucleotide sequence of SEQ ID NO:64 (*Megasphaera* sp.); and i) any combination of (a)-(h) above, under conditions whereby nucleic acid amplification can occur; and B) detecting amplification of nucleic acid specific for one or more of the following bacteria: a) BVAB1; b) BVAB2; c) BVAB3; d) *Gardnerella* vaginalis; e) Atopobium sp.; f) *Eggerthella* sp.; g) *Leptotrichia* sp. or *Sneathia* sp.; h) *Megasphaera* sp.; and i) any combination of (a)-(h), thereby diagnosing bacterial vaginosis in the subject. In some embodiments of this method, the primer pair of (a) can comprise a forward primer comprising the nucleotide sequence of SEQ ID NO:3 (Uncxb1-649F) and a reverse primer comprising the nucleotide sequence of SEQ ID NO:4 (Uncxb1-908R); the primer pair of (b) can comprise a forward primer comprising the nucleotide sequence of SEQ ID NO:5 (Uncxb2-619F) and a reverse primer comprising the nucleotide sequence of SEQ ID NO:6 (Uncxb2-1023R); the primer pair of (c) can comprise a forward primer comprising the nucleotide sequence of SEQ ID NO:7 (Uncxb3-1000F) and a reverse primer comprising the nucleotide sequence of SEQ ID NO:8 (Uncxb3-1278R); the primer pair of (d) can comprise a forward primer comprising the nucleotide sequence of SEQ ID NO:9 (G.vag 643F) and a reverse primer comprising the nucleotide sequence of SEQ ID NO:10 (G. vag 846R); the primer pair of (e) can comprise a forward primer comprising the nucleotide sequence of SEQ ID NO:11 (Ato-441F) and a reverse primer comprising the nucleotide sequence of SEQ ID NO:12 (Ato-1016R); the primer pair of (f) can comprise a forward primer comprising the nucleotide sequence of SEQ ID NO:13 (Egger-630F) and a reverse primer comprising the nucleotide sequence of SEQ ID NO:14 (Egger-854R); the primer pair of (g) can comprise a forward primer comprising the nucleotide sequence of SEQ ID NO:15 (Lepto-394F) and a reverse primer comprising the nucleotide sequence of SEQ ID NO:16 (Lepto-645R); and/or the primer pair of (h) can comprise a forward primer comprising the nucleotide sequence of SEQ ID NO:19 (MegaE-458F) and a reverse primer comprising the nucleotide sequence of SEQ ID NO:20 (MegaE-666R). In further embodiments of this method, the sample can be contacted with two or more primer pairs of step (A); or with three or more primer pairs of step (A) or with four or more oligonucleotide primer pairs of step (A) and nucleic acid specific for two, three, four or more of the bacteria of step (B) can be detected.

In addition, the present invention provides a method of diagnosing bacterial vaginosis in a subject, comprising: A. contacting a gynecological sample of the subject with a primer pair specific for a nucleic acid selected from the group consisting of: a) a nucleic acid comprising the nucleotide sequence of SEQ ID NO:103 (BVAB1); b) a nucleic acid comprising the nucleotide sequence of SEQ ID NO:104 (BVAB2); c) a nucleic acid comprising the nucleotide sequence of SEQ ID NO:105 (BVAB3); d) a nucleic acid comprising the nucleotide sequence of SEQ ID NO:57, SEQ ID NO:58, SEQ ID NO:59, SEQ ID NO:60 and/or SEQ ID NO:87 (*Gardnerella vaginalis*); e) a nucleic acid comprising the nucleotide sequence of SEQ ID NO:49 and/or SEQ ID NO:50 (*Atopobium* sp.); f) a nucleic acid comprising the nucleotide sequence of SEQ ID NO:48 (*Eggerthella* sp.); g) a nucleic acid comprising the nucleotide sequence of SEQ ID NO:51 and/or SEQ ID NO:102 (*Leptotrichia* sp.; *Sneathia* sp.); h) a primer pair specific for a nucleic acid comprising the nucleotide sequence of SEQ ID NO:64 (*Megasphaera* sp.); and i) any combination of (a)-(h), under conditions whereby nucleic acid amplification can occur and the amount of amplified nucleic acid can be determined; B) detecting amplification of a nucleic acid of (A) above; C) determining the amount of the amplified nucleic acid of (B); and D) comparing the amount of amplified nucleic acid of (C) with the amount of amplified nucleic acid of the same bacterial species from a gynecological sample of a control subject who does not have bacterial vaginosis, whereby an increase in the amount of nucleic acid of (C) relative to the control subject provides a diagnosis of bacterial vaginosis in the subject. In some embodiments of this method, the amount of nucleic acid of (C) can be at least 1% greater than the amount of nucleic acid of the same bacterial species from the control subject.

Further provided herein is a method of diagnosing bacterial vaginosis in a subject, comprising: A) contacting a gynecological sample of the subject with a primer pair specific for prokaryotic nucleic acid in the sample under conditions whereby nucleic acid amplification can occur and the amount of amplified nucleic acid can be quantitated to determine the total amount of bacteria in the sample; B) detecting amplification of nucleic acid in (A) and determining the amount of amplified nucleic acid and the total amount of bacteria in the sample; C) contacting the sample with a primer pair specific for a nucleic acid selected from the group consisting of: a) a nucleic acid comprising the nucleotide sequence of SEQ ID NO:103 (BVAB1); b) a nucleic acid comprising the nucleotide sequence of SEQ ID NO:104 (BVAB2); c) a nucleic acid comprising the nucleotide sequence of SEQ ID NO:105 (BVAB3); d) a nucleic acid comprising the nucleotide sequence of SEQ ID NO:57, SEQ ID NO:58, SEQ ID NO:59, SEQ ID NO:60 and/or SEQ ID NO:87 (*Gardnerella vaginalis*); e) a nucleic acid comprising the nucleotide sequence of SEQ ID NO:49 and/or SEQ ID NO:50 (*Atopobium* sp.); f) a nucleic acid comprising the nucleotide sequence of SEQ ID NO:48 (*Eggerthella* sp.); g) a nucleic acid comprising the nucleotide sequence of SEQ ID NO:51 and/or SEQ ID NO:102 (*Leptotrichia* sp.; *Sneathia* sp.); h) a nucleic acid comprising the nucleotide sequence of SEQ ID NO:64 (*Megasphaera* sp.); and i) any combination of (a)-(h), under conditions whereby nucleic acid amplification can occur and the amount of amplified nucleic acid can be determined; and D) detecting amplification of a nucleic acid of (C) above; E) determining the amount of the amplified nucleic acid of (B) and the amount of each bacterial species specific for the nucleic acid of (C); and F) calculating the percentage of each bacterial species of (E) in the total amount of bacteria in the sample, whereby the presence of any one or more than one of the bacterial species of (E) that is at least 1% of the total amount of the bacteria in the sample provides a diagnosis of bacterial vaginosis in the subject.

In additional embodiments, the present invention provides a method of determining the amount of BVAB2 and/or *Megasphaera* in a sample, comprising: a) contacting the sample with a first primer pair specific for a nucleic acid comprising the nucleotide sequence of SEQ ID NO:104 (BVAB2) and a second primer pair specific for a nucleic acid comprising the nucleotide sequence of SEQ ID NO:64 (*Megasphaera*) under conditions whereby nucleic acid amplification can occur and the amount of amplified nucleic acid can be determined and b) detecting amplification of nucleic acid of (a) and determining the amount of BVAB2 and/or *Megasphaera* nucleic acid and the amount of BVAB2 and/or *Megasphaera* in the sample.

Additionally provided is a method of determining the amount of BVAB2 in a sample as a percentage of the total amount of bacteria in the sample, comprising: a) contacting the sample with a primer pair specific for prokaryotic nucleic acid under conditions whereby nucleic acid amplification can occur and the amount of amplified nucleic acid can be determined; b) detecting amplification of nucleic acid in (a) and determining the amount of amplified nucleic acid and the total amount of bacteria in the sample; c) contacting the sample with a primer pair specific for a nucleic acid comprising the nucleotide sequence of SEQ ID NO:104 (BVAB2) under conditions whereby nucleic acid amplification can occur and the amount of amplified nucleic acid can be determined; d) detecting amplification of nucleic acid of (c) and determining the amount of nucleic acid specific for BVAB2 and the amount of BVAB2 bacteria in the sample; and e) calculating the percentage of BVAB2 bacteria in the total amount of bacteria in the sample.

Also provided herein is a method of determining the amount of *Megasphaera* in a sample as a percentage of the total amount of bacteria in the sample, comprising: a) contacting the sample with a primer pair specific for prokaryotic nucleic acid under conditions whereby nucleic acid amplification can occur and the amount of amplified nucleic acid can be determined; b) detecting amplification of nucleic acid in (a) and determining the amount of amplified nucleic acid and the total amount of bacteria in the sample; c) contacting the sample with a primer pair specific for a nucleic acid comprising the nucleotide sequence of SEQ ID NO:64 under conditions whereby nucleic acid amplification can occur and the amount of amplified nucleic acid can be determined and d) detecting amplification of nucleic acid of (c) and determining the amount of *Megasphaera* nucleic acid and the amount of *Megasphaera* bacteria in the sample; and e) calculating the percentage of *Megasphaera* bacteria in the total amount of bacteria in the sample.

Furthermore, the present invention provides a method of diagnosing bacterial vaginosis in a subject, comprising: a) contacting a gynecological sample of the subject with a primer pair specific for prokaryotic nucleic acid in the sample under conditions whereby nucleic acid amplification can occur and the amount of amplified nucleic acid can be quantitated to determine the total amount of bacteria in the sample; b) detecting amplification of nucleic acid of (a); c) determining the amount of amplified nucleic acid of (b) and the total amount of bacteria in the sample; d) contacting the sample with a first primer pair specific for nucleic acid comprising the nucleotide sequence of SEQ ID NO:104 (BVAB2) and a second primer pair specific for nucleic acid comprising the nucleotide sequence of SEQ ID NO:64 (*Megasphaera*) under conditions whereby nucleic acid amplification can occur and the amount of amplified nucleic acid can be determined; e) detecting amplification of nucleic acid of (d); f) determining the amount of amplified nucleic acid of (e) and the amount of BVAB2 and/or *Megasphaera* sp. bacteria in the sample; and g) calculating the percentage of each of the BVAB2 and/or *Megasphaera* bacteria in the total amount of bacteria in the sample, whereby the presence of an amount of BVAB2 and/or *Megasphaera* that is at least 1% of the total amount of the bacteria in the sample provides a diagnosis of bacterial vaginosis in the subject.

In addition, the present invention provides a method of diagnosing bacterial vaginosis in a subject, comprising: A) contacting a gynecological sample of the subject with a nucleic acid probe that hybridizes with nucleic acid specific for a bacterium selected from the group consisting of: a) BVAB1; b) BVAB2; c) BVAB3; d) *Mobiluncus*; e) *Gardnerella*; f) *Atopobium*; g) *Megasphaera;* and h) any combination of (a)-(g) above, under conditions whereby nucleic acid hybridization can occur; and B) detecting nucleic acid hybridization, thereby diagnosing bacterial vaginosis in the subject.

A further embodiment of this invention is a method of diagnosing bacterial vaginosis in a subject, comprising: A) contacting a gynecological sample of the subject with a nucleic acid probe that hybridizes with nucleic acid specific for a bacterium selected from the group consisting of: a) BVAB1; b) BVAB2; c) BVAB3; d) *Mobiluncus*; e) *Gardnerella*; f) *Atopobium*; g) *Megasphaera;* and h) any combination of (a)-(g) above, under conditions whereby nucleic acid hybridization can occur; and B) detecting nucleic acid hybridization, C) determining the amount of hybridized nucleic acid of (B); and D) comparing the amount of the hybridized nucleic acid of (C) with the amount of hybridized nucleic acid of the same bacterial species from a gynecological sample of a control subject who does not have bacterial vaginosis, whereby an increase in the amount of the nucleic acid of (C) relative to the control subject provides a diagnosis of bacterial vaginosis in the subject. In some embodiments of this method, the amount of nucleic acid of (C) is at least 1% greater than the amount of the nucleic acid of the same bacterial species from the control subject.

The present invention also provides a method of diagnosing bacterial vaginosis in a subject, comprising: a) contacting a gynecological sample of the subject with a first nucleic acid probe that hybridizes with nucleic acid specific for BVAB2 and a second nucleic acid probe that hybridizes with *Megasphaera*, under conditions whereby nucleic acid hybridization can occur; and b) detecting nucleic acid hybridization, thereby diagnosing bacterial vaginosis in the subject.

Further provided herein is a method of diagnosing bacterial vaginosis in a subject, comprising: A) contacting a gynecological sample of the subject with a first nucleic acid probe that hybridizes with nucleic acid specific for BVAB2 and a second nucleic acid probe that hybridizes with *Megasphaera* under conditions whereby nucleic acid hybridization can occur; and B) detecting nucleic acid hybridization, C) determining the amount of hybridized nucleic acid of BVAB2 and the amount of hybridized nucleic acid of *Megasphaera;* and D) comparing the amount of the hybridized nucleic acid of (C) with the amount of hybridized nucleic acid of BVAB2 and/or *Megasphaera* from a gynecological sample of a control subject who does not have bacterial vaginosis, whereby an increase in the amount of the nucleic acid of (C) relative to the control subject provides a diagnosis of bacterial vaginosis in the subject. In some embodiments of this method, the amount of hybridized nucleic acid of BVAB2 and/or *Megasphaera* is at least 1% greater than the amount of hybridized nucleic acid of BVAB2 and/or *Megasphaera* from the control subject.

Additionally provided herein is a method of diagnosing bacterial vaginosis in a subject, comprising: A) contacting a gynecological sample from the subject with a nucleic acid probe specific for prokaryotic nucleic acid under conditions whereby nucleic acid hybridization can occur; B) detecting nucleic acid hybridization and determining the amount of hybridized nucleic acid and the total amount of bacteria in the sample; C) contacting the sample with a nucleic acid probe specific for a bacterium selected from the group consisting of: a) BVAB1; b) BVAB2; c) BVAB3; d) *Mobiluncus*; e) *Gardnerella*; f) *Atopobium*; g) *Megasphaera;* and h) any combination of (a)-(g) above, under conditions whereby nucleic acid hybridization can occur; D) detecting nucleic acid hybridization of (C); E) determining the amount of nucleic acid hybridization of (D) and determining the amount of each bacterial species specific for the nucleic acid of (C); and F) calculating the percentage of each bacterial species of (E) in the total amount of bacteria in the sample, whereby the presence of any one or more than one of the bacterial species of (E) that is at least 1% of the total amount of bacteria in the sample provides a diagnosis of bacterial vaginosis in the subject.

Also provided herein is a method of diagnosing bacterial vaginosis in a subject, comprising: A) contacting a gynecological sample from the subject with a nucleic acid probe specific for prokaryotic nucleic acid under conditions whereby nucleic acid hybridization can occur; B) detecting nucleic acid hybridization and determining the amount of hybridized nucleic acid and the total amount of bacteria in the sample; C) contacting the sample with a first nucleic acid probe specific for BVAB2 and a second nucleic acid probe specific for *Megasphaera*, under conditions whereby nucleic acid hybridization can occur; D) detecting nucleic acid hybridization of (C); E) determining the amount of nucleic acid hybridization of (D) and determining the amount of BVAB2 and the amount of *Megasphaera* in the sample and F) calculating the percentage of BVAB2 and the percentage of *Megasphaera* in the total amount of bacteria in the sample, whereby the presence of BVAB2 and/or *Megasphaera* that is at least 1% of the total amount of bacteria in the sample provides a diagnosis of bacterial vaginosis in the subject.

Additionally provided herein is a method of determining the amount of BVAB2 and *Megasphaera* in a sample, comprising: a) contacting the sample with a probe that hybridizes with a nucleic acid specific for BVAB2 and a second probe that hybridizes with a nucleic acid specific for *Megasphaera* under conditions whereby hybridization can occur; and b) detecting hybridization of nucleic acid of (a) and determining the amount of BVAB2 nucleic acid and the amount of *Megasphaera* nucleic acid and the amount of BVAB2 and *Megasphaera* in the sample.

A further aspect of this invention includes a method of determining the amount of BVAB2 and *Megasphaera* in a sample as a percentage of the total amount of bacteria in the sample, comprising: a) contacting the sample with a probe specific for prokaryotic nucleic acid under conditions whereby hybridization can occur; b) detecting hybridization of nucleic acid of (a) and determining the amount of hybridized nucleic acid and the amount of bacteria in the sample; c) contacting the sample with a first probe specific for BVAB2 and a second probe specific for *Megasphaera* under conditions whereby hybridization can occur; d) detecting hybridization of nucleic acid of (c) and determining the amount of hybridized nucleic acid specific for BVAB2 and the amount of hybridized nucleic acid specific for *Megasphaera* and the amount of BVAB2 and *Megasphaera* in the sample; and e) calculating the percentage of BVAB2 and *Megasphaera* in the total amount of bacteria in the sample.

In yet further embodiments, the present invention provides a method of detecting *Megasphaera* in a sample, comprising: a) contacting the sample with a primer pair specific for nucleic acid comprising the nucleotide sequence of SEQ ID NO:64 (*Megasphaera*) under conditions whereby nucleic acid amplification can occur; and b) detecting amplification of the nucleic acid of (a), thereby detecting *Megasphaera* in the sample. In some embodiments of this method, the primer pair can comprise the nucleotide sequence of forward primer MegaE-458F (SEQ ID NO:19) and the nucleotide sequence of reverse primer MegaE-666R (SEQ ID NO:20) and in other embodiments the primer pair can comprise the nucleotide sequence of forward primer 456F_MegaE (SEQ ID NO:106) and the nucleotide sequence of reverse primer 667R_MegaE (SEQ ID NO:107).

Further provided herein is a method of determining the amount of *Megasphaera* in a sample, comprising: a) contacting the sample with a primer pair specific for nucleic acid comprising the nucleotide sequence of SEQ ID NO:64 (*Megasphaera*) under conditions whereby nucleic acid amplification can occur and the amount of amplified nucleic acid can be determined; and b) detecting amplification of the nucleic acid of (a) and determining the amount of *Megasphaera* nucleic acid and the amount of *Megasphaera* bacteria in the sample. In some embodiments of this method, the primer pair can comprise the nucleotide sequence of forward primer 456F_MegaE (SEQ ID NO:106) and the nucleotide sequence of reverse primer 667R_MegaE (SEQ ID NO:107) and the amplification of nucleic acid can be detected by contacting the nucleic acid of (a) with a detectably labeled probe comprising the nucleotide sequence of Mega__485-506 (SEQ ID NO:108). The probe can be labeled with one or more detectable labels as are well known in the art (e.g., fluorescence labels; chemoluminescence labels).

Also provided herein is a method of detecting *Megasphaera* in a sample, comprising: a) contacting the sample with a probe that hybridizes with a nucleic acid comprising the nucleotide sequence of SEQ ID NO:64 (*Megasphaera*) under conditions whereby nucleic acid hybridization can occur; and b) detecting nucleic acid hybridization of the probe of (a), thereby detecting *Megasphaera* in the sample. In some embodiments of this method, the probe can comprise the nucleotide sequence of SEQ ID NO:108 (Mega__485-506). The probe can be a nucleic acid probe, a PNA probe or any other probe known in the art for use in an assay employing nucleic acid hybridization.

In further aspects of this invention, a method is provided herein for determining the amount of BVAB2 in a sample, comprising: a) contacting the sample with a primer pair specific for nucleic acid comprising the nucleotide sequence of SEQ ID NO:104 (BVAB2) under conditions whereby nucleic acid amplification can occur and the amount of amplified nucleic acid can be determined; and b) detecting amplification of the nucleic acid of (a) and determining the amount of BVAB2 nucleic acid and the amount of BVAB2 bacteria in the sample. In some embodiments of this method, the primer pair can comprise the nucleotide sequence of forward primer 619F_BVAB2 (SEQ ID NO:112) and the nucleotide sequence of reverse primer 879R_BVAB2 (SEQ ID NO:113) and the amplification of nucleic acid can be detected by contacting the nucleic acid of (a) with a detectably labeled probe comprising the nucleotide sequence of BVAB2__643-665 (SEQ ID NO:114).

As an additional aspect of this invention, a method is provided herein for determining the amount of BVAB1 in a sample, comprising: a) contacting the sample with a primer pair specific for nucleic acid comprising the nucleotide sequence of SEQ ID NO:103 (BVAB1) under conditions whereby nucleic acid amplification can occur and the amount of amplified nucleic acid can be determined; and b) detecting amplification of the nucleic acid of (a) and, determining the amount of BVAB1 nucleic acid and the amount of BVAB1 bacteria in the sample. In some embodiments of this method, the primer pair can comprise the nucleotide sequence of forward primer 576F_BVAB1 (SEQ ID NO:109) and the nucleotide sequence of reverse primer 666R_BVAB1 (SEQ ID NO:110) and the amplification of nucleic acid can be detected by contacting the nucleic acid of (a) with a detectably labeled probe comprising the nucleotide sequence of BVAB1__610-637 (SEQ ID NO:111).

Additionally provided herein is a method of determining the amount of BVAB3 in a sample, comprising: a) contacting the sample with a primer pair specific for nucleic acid comprising the nucleotide sequence of SEQ ID NO:105 (BVAB3) under conditions whereby nucleic acid amplification can occur and the amount of amplified nucleic acid can be determined; and b) detecting amplification of the nucleic acid of (a) and determining the amount of BVAB3 nucleic acid and the amount of BVAB3 bacteria in the sample. In some embodiments of this method, the primer pair can comprise the nucleotide sequence of forward primer 1132F_BVAB3 (SEQ ID NO:118) and the nucleotide sequence of reverse primer 1292R_BVAB3 (SEQ ID NO:119) and the amplification of nucleic acid can be detected by contacting the nucleic acid of (a) with a detectably labeled probe comprising the nucleotide sequence of BVAB3__1232-1256 (SEQ ID NO:120).

A further aspect of the present invention is a method of determining the amount of BVAB2 in a sample, comprising: a) contacting the sample with a primer pair specific for nucleic acid comprising the nucleotide sequence of SEQ ID NO:104 (BVAB2) under conditions whereby nucleic acid amplification can occur and the amount of amplified nucleic acid can be determined; and b) detecting amplification of the nucleic acid of (a) and determining the amount of BVAB2 nucleic acid and the amount of BVAB2 bacteria in the sample. In some embodiments of this method, the primer pair can comprise the nucleotide sequence of forward primer 585F_BVAB2 (SEQ ID NO:115) and the nucleotide sequence of reverse primer 666R_BVAB2 (SEQ ID NO:116) and the amplification of nucleic acid can be detected by contacting the nucleic acid of (a) with a detectably labeled probe comprising the nucleotide sequence of BVAB2__613-641 (SEQ ID NO:117) (see, e.g., BVAB2_PATH in Table 10).

Additional aspects of this invention include a method of determining the amount of *Gardnerella vaginalis* in a sample, comprising: a) contacting the sample with a primer pair specific for *G. vaginalis* nucleic acid (SEQ ID NOs:57, 58, 59, 60 and 87) under conditions whereby nucleic acid amplification can occur and the amount of amplified nucleic acid can be determined; and b) detecting amplification of the nucleic acid of (a) and determining the amount of *G. vaginalis* nucleic acid and the amount of *G. vaginalis* bacteria in the sample. In some embodiments of this method, the primer pair can comprise the nucleotide sequence of forward primer 983F_Gvag (SEQ ID NO:121) and the nucleotide sequence of reverse primer 1059R_Gvag (SEQ ID NO:122) and the amplification of nucleic acid can be detected by contacting the nucleic acid of (a) with a detectably labeled probe comprising the nucleotide sequence of Gvag_1008-1032 (SEQ ID NO:123).

Furthermore, the present invention provides a method of determining the amount of *Leptotrichia* and/or *Sneathia* in a sample, comprising: a) contacting the sample with a primer pair specific for *Leptotrichia* (SEQ ID NO:102) and/or *Sneathia* (SEQ ID NO:51) nucleic acid under conditions whereby nucleic acid amplification can occur and the amount of amplified nucleic acid can be determined; and b) detecting amplification of the nucleic acid of (a) and determining the amount of *Leptotrichia* and/or *Sneathia* nucleic acid and the amount of *Leptotrichia* and/or *Sneathia* bacteria in the sample. In some embodiments of this method, the primer pair can comprise the nucleotide sequence of forward primer 559F_Lepto/Sneath (SEQ ID NO:124) and the nucleotide sequence of reverse primers 659R_Lepto (SEQ ID NO:125) and/or 660R_Sneath (SEQ ID NO:126) and the amplification of nucleic acid can be detected by contacting the nucleic acid of (a) with a detectably labeled probe comprising the nucleotide sequence of Lepto/Sneath_593-618 (SEQ ID NO:127).

Additionally provided herein is a method of determining the amount of *Lactobacillus* in a sample, comprising: a) contacting the sample with a primer pair specific for *Lactobacillus* nucleic acid (SEQ ID NO:52 *L. jensenii;* SEQ ID NO:55 *L. Crispatus* alpha; SEQ ID NO:56 *L. crispatus* beta; SEQ ID NO:61 *L. iners;* SEQ ID NO:62 *L. gasseri* type 1; SEQ ID NO:63 *L. gasseri* type 2; SEQ ID NO:72 *Lactobacillus* sp.) under conditions whereby nucleic acid amplification can occur and the amount of amplified nucleic acid can be determined; and b) detecting amplification of the nucleic acid of (a) and determining the amount of *Lactobacillus* nucleic acid and the amount of *Lactobacillus* bacteria in the sample. In some embodiments of this method, the primer pair can comprise the nucleotide sequence of forward primer 1130F_JLacto (SEQ ID NO:128) and the nucleotide sequence of reverse primer 1283R_Lacto (SEQ ID NO:129) and the amplification of nucleic acid can be detected by contacting the nucleic acid of (a) with a detectably labeled probe comprising the nucleotide sequence of Lacto_1234-1261 (SEQ ID NO:130).

Various other objectives and advantages of the present invention will become apparent from the following detailed description.

BRIEF DESCRIPTION OF THE DRAWINGS

FIGS. 2A-F. Rank abundance plots showing the percentage of clones in each library corresponding to particular bacterial 16S rDNA sequences. Figure legends display percent similarities between the cloned 16S rDNA sequences and the most similar 16S rDNA sequences in Genbank. Figures A and B show vaginal bacteria detected by broad range 16S rDNA PCR before (A) and after (B) onset of BV in one subject. *Lactobacillus crispatus* was replaced by a complex consortium of bacteria. Figures C and D show vaginal bacteria with BV (C) and after successful antibiotic treatment for BV (D) in another subject. Disease resolution was associated with loss of the diverse bacterial community and colonization with *Lactobacillus* species. Figure E shows vaginal bacteria present in a subject with BV in which BVAB 1 was the dominant bacterial 16S rDNA sequence detected. Figure F shows results from a 420-clone analysis from one subject with BV. BVAB 1,2, and 3 were present in this library along with 18 other bacterial species. Compare to the results of the 100-clone analysis for BV7 in Table 3.

DETAILED DESCRIPTION OF THE INVENTION

Figure 1:
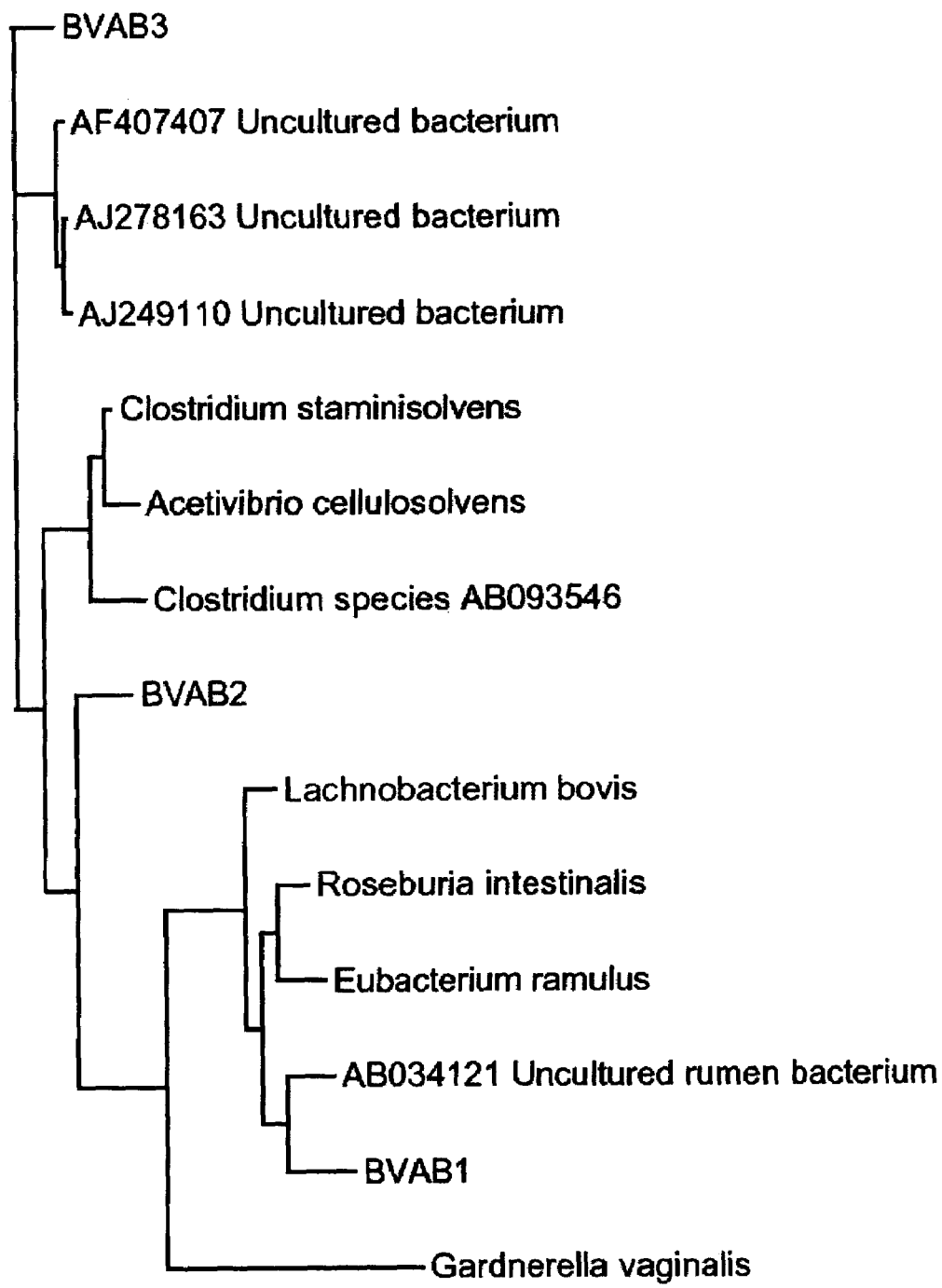
FIG. 1. Phylogenetic tree of inferred evolutionary relationships among bacteria based on aligned 16S rDNA sequences using a maximum likelihood algorithm. BVAB 1, 2, and 3 are related to bacteria in the Clostridium phylum, though they are not closely related to any bacterium with known 16S rDNA sequence. Horizontal distances indicate evolutionary relatedness and the bar represents 0.1 base changes per nucleotide position. Genbank accession numbers are provided for uncultivated bacteria.

As used herein, "a" or "an", or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is based on the unexpected discovery of particular bacterial species in samples from subjects with bacterial vaginosis, as identified by characterization of their ribosomal DNA (rDNA) sequences.

Thus, in one embodiment, the present invention provides an isolated nucleic acid comprising, consisting essentially of and/or consisting of a nucleotide sequence identified as GenBank accession number AY738656 (SEQ ID NO:48), AY738657 (SEQ ID NO:49), AY738658 (SEQ ID NO:50), AY738659 (SEQ ID NO:51), AY738660 (SEQ ID NO:52), AY738661 (SEQ ID NO:53), AY738662 (SEQ ID NO:54), AY738663 (SEQ ID NO:55), AY738664 (SEQ ID NO:56), AY738665 (SEQ ID NO:57), AY738666 (SEQ ID NO:58), AY738667 (SEQ ID NO:59), AY738668 (SEQ ID NO:60), AY738669 (SEQ ID NO:61), AY738670 (SEQ ID NO:62), AY738671 (SEQ ID NO:63), AY738672 (SEQ ID NO:64), AY738673 (SEQ ID NO:65), AY738674 (SEQ ID NO:66), AY738675 (SEQ ID NO:67), AY738676 (SEQ ID NO:68), AY738677 (SEQ ID NO:69), AY738678 (SEQ ID NO:70), AY738679 (SEQ ID NO:71), AY738680 (SEQ ID NO:72), AY738681 (SEQ ID NO:73), AY738682 (SEQ ID NO:74), AY738683 (SEQ ID NO:75), AY738684 (SEQ ID NO:76), AY738685 (SEQ ID NO:77), AY738686 (SEQ ID NO:78), AY738687 (SEQ ID NO:79), AY738688 (SEQ ID NO:80), AY738689 (SEQ ID NO:81), AY738690 (SEQ ID NO:82), AY738691 (SEQ ID NO:83), AY738692 (SEQ ID NO:84), AY738693 (SEQ ID NO:85), AY738694 (SEQ ID NO:86), AY738695 (SEQ ID NO:87), AY738696 (SEQ ID NO:88), AY738697 (SEQ ID NO:89), AY738698 (SEQ ID NO:90), AY738699 (SEQ ID NO:91), AY738700 (SEQ ID NO:92), AY738701 (SEQ ID NO:93), AY738702 (SEQ ID NO:94), AY738703 (SEQ ID NO:95), AY738704 (SEQ ID NO:96), AY738705 (SEQ ID NO:97), AY738706 (SEQ ID NO:98), AY724739 (SEQ ID NO:99), AY724740 (SEQ ID NO:100), AY724741 (SEQ ID NO:1021, AY724742 (SEQ ID NO:102), bankit643633 (SEQ ID NO:103), bankit655126 (SEQ ID NO:104) and bankit655138 (SEQ ID NO:105) (Table 5). These nucleic acids can be present individually and/or in any combination in a sample of this invention. In some embodiments of this invention, one or more of the nucleic acids recited herein, in any combination can be absent from a sample.

In further embodiments, the present invention also provides a bacterium, which can be an isolated bacterium and/or present as a bacterium in a population and/or in a sample (e.g., identified in a sample), which is a thin curved rod, comprising a ribosomal DNA comprising the nucleotide sequence of GenBank Accession No. bankit643633 (SEQ ID NO:103, bacterial vaginosis associated bacterium 1; BVAB 1), a bacterium, which can be an isolated bacterium and/or present as a bacterium in a population and/or in a sample (e.g., identified in a sample), which is a short wide rod, comprising a ribosomal DNA comprising the nucleotide sequence of GenBank Accession No. bankit655126 (SEQ ID NO:104, bacterial vaginosis associated bacterium 2; BVAB 2), and a bacterium, which can be an isolated bacterium and/or present as a bacterium in a population and/or in a sample (e.g., identified in a sample), which is a long lancet-shaped rod, comprising a ribosomal DNA comprising the nucleotide sequence of GenBank Accession No. bankit655138 (SEQ ID NO:105, bacterial vaginosis associated bacterium 3; BVAB 3).

Additionally provided herein is a method of detecting BVAB 1 in a sample, comprising: a) contacting the sample with a first oligonucleotide primer comprising the nucleotide sequence of primer BVAB1-1019F (Uncxb1-649F, SEQ ID NO:3, forward primer) and a second oligonucleotide primer comprising the nucleotide sequence of primer BVAB1-1280R (Uncxb1-908R, SEQ ID NO:4, reverse primer) under conditions whereby amplification of nucleic acid in the sample can occur; and b) detecting amplification of nucleic acid specific for BVAB 1, thereby detecting BVAB 1 in the sample.

Also provided herein is a method of detecting BVAB 2 in a sample, comprising: a) contacting the sample with a first oligonucleotide primer comprising the nucleotide sequence of primer BVAB2-619F (Uncxb2-619F, SEQ ID NO:5, forward primer) and a second oligonucleotide primer comprising the nucleotide sequence of primer BVAB2-1024R (Uncxb2-1023R, SEQ ID NO:6, reverse primer) under conditions whereby amplification of nucleic acid in the sample can occur; and b) detecting amplification of nucleic acid specific for BVAB 2, thereby detecting BVAB 2 in the sample.

Further provided herein is a method of detecting BVAB 3 in a sample, comprising: a) contacting the sample with a first oligonucleotide primer comprising the nucleotide sequence of primer BVAB3-999F (Uncxb3-1000F, SEQ ID NO:7, forward primer) and a second oligonucleotide primer comprising the nucleotide sequence of primer BVAB3-1278R (Uncxb3-1278R, SEQ ID NO:8 reverse primer) under conditions whereby amplification of nucleic acid in the sample can occur; and b) detecting amplification of nucleic acid specific for BVAB 3, thereby detecting BVAB 3 in the sample.

In other embodiments, the present invention provides a method of detecting BVAB 1 in a sample, comprising: a) contacting the sample with a nucleotide sequence comprising the nucleotide sequence of Uncxb1-134-F1 (SEQ ID NO:42) under conditions whereby nucleic acid hybridization can occur; and b) detecting nucleic acid hybridization, thereby detecting BVAB1 in the sample.

Furthermore, the present invention provides a method of detecting BVAB 2 in a sample, comprising: a) contacting the sample with a nucleotide sequence comprising the nucleotide sequence of Uncxb2-1244-Cy3 (SEQ ID NO:43) under conditions whereby nucleic acid hybridization can occur; and b) detecting nucleic acid hybridization, thereby detecting BVAB 2 in the sample.

In addition, the present invention provides a method of detecting BVAB 3 in a sample, comprising: a) contacting the sample with a nucleotide sequence comprising the nucleotide sequence of Uncxb3-1244-Cy3 (SEQ ID NO:44) under conditions whereby nucleic acid hybridization can occur; and b) detecting nucleic acid hybridization, thereby detecting BVAB 3 in the sample.

In yet other embodiments, the present invention provides a method of diagnosing bacterial vaginosis in a subject, comprising: 1) contacting a gynecological sample from the subject with one or more oligonucleotide primer pairs selected from the group consisting of: a) BVAB1-1019F/BVAB1-1280R (SEQ ID NOS:3 and 4, detects BVAB1); b) BVAB2-619F/BVAB2-1024R (SEQ ID NOS:5 and 6, detects BVAB 2); c) BVAB3-999F/BVAB3-1278R (SEQ ID NOS:7 and 8, detects BVAB 3); d) G.vag 644F/G.vag 851R (SEQ ID NOS:9 and 10, detects *Gardnerella vaginalis*); e) Ato-442F/Ato-1017R (SEQ ID NOS:11 and 12, detects Atopobium sp.); f) Egger-621F/Egger-859R (SEQ ID NOS:13 and 14, detects *Eggerthella* sp.); g) Lepto-395F/Lepto-646R (SEQ ID NOS:15 and 16, detects *Leptotrichia* sp.); h) MegaE-456F/MegaE-667R (SEQ ID NOS:19 and 20, detects *Megasphaera* Type I); i) MegaM-453F/MegaM-666R (SEQ ID NOS:17 and 18, detects *Megasphaera* Type II); j) TM7-641F/TM7-1020R (SEQ ID NOS:21 and 22, detects BVAB-TM7); k) P.lacri-999F/Pepton-1184R (SEQ ID NOS:23 and 24, detects *Peptoniphilus lacrimalis*); l) Pepton-1003F/Pepton-1184R (SEQ ID NOS:25 and 24, detects *Peptoniphilus* sp.); m) M.curt-440F/M.curt-1026R (SEQ ID NOS:26 and 27, detects *Mobiluncus curtisii*); n) Mobil-577F/M.mulie-1026R (SEQ ID NOS:28 and 29, detects *Mobiluncus mulieris*); o) PrevG1-468F/PrevG1-857R (SEQ ID NOS:30 and 31, detects *Prevotella* G1); p) PrevG2-648F/PrevG2-871R (SEQ ID NOS:32 and 33, detects *Prevotella* G2); q) L.crisp-452F/L.crisp-1023R (SEQ ID NOS:34 and 35, detects *Lactobacillus crispatus*); r) L.iners-453F/L.iners-1022R (SEQ ID NOS:36 and 37, detects *Lactobacillus iners*); and s) any combination of (a)-(r), under conditions whereby amplification of nucleic acid in the sample can occur; and 2) detecting amplification of nucleic acid specific for one or more bacteria selected from the group consisting of: i) BVAB 1; ii) BVAB 2; iii) BVAB 3; iv) *Gardnerella vaginalis*; v) *Atopobium* sp.; vi) *Eggerthella* sp.; vii) *Leptotrichia* sp.; viii) *Megasphaera* Type I; ix) *Megasphaera* Type II; x) BVAB-TM7; xi) *Peptoniphilus lacrimalis*; xii) *Peptoniphilus* sp.; xiii) *Mobiluncus curtisii*; xiv) *Mobiluncus mulieris*; xv) *Prevotella* G1; xvi) *Prevotella G2*; xvii) *Lactobacillus crispatus*; xviii) *Lactobacillus iners;* and xix) any combination of (i)-(xvii), thereby diagnosing bacterial vaginosis in the subject.

In the methods of this invention, the gynecological sample can be contacted with one, two, three, four, five, six, seven or eight or more different oligonucleotide primer pairs of step (1) and nucleic acid specific for one, two, three, four, five, six, seven or eight or more of the bacteria of step (2) can be detected.

Additionally provided is a method of diagnosing bacterial vaginosis in a subject comprising detecting one or more of the following bacterial species in a gynecological sample from the subject: BVAB1; BVAB 2; BVAB 3; *Gardnerella vaginalis; Atopobium* sp.; *Eggerthella* sp.; *Leptotrichia* sp.; *Megasphaera* Type I; *Megasphaera* Type II; BVAB-TM7; *Peptoniphilus lacrimalis; Peptoniphilus* sp.; *Mobiluncus curtisii; Mobiluncus mulieris; Prevotella* G1; *Prevotella* G2; *Lactobacillus crispatus;* and *Lactobacillus iners*. The detected bacterial species can be present in the sample of the subject in an amount greater than the amount present in a sample from a subject without bacterial vaginosis. The bacterial species can also be present in the sample of the subject in a combination that is not found in a sample from a subject without bacterial vaginosis. Additionally, the bacterial species can be present in the sample of the subject in a percentage of the total bacterial population in the subject that is greater than the percentage of the total bacterial population in a sample from a subject without bacterial vaginosis. The bacterial species can be detected in the gynecological sample according to methods described herein as well as methods well known in the art for the detection and/or identification of bacterial species.

In a further embodiment, the present invention provides a method of detecting BVAB2 and *Megasphaera* in a sample, comprising: a) contacting the sample with a first primer pair specific for a nucleic acid comprising the nucleotide sequence of SEQ ID NO:104 (BVAB2) and a second primer pair specific for a nucleic acid comprising the nucleotide sequence of SEQ ID NO:64 (*Megasphaera*) under conditions whereby nucleic acid amplification can occur; and b) detecting amplification of nucleic acid of (a), thereby detecting BVAB2 and *Megasphaera* in the sample. As one nonlimiting example, in this method, the first primer pair can comprise, consist essentially of and/or consist of the nucleotide sequence of forward primer Uncxb2-619F (SEQ ID NO:5) and the nucleotide sequence of reverse primer Uncxb2-1023R (SEQ ID NO:6) and the second primer can comprise, consist essentially of and/or consist of the nucleotide sequence of forward primer MegaE-458F (SEQ ID NO:19) and the nucleotide sequence of reverse primer MegaE-666R (SEQ ID NO:20). It would be well understood that other suitable primers that are specific for the nucleic acids of this method could be designed and produced according to art known methods and that the present invention is intended to encompass any and all such primers.

Further provided herein is a method of detecting BVAB2 and *Megasphaera* in a sample, comprising: a) contacting the sample with a first probe that hybridizes with a nucleic acid comprising the nucleotide sequence of SEQ ID NO:104 (BVAB2) and a second probe that hybridizes with a nucleic acid comprising the nucleotide sequence of SEQ ID NO:64 (*Megasphaera*) under conditions whereby nucleic acid hybridization can occur; and b) detecting nucleic acid hybridization of the first probe and second probe, thereby detecting BVAB2 and *Megasphaera* in the sample. A nonlimiting example of a first probe of this method can comprise, consist essentially of and/or consist of the nucleotide sequence of SEQ ID NO:44 (Uncxb2-1244-Cy3) and a second probe of this method can comprise, consist essentially of and/or consist of the nucleotide sequence of SEQ ID NO:108 (Mega_ 485-506). It would be well understood that other suitable probes can be designed and produced according to methods well known in the art and any and all such other probes are encompassed within this invention.

In yet another embodiment, the present invention provides a method of detecting BVAB1 in a sample, comprising: a) contacting the sample with a probe that hybridizes with a nucleic acid comprising the nucleotide sequence of SEQ ID NO:103 under conditions whereby nucleic acid hybridization can occur; and b) detecting nucleic acid hybridization, thereby detecting BVAB1 in the sample. A nonlimiting example of a probe for this method comprises, consists essentially of and/or consists of the nucleotide sequence of SEQ ID NO:43 (Uncxb1-134-F1). It would be well understood that other suitable probes can be designed and produced according to methods well known in the art and any and all such other probes are encompassed within this invention.

In addition, the present invention provides a method of detecting BVAB2 in a sample, comprising: a) contacting the sample with a probe that hybridizes with a nucleic acid comprising the nucleotide sequence of SEQ ID NO:104 under conditions whereby nucleic acid hybridization can occur; and b) detecting nucleic acid hybridization, thereby detecting BVAB2 in the sample. A nonlimiting example of a probe suitable for use in this method comprises, consists essentially of and/or consists of the nucleotide sequence of SEQ ID NO:44 (Uncxb2-1244-Cy3). It would be well understood that other suitable probes can be designed and produced according to methods well known in the art and any and all such other probes are encompassed within this invention.

Additionally provided herein is a method of detecting BVAB3 in a sample, comprising: a) contacting the sample with a probe that hybridizes with a nucleic acid comprising the nucleotide sequence of SEQ ID NO:105 under conditions whereby nucleic acid hybridization can occur; and b) detecting nucleic acid hybridization, thereby detecting BVAB3 in the sample. A nonlimiting example of a probe suitable for this method comprises, consists essentially of and/or consists of the nucleotide sequence of SEQ ID NO:45 (Uncxb3-1244-Cy3). It would be well understood that other suitable probes can be designed and produced according to methods well known in the art and any and all such other probes are encompassed within this invention.

The present invention further provides a method of detecting BVAB1 in a sample, comprising: a) contacting the sample with a primer pair specific for a nucleic acid comprising the nucleotide sequence of SEQ ID NO:103 under conditions whereby nucleic acid amplification can occur; and b) detecting amplification of nucleic acid specific for BVAB1, thereby detecting BVAB1 in the sample. A nonlimiting example of a primer pair of this invention comprises, consists essentially of and/or consists of a forward primer comprising the nucleotide sequence of SEQ ID NO:3 (Uncxb1-649F) and a reverse primer comprising the nucleotide sequence of SEQ ID NO:4 (Uncxb1-908R). It would be well understood that other suitable primers that are specific for the nucleic acids of this method could be designed and produced according to art known methods and that the present invention is intended to encompass any and all such primers.

In an additional embodiment, the present invention provides a method of detecting BVAB2 in a sample, comprising: a) contacting the sample with a primer pair specific for a nucleic acid comprising the nucleotide sequence of SEQ ID NO:104 under conditions whereby nucleic acid amplification can occur; and b) detecting amplification of nucleic acid specific for BVAB2, thereby detecting BVAB2 in the sample. A nonlimiting example of a primer pair of this method can be a forward primer comprising, consisting essentially of and/or consisting of the nucleotide sequence of SEQ ID NO:5 (Uncxb2-619F) and a reverse primer comprising, consisting essentially of and/or consisting of the nucleotide sequence of SEQ ID NO:6 (Uncxb2-1023R). It would be well understood that other suitable primers that are specific for the nucleic acids of this method could be designed and produced according to art known methods and that the present invention is intended to encompass any and all such primers.

Additionally provided herein is a method of detecting BVAB3 in a sample, comprising: a) contacting the sample with a primer pair specific for a nucleic acid comprising the nucleotide sequence of SEQ ID NO:105 under conditions whereby amplification of nucleic acid in the sample can occur; and b) detecting amplification of nucleic acid specific for BVAB3, thereby detecting BVAB3 in the sample. A nonlimiting example of a primer pair suitable for use in this method is a forward primer comprising, consisting essentially of and/or consisting of the nucleotide sequence of SEQ ID NO:7 (Uncxb3-1000F) and a reverse primer comprising, consisting essentially of and/or consisting of the nucleotide sequence of SEQ ID NO:8 (Uncxb3-1278R).

The present invention further provides a method of diagnosing bacterial vaginosis in a subject, comprising: A) contacting a gynecological sample (e.g., vaginal, labial, cervical, urine, vaginal washings, vaginal secretions, vaginal tissue, anal, rectal, endometrial, fetal, placental, oral, saliva, skin swab or scraping, etc.) from the subject with one or more primer pairs selected from the group consisting of: a) a primer pair specific for a nucleic acid comprising, consisting essentially of and/or consisting of the nucleotide sequence of SEQ ID NO:103 (BVAB1); b) a primer pair specific for a nucleic acid comprising, consisting essentially of and/or consisting of the nucleotide sequence of SEQ ID NO:104 (BVAB2); c) a primer pair specific for a nucleic acid comprising, consisting essentially of and/or consisting of the nucleotide sequence of SEQ ID NO:105 (BVAB3); d) a primer pair specific for a nucleic acid comprising, consisting essentially of and/or consisting of the nucleotide sequence of SEQ ID NO:57, SEQ ID NO:58, SEQ ID NO:59, SEQ ID NO:60 and/or SEQ ID NO:87 (*Gardnerella vaginalis*); e) a primer pair specific for a nucleic acid comprising, consisting essentially of and/or consisting of the nucleotide sequence of SEQ ID NO:49 and/or SEQ ID NO:50 (*Atopobium* sp.); f) a primer pair specific for a nucleic acid comprising, consisting essentially of and/or consisting of the nucleotide sequence of SEQ ID NO:48 (*Eggerthella* sp.); g) a primer pair specific for a nucleic acid comprising, consisting essentially of and/or consisting of the nucleotide sequence of SEQ ID NO:51 and/or SEQ ID NO:102 (*Leptotrichia* sp.; *Sneathia* sp.); h) a primer pair specific for a nucleic acid comprising, consisting essentially of and/or consisting of the nucleotide sequence of SEQ ID NO:64 (*Megasphaera* sp.); and i) any combination of (a)-(h) above, under conditions whereby nucleic acid amplification can occur; and B) detecting amplification of nucleic acid specific for one or more of the bacteria selected from the group consisting of: a) BVAB1; b) BVAB2; c) BVAB3; d) *Gardnerella vaginalis*; e) *Atopobium* sp.; f) *Eggerthella* sp.; g) *Leptotrichia* sp. or *Sneathia* sp.; h) *Megasphaera* sp.; and i) any combination of (a)-(h), thereby diagnosing bacterial vaginosis in the subject. It would be well understood that this method can be carried out by applying a single primer pair to the sample to detect any one of the different types of target nucleic acids of this method and that multiple primer pairs can be applied to the sample, either one at a time or in multiples at the same time or both, in any order and in any combination to detect more than one type of target nucleic acid. Furthermore, the detection of a single type of nucleic acid can-be diagnostic and combinations of the different nucleic acids can be diagnostic as well. For example, the detection of BVAB2 and/or *Megasphaera* nucleic acid in the sample can be diagnostic of bacterial vaginosis. Thus, in some embodiments, the sample can be contacted with two, three, four or more primer pairs of step (A).

Nonlimiting examples of primer pairs of the above-recited method can include a primer pair of (a) comprising, consisting essentially of and/or consisting of a forward primer comprising, consisting essentially of and/or consisting of the nucleotide sequence of SEQ ID NO:3 (Uncxb1-649F) and a reverse primer comprising, consisting essentially of and/or consisting of the nucleotide sequence of SEQ ID NO:4 (Uncxb1-908R). A further example can include a primer pair of (b) comprising, consisting essentially of and/or consisting of a forward primer comprising, consisting essentially of and/or consisting of the nucleotide sequence of SEQ ID NO:5 (Uncxb2-619F) and a reverse primer comprising, consisting essentially of and/or consisting of the nucleotide sequence of SEQ ID NO:6 (Uncxb2-1023R). A further example can include a primer pair of (c) comprising, consisting essentially of and/or consisting of a forward primer comprising, consisting essentially of and/or consisting of the nucleotide sequence of SEQ ID NO:7 (Uncxb3-1000F) and a reverse primer comprising, consisting essentially of and/or consisting of the nucleotide sequence of SEQ ID NO:8 (Uncxb3-1278R). A further example can include a primer pair of (d) comprising, consisting essentially of and/or consisting of a forward primer comprising, consisting essentially of and/or consisting of the nucleotide sequence of SEQ ID NO:9 (G.vag 643F) and a reverse primer comprising, consisting essentially of and/or consisting of the nucleotide sequence of SEQ ID NO:10 (G. vag 846R). A further example can include a primer pair of (e) comprising, consisting essentially of and/or consisting of a forward primer comprising, consisting essentially of and/or consisting of the nucleotide sequence of SEQ ID NO:11 (Ato-441F) and a reverse primer comprising, consisting essentially of and/or consisting of the nucleotide sequence of SEQ ID NO:12 (Ato-1016R). A further example is a primer pair of (f) comprising, consisting essentially of and/or consisting of a forward primer comprising, consisting essentially of and/or consisting of the nucleotide sequence of SEQ ID NO:13 (Egger-630F) and a reverse primer comprising, consisting essentially of and/or consisting of the nucleotide sequence of SEQ ID NO:14 (Egger-854R). A further example is of a primer pair of (g) comprising, consisting essentially of and/or consisting of a forward primer comprising, consisting essentially of and/or consisting of the nucleotide sequence of SEQ ID NO:15 (Lepto-394F) and a reverse primer comprising, consisting essentially of and/or consisting of the nucleotide sequence of SEQ ID NO:16 (Lepto-645R). A further example is of a primer pair of (h) comprising, consisting essentially of and/or consisting of a forward primer comprising, consisting essentially of and/or consisting of the nucleotide sequence of SEQ ID NO:19 (MegaE-458F) and a reverse primer comprising, consisting essentially of and/or consisting of the nucleotide sequence of SEQ ID NO:20 (MegaE-666R). It would be well understood that other suitable primers that are specific for the nucleic acids of this method could be designed and produced according to art known methods and that the present invention is intended to encompass any and all such primers.

The present invention additionally provides a method of diagnosing bacterial vaginosis in a subject, comprising: A) contacting a gynecological sample of the subject with a primer pair specific for a nucleic acid selected from the group consisting of: a) a nucleic acid comprising, consisting essentially of and/or consisting of the nucleotide sequence of SEQ ID NO:103 (BVAB1); b) a nucleic acid comprising, consisting essentially of and/or consisting of the nucleotide sequence of SEQ ID NO:104 (BVAB2); c) a nucleic acid comprising, consisting essentially of and/or consisting of the nucleotide sequence of SEQ ID NO:105 (BVAB3); d) a nucleic acid comprising, consisting essentially of and/or consisting of the nucleotide sequence of SEQ ID NO:57, SEQ ID NO:58, SEQ ID NO:59, SEQ ID NO:60 and/or SEQ ID NO:87 (*Gardnerella vaginalis*); e) a nucleic acid comprising, consisting essentially of and/or consisting of the nucleotide sequence of SEQ ID NO:49 and/or SEQ ID NO:50 (*Atopobium* sp.); f) a nucleic acid comprising, consisting essentially of and/or consisting of the nucleotide sequence of SEQ ID NO:48 (*Eggerthella* sp.); g) a nucleic acid comprising, consisting essentially of and/or consisting of the nucleotide sequence of SEQ ID NO:51 and/or SEQ ID NO:102 (*Leptotrichia* sp.; *Sneathia* sp.); h) a primer pair specific for a nucleic acid comprising, consisting essentially of and/or consisting of the nucleotide sequence of SEQ ID NO:64 (*Megasphaera* sp.); and i) any combination of (a)-(h), under conditions whereby nucleic acid amplification can occur and the amount of amplified nucleic acid can be determined; B) detecting amplification of a nucleic acid of (A) above; C) determining the amount of the amplified nucleic acid of (B); and D) comparing the amount of amplified nucleic acid of (C) with the amount of amplified nucleic acid of the same bacterial species from a gynecological sample of a control subject who does not have bacterial vaginosis, whereby an increase in the amount of nucleic acid of (C) relative to the control subject provides a diagnosis of bacterial vaginosis in the subject. In some embodiments of this method, the amount of nucleic acid of (C) can be at least 1%, 2%, 3%, 4%, 5%, 6%, 7%, 8%, 9%, 10%, 11%, 12% 13%, 14%, 15%, 16%, 17%, 18%, 19%, 20%, 25%, 30%, 35%, 40%, 50%, 75% or 100% more than the amount of nucleic acid of the same bacterial species from the control subject. A single bacterial species can be increased relative to the control to identify a percent increase over control and/or a combination of bacterial species can be increased relative to a control to yield a total percent over control. For example, the presence of BVAB2 in an amount that is 1% greater than control can be diagnostic. As. another example, a combination of BVAB2 and *Megasphaera* in a total amount that is 1% greater than control can be diagnostic.

In additional embodiments, the present invention provides a method of diagnosing bacterial vaginosis in a subject, comprising: A) contacting a gynecological sample of the subject with a primer pair specific for prokaryotic nucleic acid in the sample under conditions whereby nucleic acid amplification can occur and the amount of amplified nucleic acid can be quantitated to determine the total amount of bacteria in the sample; B) detecting amplification of nucleic acid in (A) and determining the amount of amplified nucleic acid and the total amount of bacteria in the sample; C) contacting the sample with a primer pair specific for a nucleic acid selected from the group consisting of: a) a nucleic acid comprising, consisting essentially of and/or consisting of the nucleotide sequence of SEQ ID NO:103 (BVAB1); b) a nucleic acid comprising, consisting essentially of and/or consisting of the nucleotide sequence of SEQ ID NO:104 (BVAB2); c) a nucleic acid comprising, consisting essentially of and/or consisting of the nucleotide sequence of SEQ ID NO:105 (BVAB3); d) a nucleic acid comprising, consisting essentially of and/or consisting of the nucleotide sequence of SEQ ID NO:57, SEQ ID NO:58, SEQ ID NO:59, SEQ ID NO:60 and/or SEQ ID NO:87 (*Gardnerella vaginalis*); e) a nucleic acid comprising, consisting essentially of and/or consisting of the nucleotide sequence of SEQ ID NO:49 and/or SEQ ID NO:50 (*Atopobium* sp.); f) a nucleic acid comprising, consisting essentially of and/or consisting of the nucleotide sequence of SEQ ID NO:48 (*Eggerthella* sp.); g) a nucleic acid comprising, consisting essentially of and/or consisting of the nucleotide sequence of SEQ ID NO:51 and/or SEQ ID NO:102 (*Leptotrichia* sp.; *Sneathia* sp.); h) a nucleic acid comprising, consisting essentially of and/or consisting of the nucleotide sequence of SEQ ID NO:64 (*Megasphaera* sp.); and i) any combination of (a)-(h), under conditions whereby nucleic acid amplification can occur and the amount of amplified nucleic acid can be determined; and D) detecting amplification of a nucleic acid of (C) above; E) determining the amount of the amplified nucleic acid of (B) and the amount of each bacterial species specific for the nucleic acid of (C); and F calculating the percentage of each bacterial species of (E) in the total amount of bacteria in the sample, whereby the presence of any one or more than one of the bacterial species of (E) that is at least 1%, 2%, 3%, 4%, 5%, 6%, 7%, 8%, 9%, 10%, 11%, 12% 13%, 14%, 15%, 16%, 17%, 18%; 19%, 20%, 25%, 30%, 35%, 40%, 50%, 75% or 100% of the total amount of the bacteria in the sample provides a diagnosis of bacterial vaginosis in the subject. As noted above, the bacterial species of (E) can be a single type of bacteria or a combination of bacteria detected by this method to yield the percent of bacterial species of (E) in the total amount of bacteria in the sample.

The present invention also provides a method of determining the amount of BVAB2 and *Megasphaera* in a sample, comprising: a) contacting the sample with a first primer pair specific for a nucleic acid comprising, consisting essentially of and/or consisting of the nucleotide sequence of SEQ ID NO:104 (BVAB2) and a second primer pair specific for a nucleic acid comprising, consisting essentially of and/or consisting of the nucleotide sequence of SEQ ID NO:64 (*Megasphaera*) under conditions whereby nucleic acid amplification can occur and the amount of amplified nucleic acid can be determined; and b) detecting amplification of nucleic acid of (a) and determining the amount of BVAB2 and *Megasphaera* nucleic acid and the amount of BVAB2 and *Megasphaera* in the sample. Examples of primers suitable for this method are described herein and can be designed and produced according to methods well known in the art.

Further provided herein is a method of determining the amount of BVAB2 in a sample as a percentage of the total amount of bacteria in the sample, comprising: a) contacting the sample with a primer pair specific for prokaryotic nucleic acid under conditions whereby nucleic acid amplification can occur and the amount of amplified nucleic acid can be determined; b) detecting amplification of nucleic acid in (a) and determining the amount of amplified nucleic acid and the total amount of bacteria in the sample; c) contacting the sample with a primer pair specific for a nucleic acid comprising, consisting essentially of and/or consisting of the nucleotide sequence of SEQ ID NO:104 (BVAB2) under conditions whereby nucleic acid amplification can occur and the amount of amplified nucleic acid can be determined; d) detecting amplification of nucleic acid of (c) and determining the amount of nucleic acid specific for BVAB2 and the amount of BVAB2 bacteria in the sample; and e) calculating the percentage of BVAB2 bacteria in the total amount of bacteria in the sample.

Methods for the design and production of primers that can specifically amplify prokaryotic nucleic acid are well known in the art and any and all such primers are included with the present invention. A nonlimiting example of such a primer pair comprises, consists essentially of and/or consists of SEQ ID NO:1 (Bact-338F) and SEQ ID NO:2 (Bact-1407R). An example of the design of additional primer pairs includes the downloading of a large number of ribosomal RNA sequences of different bacterial species into multiple sequencing alignment software and/or primer and probe design software, aligning the sequences and identifying conserved regions among the aligned sequences as targets for primer and probe design. Once such primers and probes are designed, they can be synthesized or produced according to methods well known in the art.

Further provided herein is a method of determining the amount of *Megasphaera* in a sample as a percentage of the total amount of bacteria in the sample, comprising: a contacting the sample with a primer pair specific for prokaryotic nucleic acid under conditions whereby nucleic acid amplification can occur and the amount of amplified nucleic acid can be determined; b) detecting amplification of nucleic acid in (a) and determining the amount of amplified nucleic acid and the total amount of bacteria in the sample; c) contacting the sample with a primer pair specific for a nucleic acid comprising, consisting essentially of and/or consisting of the nucleotide sequence of SEQ ID NO:64 under conditions whereby nucleic acid amplification can occur and the amount of amplified nucleic acid can be determined; and d) detecting amplification of nucleic acid of (c) and determining the amount of *Megasphaera* nucleic acid and the amount of *Megasphaera* bacteria in the sample; and e) calculating the percentage of *Megasphaera* bacteria in the total amount of bacteria in the sample.

In addition, the present invention provides a method of diagnosing bacterial vaginosis in a subject, comprising: a) contacting a gynecological sample of the subject with a primer pair specific for prokaryotic nucleic acid in the sample under conditions whereby nucleic acid amplification can occur and the amount of amplified nucleic acid can be quantitated to determine the total amount of bacteria in the sample; b) detecting amplification of nucleic acid of (a); c) determining the amount of amplified nucleic acid of (b) and the total amount of bacteria in the sample; d) contacting the sample with a first primer pair specific for nucleic acid comprising, consisting essentially of and/or consisting of the nucleotide sequence of SEQ ID NO:104 (BVAB2) and a second primer pair specific for nucleic acid comprising, consisting essentially of and/or consisting of the nucleotide sequence of SEQ ID NO:64 (*Megasphaera*) under conditions whereby nucleic acid amplification can occur and the amount of amplified nucleic acid can be determined; e) detecting amplification of nucleic acid of (d); f) determining the amount of amplified nucleic acid of (e) and the amount of BVAB2 and *Megasphaera* sp. bacteria in the sample; and g) calculating the percentage of each of the BVAB2 and *Megasphaera* in the total amount of bacteria in the sample, whereby the presence of an amount of BVAB2 and/or *Megasphaera* that is at least 1%, 2%, 3%, 4%, 5%, 6%, 7%, 8%, 9%, 10%, 11%, 12% 13%, 14%, 15%, 16%, 17%, 18%, 19%, 20%, 25%, 30%, 35%, 40%, 50%, 75% or 100% of the total amount of the bacteria in the sample provides a diagnosis of bacterial vaginosis in the subject.

The present invention additionally provides a method of diagnosing bacterial vaginosis in a subject, comprising: A) contacting a gynecological sample of the subject with a nucleic acid probe that hybridizes with nucleic acid specific for a bacterium selected from the group consisting of: a) BVAB1; b) BVAB2; c) BVAB3; d) *Mobiluncus*; e) *Gardnerella*; f) *Atopobium*; g) *Megasphaera;* and h) any combination of (a)-(g) above, under conditions whereby nucleic acid hybridization can occur; and B) detecting nucleic acid hybridization, thereby diagnosing bacterial vaginosis in the subject. Non-limiting examples of probes suitable in this method are described herein and it is well understood that other suitable primers can be designed and produced according to well known methods and that any and all such probes are included as part of this invention.

A method of diagnosing bacterial vaginosis in a subject, comprising: A) contacting a gynecological sample of the subject with a nucleic acid probe that hybridizes with nucleic acid specific for a bacterium selected from the group consisting of: a) BVAB1; b) BVAB2; c) BVAB3; d) *Mobiluncus*; e) *Gardnerella*; f) *Atopobium*; g) *Megasphaera;* and h) any combination of (a)-(g) above, under conditions whereby nucleic acid hybridization can occur; and B) detecting nucleic acid hybridization, C) determining the amount of hybridized nucleic acid of (B); and D) comparing the amount of the hybridized nucleic acid of (C) with the amount of hybridized nucleic acid of the same bacterial species from a gynecological sample of a control subject who does not have bacterial vaginosis, whereby an increase in the amount of the nucleic acid of (C) relative to the control subject provides a diagnosis of bacterial vaginosis in the subject. In this method, the amount of nucleic acid of (C) can be at least 1%, 2%, 3%, 4%, 5%, 6%, 7%, 8%, 9%, 10%, 11%, 12% 13%, 14%, 15%, 16%, 17%, 18%, 19%, 20%, 25%, 30%, 35%, 40%, 50%, 75% or 100% greater than the amount of the nucleic acid of the same bacterial species or combination of bacterial species from the control subject.

In addition, the present invention provides a method of diagnosing bacterial vaginosis in a subject, comprising: a) contacting a gynecological sample of the subject with a first nucleic acid probe that hybridizes with nucleic acid specific for BVAB2 and a second nucleic acid probe that hybridizes with *Megasphaera*, under conditions whereby nucleic acid hybridization can occur; and b) detecting nucleic acid hybridization, thereby diagnosing bacterial vaginosis in the subject.

Further provided herein is a method of diagnosing bacterial vaginosis in a subject, comprising: A) contacting a gynecological sample of the subject with a first nucleic acid probe that hybridizes with nucleic acid specific for BVAB2 and a second nucleic acid probe that hybridizes with *Megasphaera* under conditions whereby nucleic acid hybridization can occur; and B) detecting nucleic acid hybridization, C) determining the amount of hybridized nucleic acid of BVAB2 and the amount of hybridized nucleic acid of *Megasphaera;* and D) comparing the amount of the hybridized nucleic acid of (C) with the amount of hybridized nucleic acid of BVAB2 and/or *Megasphaera* from a gynecological sample of a control subject who does not have bacterial vaginosis, whereby an increase in the amount of the nucleic acid of (C) relative to the control subject provides a diagnosis of bacterial vaginosis in the subject. The amount of hybridized nucleic acid of BVAB2 and/or *Megasphaera* can be at least 1%, 2%, 3%, 4%, 5%, 6%, 7%, 8%, 9%, 10%, 11%, 12% 13%, 14%, 15%, 16%, 17%, 18%, 19%, 20%, 25%, 30%, 35%, 40%, 50%, 75% or 100% greater than the amount of hybridized nucleic acid of BVAB2 and/or *Megasphaera* from the control subject.

In yet additional embodiments, the present invention provides a method of diagnosing bacterial vaginosis in a subject, comprising: A) contacting a gynecological sample from the subject with a nucleic acid probe specific for prokaryotic nucleic acid under conditions whereby nucleic acid hybridization can occur; B) detecting nucleic acid hybridization and determining the amount of hybridized nucleic acid and the total amount of bacteria in the sample; C) contacting the sample with a nucleic acid probe specific for a bacterium selected from the group consisting of: a) BVAB1; b) BVAB2; c) BVAB3; d) Mobiluncus; e) Gardnerella; f) Atopobium; g) *Megasphaera;* and h) any combination of (a)-(g) above, under conditions whereby nucleic acid hybridization can occur; D) detecting nucleic acid hybridization of (C); E) determining the amount of nucleic acid hybridization of (D) and determining the amount of each bacterial species specific for the nucleic acid of (C); and F) calculating the percentage of each bacterial species of (E) in the total amount of bacteria in the sample, whereby the presence of any one or more than one of the bacterial species of (E) that is at least 1%, 2%, 3%, 4%, 5%, 6%, 7%, 8%, 9%, 10%, 11%, 12% 13%, 14%, 15%, 16%, 17%, 18%, 19%, 20%, 25%, 30%, 35%, 40%, 50%, 75% or 100% of the total amount of bacteria in the sample provides a diagnosis of bacterial vaginosis in the subject.

The present invention further provides a method of diagnosing bacterial vaginosis in a subject, comprising: A) contacting a gynecological sample from the subject with a nucleic acid probe specific for prokaryotic nucleic acid under conditions whereby nucleic acid hybridization can.occur; B) detecting nucleic acid hybridization and determining the amount of hybridized nucleic acid and the total amount of bacteria.in the sample; C) contacting the sample with a first nucleic acid probe specific for BVAB2 and a second nucleic acid probe specific for *Megasphaera*, under conditions whereby nucleic acid hybridization can occur; D) detecting nucleic acid hybridization of (C); E) determining the amount of nucleic acid hybridization of (D) and determining the amount of BVAB2 and the amount of *Megasphaera* in the sample and F) calculating the percentage of BVAB2 and the percentage of *Megasphaera* in the total amount of bacteria in the sample, whereby the presence of BVAB2 and/or *Megasphaera* that is at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 50%, 75% or 100%) of the total amount of bacteria in the sample provides a diagnosis of bacterial vaginosis in the subject.

Additionally provided is a method of determining the amount of BVAB2 and *Megasphaera* in a sample, comprising: a) contacting the sample with a probe that hybridizes with a nucleic acid specific for BVAB2 and a second probe that hybridizes with a nucleic acid specific for *Megasphaera* under conditions whereby hybridization can occur; and b) detecting hybridization of nucleic acid of (a) and determining the amount of BVAB2 nucleic acid and the amount of *Megasphaera* nucleic acid and the amount of BVAB2 and *Megasphaera* in the sample.

In a further embodiment, the present invention provides a method of determining the amount of BVAB2 and *Megasphaera* in a sample as a percentage of the total amount of bacteria in the sample, comprising: a) contacting the sample with a probe specific for prokaryotic nucleic acid under conditions whereby hybridization can occur; b) detecting hybridization of nucleic acid of (a) and determining the amount of hybridized nucleic acid and the amount of bacteria in the sample; c) contacting the sample with a first probe specific for BVAB2 and a second probe specific for *Megasphaera* under conditions whereby hybridization can occur; d) detecting hybridization of nucleic acid of (c) and determining the amount of hybridized nucleic acid specific for BVAB2 and the amount of hybridized nucleic acid specific for *Megasphaera* and the amount of BVAB2 and *Megasphaera* in the sample; and e) calculating the percentage of BVAB2 and *Megasphaera* in the total amount of bacteria in the sample.

In the methods of this invention that recite the use of a primer pair to amplify a target. nucleic acid, it is understood that such a method is exemplary of one of a variety of methods for amplification of nucleic acid, some of which employ primers and primer pairs and some of which amplify by other means, as is well known in the art. Thus, the methods of this invention wherein amplification of nucleic acid is described are not intended to be limited to amplification methods employing only primer pairs and other such amplification methods are described herein and are well known in the art.

Furthermore, the terms "under conditions whereby nucleic acid amplification can occur" and "under conditions whereby nucleic acid hybridization can occur" and variations thereof would be well recognized by one of ordinary skill in the art to mean conditions employing specific reagents, solutions, temperature, pH and/or physical conditions that allow for amplification of nucleic acid and/or hybridization of nucleic acid according to protocols well known in the art. Furthermore, claims that refer to conditions whereby the amount of amplified nucleic acid or hybridized nucleic acid can be quantitated describe conditions that are also well known to the ordinary person of skill in the art. In particular, methods of determining the amount of amplified nucleic acid are well known for such protocols as PCR (e.g., quantitative PCR or qPCR) and other amplification protocols and method of determining the amount of hybridized nucleic acid both semi-quantitatively and quantitatively are also well known in the art and as described herein.

A sample of this invention can include but is not limited to a gynecological sample (e.g., vaginal, labial, vulvar, cervical, urine, vaginal fluid, vaginal washings, vaginal secretions, vaginal tissue, anal, rectal, endometrial, fetal, placental, chorioamniotjc, oral, salivary, skin swab or scraping, etc.), vaginal sample, labial sample, endometrial sample, cervical sample, rectal/anal sample, oral sample (e.g., saliva, tongue swab or scraping, inner cheek swab or scraping, tooth swab or scraping), fallopian tube sample, ovary sample, peritoneal fluid or biopsy sample, amniotic fluid sample, fetal tissue sample, placenta/chorioamniotic tissue sample, urine sample, blood sample, plasma sample, serum sample, skin swab or sample, etc.

A subject of this invention is any animal that can serve as a host for the bacteria of this invention, including but not limited to mammals (rats, mice, non-human primates) and in particular embodiments, humans.

The term "nucleic acid" as used herein refers to single- or double-stranded molecules that can be DNA, comprised of the nucleotide bases A, T, C and G, or RNA, comprised of the bases A, U (substitutes for T), C, and G. The nucleic acid can represent a coding strand or its complement. Nucleic acids can be identical in sequence to the sequence that is naturally occurring or can include alternative codons, which encode the same amino acid as that which is found in the naturally occurring sequence. Furthermore, nucleic acids may include codons that provide conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

In particular embodiments, the probes and/or primers of this invention can have at least about 50%, 60%, 70%, 75%, 80%, 85%, 90%, 95%, 98% or more nucleic acid sequence homology with the sequences specifically disclosed herein. The term "homology" as used herein refers to a degree of similarity between two or more sequences. There may be partial homology or complete homology (i.e., identity). A partially complementary sequence that at least partially inhibits an identical sequence from hybridizing to a target nucleic acid is referred to as "substantially homologous." The inhibition of hybridization of the completely complementary sequence to the target sequence can be examined using a hybridization assay (e.g., Southern or Northern blot, solution hybridization and the like) under conditions of low stringency. A substantially homologous sequence or hybridization probe will compete for and inhibit the binding of a completely homologous sequence to the target sequence under conditions of low stringency, as this term is known in the art. This is not to say that conditions of low stringency are such that non-specific binding is permitted; low stringency conditions require that the binding of two sequences to one another be a specific (i.e., selective) interaction. The absence of non-specific binding can be tested by the use of a second target sequence that lacks even a partial degree of complementarity (e.g., less than about 30% identity). In the absence of non-specific binding, the probe will not hybridize to the second non-complementary target sequence.

The term "hybridization" as used herein refers to any process by which a first strand of nucleic acid binds with a second strand of nucleic acid through base pairing. Nucleic acids encoding the polypeptides and/or fragments of this invention can be detected by DNA-DNA or DNA-RNA hybridization or amplification using probes, primers and/or fragments of polynucleotides encoding the polypeptides and/or fragments of this invention and/or designed to detect and/or amplify the nucleic acids of this invention.

The term "hybridization complex" as used herein refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells and/or nucleic acids have been fixed).

The term "nucleotide sequence" refers to a heteropolymer of nucleotides or the sequence of these nucleotides. The terms "nucleic acid," "oligonucleotide" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene. Nucleic acids of this invention can comprise a nucleotide sequence that can be identical in sequence to the sequence which is naturally occurring or, due to the well-characterized degeneracy of the nucleic acid code, can include alternative codons which encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained.

The term "probe" or "primer" includes naturally occurring or recombinant or chemically synthesized single- and/or double-stranded nucleic acids. They can be labeled for detection by nick translation, Klenow fill-in reaction, PCR or other methods well known in the art. A probe or primer can be an oligonucleotide and can comprise any number of nucleotides and in some embodiments can comprise, for example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80. 90, 100, 125, 150, 175, 200, 250, 300 nucleotides or more as appropriate for the particular assay in which it will be used. Probes and primers of the present invention, their preparation and/or labeling are described in Sambrook et al. 1989. *Molecular Cloning. A Laboratory Manual*, Cold Spring Harbor Laboratory, NY and Ausubel et al. 1989. *Current Protocols in Molecular Biology*, John Wiley & Sons, New York N.Y., both of which are incorporated herein by reference in their entirety for these teachings.

The term "stringent" as used herein refers to hybridization conditions that are commonly understood in the art to define the conditions of the hybridization procedure. Stringency conditions can be low, high or medium, as those terms are commonly know in the art and well recognized by one of ordinary skill. In various embodiments, stringent conditions can include, for example, highly stringent (i.e., high stringency) conditions (e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

Another example of stringency conditions can be hybridization in 25% formamide, 5×SSC, 5× Denhardt's solution, with 100 μg/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions (e.g., high stringency) can be represented by a wash stringency of 0.3M NaCl, 0.03 M sodium citrate, 0.1%

SDS at 60° or even 70° C. using a standard in situ hybridization assay. (Sambrook et al., *Molecular Cloning, A Laboratory Manual* (2d ed. 1989)).

"Amplification" as used herein includes the production of multiple copies of a nucleic acid molecule and is generally carried out using polymerase chain reaction (PCR) and/or other amplification technologies as are well known in the art (Dieffenbach and Dveksler. 1995. *PCR Primer, a Laboratory Manual*, Cold Spring Harbor Press, Plainview, N.Y.).

A number of assays for detection and/or amplification of nucleic acid sequences are well known in the art. Additionally, a wide variety of labeling and conjugation techniques are known in the art that are used in various nucleic acid detection and amplification assays. Methods for producing labeled hybridization probes and/or PCR or other ligation primers for detecting and/or amplifying nucleic acid sequences can include, for example, oligolabeling, nick translation and end-labeling, as well as other well known methods. Alternatively, nucleic acid sequences of this invention can be cloned into a plasmid or vector for detection and amplification. Such plasmids and vectors are well known in the art and are commercially available. It is also contemplated that the methods of this invention can be conducted using a variety of commercially available kits (e.g., Pharmacia & Upjohn; Promega; U.S. Biochemical Corp.). Suitable reporter molecules or labels, which can be used for ease of detection, include, for example, radionuclides, enzymes, fluorescence agents, chemiluminescence agents and chromogenic agents, as well as substrates, cofactors, inhibitors, magnetic particles and the like, as are well known in the art.

Various protocols can be employed in the methods of this invention to amplify nucleic acid. As used herein, the term "oligonucleotide-directed amplification procedure" refers to template-dependent processes that result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term "template dependent process" refers to nucleic acid synthesis of an RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided in U.S. Pat. No. 4,237,224, specifically incorporated herein by reference in its entirety. Nucleic acids, used as a template for amplification methods, can be isolated from cells according to standard methodologies (Sambrook et al., 1989). The nucleic acid can be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids of this invention are contacted with the target nucleic acid under conditions that permit selective hybridization. The term "primer," as defined herein, is meant to encompass any nucleic acid that is capable of priming the synthesis of a nascent nucleic acid in a template dependent process. Typically, primers are oligonucleotides from ten to twenty base pairs in length, but shorter or longer sequences can be employed. Primers and probes may be provided in double-stranded or single-stranded form, although the single-stranded form is commonly used.

Once hybridized, the nucleic acid: primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (e.g., Affymax technology).

A number of template dependent processes are available to amplify the sequences present in a given template sample. One of the best-known amplification methods is the polymerase chain reaction (referred to as PCR), which is described in detail in U.S. Pat. Nos. 4,683,195, 4,683,202 and 4,800,159, each incorporated herein by reference in its entirety.

Briefly, in PCR, two primer sequences are prepared that are complementary to regions on opposite complementary strands of the target sequence. An excess of deoxynucleoside triphosphates is added to a reaction mixture along with a DNA polymerase, e.g., a Taq polymerase. If the particular target sequence is present in a sample, the primers will bind to the target sequence and the polymerase will cause the primers to be extended along the sequence by adding on nucleotides. By raising and lowering the temperature of the reaction mixture, the extended primers will dissociate from the target sequence to form reaction products, excess primers will bind to the target sequence and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermo stable, RNA-dependent DNA polymerases. These methods are described, for example, in WO 90/07641, filed Dec. 21, 1990, incorporated herein by reference in its entirety. Polymerase chain reaction methodologies are well known in the art. Modifications to amplification assays such as PCR to allow for quantitative analysis of the amplified products are also well known in the art and such protocols and reagents are available in various commercial embodiments.

Another method for amplification is the ligase chain reaction ("LCR"), disclosed in Eur. Pat. Appl. No. 320308, incorporated herein by reference in its entirety. In LCR, two complementary probe pairs are prepared and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Q beta Replicase (QβR), described in Intl. Pat. Appl. Publ. No.PCT/US87/00880, incorporated herein by reference, can also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744,311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present.

The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method, as described in Great Britain Patent 2202328, and in Intl. Pat. Appl. Publ. No.PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact, available to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7, T3 or SP6. In an isothermal cyclic reaction, the RNAs are reverse transcribed into single stranded DNA, which is then converted to double-stranded DNA, and then transcribed once again with an RNA polymerase such as T7, T3 or SP6. The resulting products, whether truncated or complete, indicate target specific sequences.

Davey et al., Eur. Pat. Appl. No. 329822 (incorporated herein by reference in its entirety) discloses a nucleic acid amplification process involving cyclically synthesizing single stranded RNA (ssRNA), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA).

The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA (dsDNA) molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) discloses a nucleic acid sequence amplification scheme based on the hybridization of a promoter/primer sequence to a target single-stranded DNA (ssDNA) followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference).

Methods based on ligation of two (or more) oligonucleotides in the presence of nucleic acid having the sequence of the resulting "di-oligonucleotide," thereby amplifying the dioligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography that can be used in the present invention: such as, for example, adsorption, partition, ion exchange and molecular sieve, as well as many specialized techniques for using them including column, paper, thin-layer and gas chromatography.

Amplification products must be visualized in order to confirm amplification of the target sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified target sequence. The probe preferably is conjugated to a chromophore but may be radiolabeled. In another embodiment, the probe is conjugated to a binding partner, such as an antibody or biotin, and the other member of the binding pair carries a detectable moiety.

In other embodiments, detection is by Southern blotting and hybridization with a labeled probe. The techniques involved in Southern blotting are well known to those of skill in the art and can be found in many standard books on molecular protocols (Sambrook et al., 1989). Briefly, amplification products are separated by gel electrophoresis. The gel is then contacted with a membrane, such as nitrocellulose, permitting transfer of the nucleic acid and noncovalent binding. Subsequently, the membrane is incubated with a chromophore-conjugated probe that is capable of hybridizing with a target amplification product. Detection is by exposure of the membrane to x-ray film or ion-emitting detection devices. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

The nucleic acid of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid of this invention.

The nucleic acid of this invention can also include, for example, antibiotic resistance markers and/or other selectable and/or screenable markers as are known in the art, origins of replication and/or expression control sequences, such as, for example, a promoter (constitutive or inducible), an enhancer and necessary information processing sites, such as initiation signals, ribosome binding sites, RNA splice sites, multiple cloning sites, polyadenylation sites and transcriptional terminator sequences. The nucleic acid of this invention can also comprise one or more internal ribosome binding sites (IRES) for expression of more than one coding sequence from the same construct.

A nucleic acid encoding a peptide or polypeptide of this invention can readily be determined based upon the genetic code for the amino acid sequence of the selected peptide or polypeptide and many nucleic acids will encode any selected peptide or polypeptide, based upon the redundancy of the genetic code. Modifications in the nucleic acid sequence encoding the peptide or polypeptide are also contemplated. Modifications that can be useful are modifications to the sequences controlling expression of the peptide or polypeptide to make production of the peptide or polypeptide inducible or repressible as controlled by the appropriate inducer or repressor. Such methods are standard in the art. The nucleic acid of this invention can be generated by means standard in the art, such as by recombinant nucleic acid techniques and/or by synthetic nucleic acid synthesis and/or in vitro enzymatic synthesis.

The present invention further provides a vector comprising a nucleic acid of this invention. The vector of this invention can be any type of vector that facilitates delivery of nucleic acid to a cell. A vector of this invention can be a nucleic acid vector such as a plasmid, cosmid, virus, and/or an artificial chromosome. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols.

In some embodiments, the expression vector can comprise, for example, viral nucleic acid including, but not limited to, nucleic acid from vaccinia virus, adenovirus, lentivirus, retrovirus, pseudotyped virus (e.g., pseudotyped lentivirus, pseudotyped retrovirus), alphavirus, herpesvirus, vaccinia virus, polyoma virus, picornavirus, hybrid adeno/adeno-associated virus and/or adeno-associated virus (AAV; see for example, Owens (2002) "Second generation adeno-associated virus type 2-based gene therapy systems with the potential for preferential integration into AAVS1" *Curr. Gene Ther.* 2:145-159, the entire contents of which are incorporated herein by reference for teachings of AAV vectors), as well as any other viral vector now known or later identified according to methods well known in the art.

In yet other embodiments, the vector of this invention can be any vehicle for delivery of nucleic acid into a cell that is lipid-, peptide-, and/or protein-based. For example, the nucleic acid or vector of this invention can also be in a liposome (e.g., FuGene6; VDL liposomes) or a delivery vehicle, which can be taken up by a cell via receptor-mediated or other type of endocytosis. The vectors, liposomes and other delivery vehicles of this invention can further comprise molecules on the surface that allow for specific cell targeting and binding, as are well known in the art.

Introduction of the nucleic acids of this invention into cells can be achieved by any of numerous, well-known approaches, for example, but not limited to, direct transfer of the nucleic acids, in a plasmid or viral vector, calcium phosphate mediated gene delivery, lipofection, electroporation, uptake by cells via endocytosis, microinjection and/or proteoliposomes and/or via transfer in cells or in combination with carriers such as cationic liposomes. Such methods are well known in the art and readily adaptable for use in the herein. Furthermore, these methods can be used to target certain cell populations by using the targeting characteristics of the carrier, which would be well known to the skilled artisan.

Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used nucleic acid transfer methods. Appropriate means for transfection, including viral vectors, chemical transfectants, or physicomechanical methods such as electroporation and direct diffusion of DNA, are described by, for example, Wolff et al., *Science* 247:1465-1468, (1990); and Wolff, *Nature* 352:815-818, (1991).

Thus, in various embodiments, the nucleic acid of this invention can be in a cell, which can be a cell expressing the nucleic acid of this invention. In addition, the vector of this invention can be in a cell, which can be a cell expressing the nucleic acid of the vector in the cell.

Thus, one embodiment of this invention is a method of producing a cell of this invention, comprising transducing and/or transfecting a cell of this invention with a vector and/or nucleic acid of this invention. Also provided is a cell produced by the methods of this invention.

The present invention additionally provides kits comprising the nucleic acid compositions of this invention, along with appropriate buffers, diluents, vessels and/or devices, etc. for carrying out the detection, identification and/or diagnostic methods of this invention. For example, a kit of this invention can comprise a first primer pair and/or a probe specific for detection of BVAB2 and/or a second primer pair and/or probe specific for the detection of *Megasphaera* bacteria. Such a kit can further comprise the appropriate reagents, solutions and buffers for amplification, sample dilution, detection, etc.

EXAMPLES

Example 1

Study population: The first 73 women enrolled were studied out of a total of 87 women recruited from two groups known to have high BV prevalence[17-20]: sexually transmitted disease (STD) clinic clients (Public Health, Seattle & King County STD Clinic (14 subjects)) and women who reported same sex behavior in the previous year, most of whom were also sexually active with male partners (Harborview Women's Research Clinic (WRC) (59 subjects)). Women were eligible if they were 16 to 45 years old and able to provide written informed consent. Single baseline vaginal fluid samples from the 73 subjects were studied using bacterium specific 16S rDNA PCR, including 27 subjects with BV as defined by Amsel clinical criteria[12] and 46 subjects without BV. Vaginal fluid samples from 21 of these 73 subjects were studied using broad range bacterial 16S rDNA PCR with clone analysis, including single baseline samples from 9 subjects with BV and 8 subjects without BV, and multiple follow-up samples from 4 subjects with either incident (new), resolved, relapsed, or persistent BV (11 samples). At both clinics, subjects underwent speculum examination with collection of vaginal fluid for saline microscopy, KOH preparation, pH measurement, and assessment for amine odor. Subjects at the STD clinic were tested routinely for *Chlamydia trachomatis* and *Neisseria gonorrhoeae*, and those seen at the WRC were tested using standard screening and diagnostic criteria[21]. Vaginal fluid was collected for molecular studies by brushing the lateral vaginal wall with a foam swab that was subsequently frozen. Written informed consent was obtained from all participants in this prospective study that was approved by institutional review boards at the Fred Hutchinson Cancer Research Center and the University of Washington. Samples were collected between Oct. 16, 2001 and May 5, 2004. All authors analyzed the data and participated in writing the manuscript.

Sample preparation: Swabs for polymerase chain reaction (PCR) were placed in 15 ml conical tubes with saline and vortex mixed to dislodge cells. Sham swabs (no patient contact) were processed in parallel to monitor for contamination of reagents. Saline solution was centrifuged at 14,000×g for 10 minutes and the supernatant was discarded. The pellet was digested using the Qiamp stool kit (Qiagen Corporation) following the manufacturer's instructions with a 95° C. lysis step.

Molecular analyses: Methods for broad range 16S rDNA PCR, bacterium-specific PCR, and fluorescence in situ hybridization (FISH) are described herein.

Statistical Analysis: The vaginal fluid samples were assessed in real time and the decision to stop the analysis at 73 subjects was based on data showing that there were statistically significant associations between detection of several bacterial species and BV. Differences in number of taxa detected in BV and control libraries were assessed using the Mann-Whitney U test. Univariate associations between detection of individual bacteria by bacterium-specific PCR and the presence of BV were measured by Fisher's exact test with SPSS (release 10.1.4) and exact confidence intervals were calculated using STATA (version 8.2). Multivariate logistic regression analysis was performed using LogXact (version 4.0.2), and covariates in addition to individual bacteria and combinations of bacteria by bacterium-specific PCR included subject age, clinic site of enrollment, report of abnormal vaginal discharge, and report of sex with men. All tests for statistical significance were two-sided and a level of $P<0.05$ was considered significant.

Of the 73 enrolled women, 27 had BV at baseline and 46 did not (Table 2). Slightly more than half of women with BV were symptomatic, and very few had another genitourinary infection in addition to BV.

Broad range bacterial 16S rDNA PCR with analysis of cloned sequences was performed on 28 vaginal fluid samples from 21 subjects. Table 3 displays the bacterial species (phylotypes) detected and the percentage of clones from each library derived from these bacteria. Among subjects for whom only single baseline samples were evaluated (Bacterial vaginosis group and Controls, Table 3), those without BV had a mean of 3.3 bacterial phylotypes per library (range 1-6). *Lactobacillus* species were the dominant bacteria detected (83-100% of clones per library, mean 97%), particularly *Lactobacillus crispatus* and *Lactobacillus iners*. Most bacterial 16S rDNA sequences among subjects without BV closely matched known bacteria.

Broad range bacterial 16S rDNA PCR analysis of vaginal fluid from subjects with BV demonstrated a high level of species diversity (Table 3), with a mean of 12.6 bacterial phylotypes per clone library (range 9-17), significantly higher than for subjects without BV ($p<0.001$). Overall, novel bacterial phylotypes (bacteria with 16S rDNA<98% similar to known sequences) were present in 58% of clones per BV sample library (range 32-89%). *Lactobacillus crispatus* 16S rDNA was not detected in clone libraries from subjects with BV, while *Lactobacillus iners* was detected in most subjects. *Gardnerella vaginalis* was detected in all BV clone libraries and *Mobiluncus mulieris* in one library. *Mycoplasma* species were not detected in any clone library, despite sequence homology with the broad range 16S rDNA PCR primers employed. Other bacteria frequently detected in subjects with BV included *Atopobium vaginae*, two *Megasphaera* species, two distinct Dialister phylotypes, *Leptotrichia amnionii* and the related bacterium *Sneathia sanguinegens*, *Porphyromonas Asaccharolytica*, and a bacterium distantly related to *Eggerthella honkongensis* (92% sequence similarity). Eleven different bacteria related to *Prevotella* species were detected. Three phylogenetic clusters of these bacteria were only distantly related to known *Prevotella* species (<95% sequence similarity) and are designated *Prevotella* genogroups 1, 2, and 3, based on shared sequences within each group. Less frequently detected bacteria included members of the TM7 division of uncultivated bacteria, and bacteria in the *Peptoniphilus, Peptostreptococcus, Gemella, Aerococcus, Anaerococcus*, and *Veillonella* genera.

Three novel bacteria were detected only in clone libraries from subjects with BV, provisionally named Bacterial Vaginosis-Associated Bacterium (BVAB) 1, 2 and 3. Identical 16S rDNA sequences from these bacteria were detected in numerous BV sample libraries. FIG. 1 is a phylogenetic tree depicting the inferred evolutionary relationships between these bacteria and their closest relatives based on aligned 16S rDNA sequences. BVAB 1, 2, and 3 are related to bacteria in the Clostridium phylum but are not closely related to any bacteria with known 16S rDNA sequences. For instance, 16S rDNA from BVAB 1 is only 90.6% similar to the closest sequence in Genbank (AB034121) that is derived from an uncultivated bacterium detected in bovine rumen.

FIG. 2 shows a series of rank-abundance plots identifying the bacterial 16S rDNA sequence types detected in vaginal fluid and their frequency in six clone libraries from Table 3.

Results from sequential, prospectively obtained samples are displayed from two subjects. In one subject, lactobacilli predominated at baseline when BV was not present, but were replaced by a diverse community of bacteria when BV was subsequently detected two months later. In a second subject with BV at baseline, the diverse community of vaginal bacteria shifted to a predominance of lactobacilli one month after successful treatment of BV.

Table 4 shows the results of bacterium-specific PCR assays applied to 73 vaginal fluid samples from subjects with and without BV at baseline. BVAB 1 was found in 41% of BV samples by bacterium-specific PCR, but was present in up to 63% of clones per library (Table 3). BVAB 2 was found in 89% and BVAB 3 in 44% of BV samples by specific PCR, but these bacteria were never dominant in 16S rDNA clone libraries from subjects with BV, unlike BVAB 1. BVAB 1, 2, and 3 were highly specific indicators of BV. Two subjects without BV at baseline had positive PCR assays for these bacteria (BVAB 1+2, or 2+3), and both developed BV within a few months of these tests. Detection of Leptotrichia sp. was also very specific for BV. Although G. vaginalis was present in all subjects with BV by bacterium specific PCR, it was also found in 59% of subjects without BV. Other bacterium specific PCR assays demonstrated that Atopobium sp., *Megasphaera* sp., and an Eggerthella-like uncultured bacterium were detected in a high percentage of subjects with BV and these assays had moderate specificity for BV. Detection of each of the bacteria listed in Table 4 in vaginal fluid was significantly associated with BV (p<0.001). Combinations of bacterium-specific PCR assays did not substantially improve sensitivity or specificity, except for the combinations of BVAB1 and BVAB 3 that yielded 100% specificity, and the combination of BVAB2 or *Megasphaera* that yielded 100% sensitivity.

Figure 3:
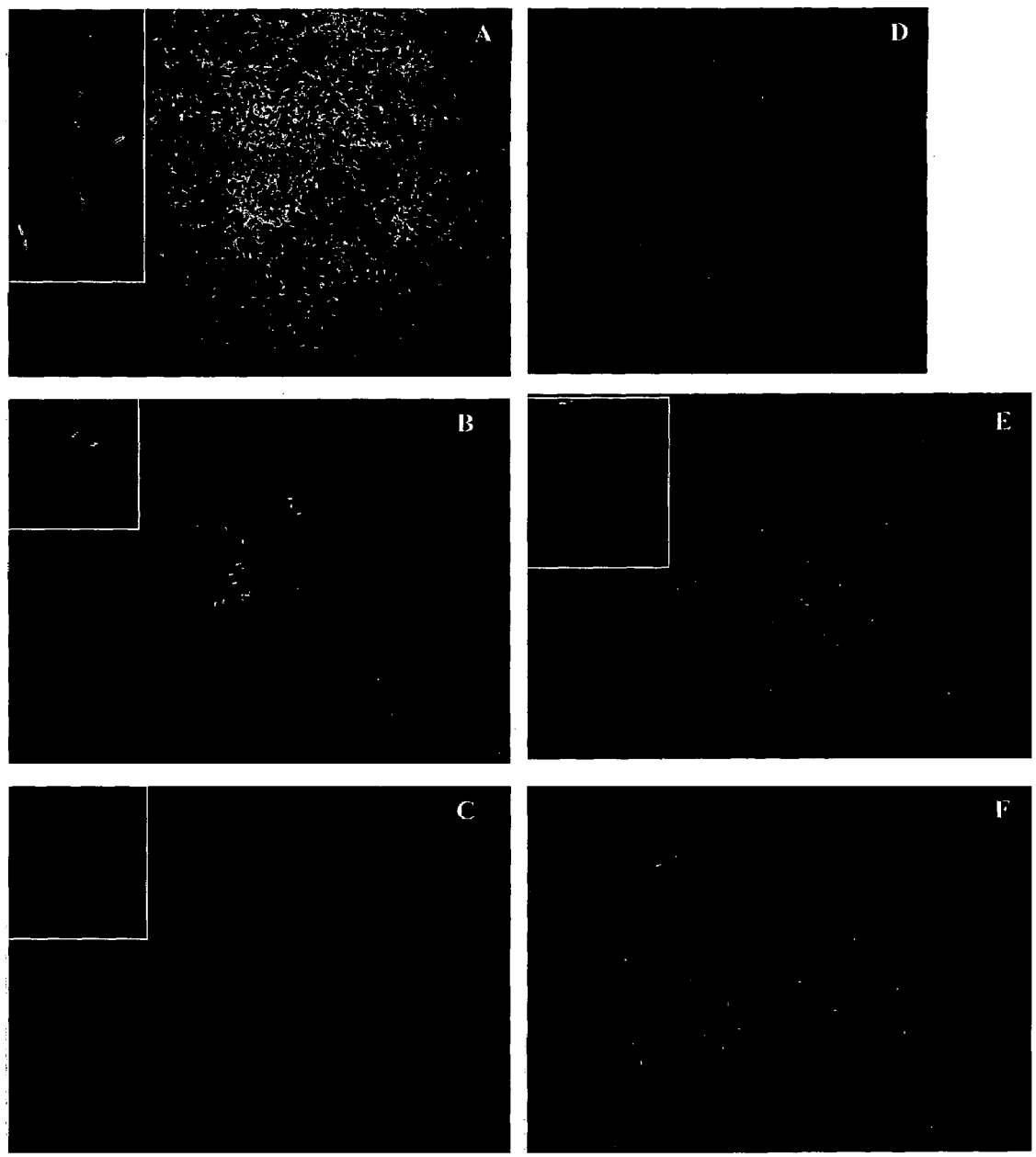
FIGS. 3A-F. Fluorescence micrographs of vaginal fluid smears subjected to fluorescence in situ hybridization using labeled oligonucleotide probes targeting bacterial ribosomal RNA. (A) Vaginal fluid from subject BV6 has a field of bacteria hybridizing with probes for BVAB 1 (green), BVAB 2 (red), and other bacteria (DAPI, blue). Inset is an enlargement showing that BVAB 1 is a thin curved rod. The red bar indicates scale and is 10 microns across. (B) Sample BV6 with bacteria attached to a vaginal epithelial cell. Bacteria visualized include organisms hybridizing with probes for BVAB 1 (green) and BVAB 2 (red). The cell nucleus is stained with DAPI (blue). The inset enlargement shows that BVAB 2 is a short wide rod (red) compared to the thin curved rod shape of BVAB1 (green). (C) Bacteria attached to a vaginal epithelial cell in sample L4b hybridize with probe for BVAB 3 (red). Other bacteria and nuclear debris stain with DAPI (blue). Inset enlargement shows that BVAB 3 is a long, lancet shaped rod. BVAB 1,2, and 3 have distinct morphologies by FISH. (D) A clump of bacteria from sample L4b with numerous coccoid cells hybridizing with the Atopobium probe (red) and other bacteria hybridizing with the broad range bacterial probe Eub338 (blue). (E) Mobiluncus species and BVAB 1 are both small curved rods, but they are easily distinguished by hybridization with specific probes. In sample L4b, bacteria hybridize with probe for BVAB 1 (green) and Mobiluncus (red), while the broad range bacterial probe Eub338 hybridizes with other bacteria (blue). Inset is an enlargement showing that Mobiluncus (red) is larger than BVAB 1 (green). (F) Sample BV7 showing the relative proportions of BVAB 1 (green), *Gardnerella vaginalis* (red), and other bacteria (DAPI, blue). *G. vaginalis* and BVAB1 were the most common clones detected in the broad range PCR library generated from this sample. A large percentage of bacteria are only visible with DAPI or Eub338 probe staining and this is consistent with clone library results indicating that more than 50% of clones were derived from other bacterial species. All images are 1000× magnification except (D) at 3000× and insets that are enlargements equivalent to 3000-5000×.

FISH was performed on vaginal fluid to determine if the bacteria detected by PCR were visible by fluorescence microscopy. Table 1 shows the probes employed and FIG. 3 shows fluorescence micrographs of vaginal fluid from subjects with BV. Thin, curved bacteria hybridizing with the BVAB 1 probe were found at high density in vaginal fluid from subjects with BV whose 16S rDNA clone libraries had significant BVAB 1 representation. The BVAB1 probe did not hybridize with cultivated relatives of BVAB1 in the Clostridium phylum, including *Lachnobacterium bovis* and *Eubacterium ramulus*, demonstrating its specificity. In contrast, under fluorescence microscopy, BVAB 2 appeared to be a short, straight rod that was wider than BVAB 1, while BVAB 3 was a relatively long, wide, straight, lancet shaped rod. Thus, BVAB 1,2, and 3 have distinct morphologies, are easily distinguished from other BV-associated bacteria such as *Atopobium, Mobiluncus*, and *Gardnerella* species, and are found attached to vaginal epithelial cells in a fashion typical of the clue cells that characterize BV.

Molecular analysis of the vaginal bacterial flora demonstrated considerable bacterial diversity in subjects with BV, with 35 bacterial phylotypes detected in the 16 baseline and longitudinal samples from subjects with BV. Sixteen bacterial species detected in subjects with BV appear to be novel based on poor homology with known 16S rDNA sequences in Genbank. Numerous bacterial genera identified in this study have not been previously detected in the vaginal niche using cultivation methods. No single bacterial community was found in all subjects with BV, but common consortia of bacteria were evident. In contrast, subjects without BV had a relatively homogeneous vaginal flora, and bacterial 16S rDNA sequences closely matched known cultivated bacteria in the *Lactobacillus* genus.

Broad range bacterial 16S rDNA PCR. Primers that anneal with highly conserved regions of the bacterial 16S rRNA gene were used in PCRs to amplify approximately 1069 bp segments of this gene from many different bacteria (Table 1). One microliter of sample DNA was added to 49 microliters of a PCR mixture containing 1 unit of Pfu-turbo polymerase, nucleotides, magnesium, and buffer. PCR products were electrophoresed on agarose gels and visualized with ethidium bromide/UV light. PCR products were cloned into *E. coli* using the Zero Blunt TOPO PCR cloning kit (Invitrogen). Digest control DNA was routinely cloned and analyzed to detect any low-level contaminants, despite the absence of detectable bands on agarose gel electrophoresis. One hundred clones from each vaginal fluid sample PCR were picked from culture plates, except for library BV7, where 420 clones were analyzed in order to compare results between a 100-clone and a 420-clone library. Plasmid inserts containing 16S rDNA sequences were PCR amplified from each clone using priming sites located on the vector. These amplification products were electrophoresed on 2% agarose gels to determine if inserts of the correct size were present (i.e., 1 kb). Bacterial 16S rDNA produced by the plasmid PCRs was then subjected to amplified ribosomal DNA restriction analysis (ARDRA). Amplified 16S rDNA from each clone was digested with restriction enzymes HinP1 and HaeIII in separate reactions. DNA from these reactions was electrophoresed on 3% agarose gels and restriction fragment banding patterns were documented for each clone. Clones with unique banding patterns were sequenced to identify individual bacterial 16S rDNA sequences, and the percentage of clones with each 16S rDNA sequence type was determined. Sequence confirmation of ARDRA patterns was performed for every unique pattern in every library of 100 clones. The bacterial 16S rDNA sequences obtained were then aligned with known 16S rDNA sequences in Genbank using the basic local alignment search tool (BLAST) at the National Center for Biotechnology Information, and percent homology scores were generated to identify bacteria. Bacteria with 16S rDNA sequences >98% similar were considered to be the same phylotype and were grouped together (Table 4). Bacterial 16S rDNA sequences were also aligned with near neighbor sequences using the Clustal W program and phylogenetic relationships were inferred using a maximum likelihood algorithm (Phylip package). 16S rDNA sequences for each bacterial phylotype were deposited in Genbank with accession numbers AY724739-AY724742, and AY738656-AY738706. Chimeric sequences were detected using the Check_Chimera program at the Ribosomal Database Project and were excluded from analysis. Beta-globin PCR was performed on all samples to confirm that amplifiable DNA was present and PCR inhibitors absent[31].

Bacterium-specific PCRs. In order to detect bacterial species of particular interest with greater sensitivity than that afforded by broad range 16S rDNA PCR, bacterium-specific 16S rDNA PCR assays were developed. Cloned 16S rDNA sequences were used as positive controls and all assays detected 1-100 molecules. Assay conditions were as previously described, using Taq Gold polymerase[32]. PCR assays were developed for BV-associated bacterium 1, 2, and 3, *Gardnerella vaginalis, Atopobium* sp., *Leptotrichia/Sneathia* sp., *Megasphaera* sp., and *Eggerthella*-like bacterium (Table 3). The identity of amplification products was confirmed by sequencing every reaction with a visible product on gel electrophoresis.

Fluorescence in situ hybridization. For FISH analysis, vaginal fluid smears on glass slides were fixed in 95% ethanol and hybridized with rDNA probes targeting bacterial 16S rRNA, as previously described[33]. Formamide concentrations in the hybridization buffer varied between 10-20%, depending on the melting characteristics of the probes. Probes were labeled with fluorescein, cyanine 3, or cyanine 5 fluorophores. Probe sequences are listed in Table 3. Cells were also stained with 4',6-Diamidino-2-phenylindole (DAPI) that binds to DNA. Bacteria in vaginal fluid smears were visualized using epifluorescence microscopy with a 100× oil immersion objective. Excitation and emission filters appropriate for each fluorophore were used, images were captured with a digital camera, and output was displayed with Meta-Vue (Universal Imaging Corporation) image analysis software. ATCC cultures of *Lachnobacterium bovis, Eubacterium ramulus, E. coli, Gardnerella vaginalis*, and *Mobiluncus curtisii* were used as control bacteria. Probe Eub338 that binds to most bacterial rRNA was used as a positive control probe, and probe Non338 that is a nonsense probe was used as a negative control probe[33].

Example 2

Bacterium-specific PCR results, 264 sample analysis. PCR primers were designed to anneal to species-specific regions of the bacterial 16S rRNA gene (16S rDNA). These novel primers were used in PCR assays capable of detecting 1-100 molecules of cloned 16S rDNA from each bacterium. When amplicons of the correct size were seen on ethidium bromide stained agarose gels, the PCR products were sequenced to confirm identity with the expected bacterial target. Several bacterial species were very sensitive and specific indicators of BV when PCR detection in vaginal fluid was used as the diagnostic test.

Samples from 216 patients at the Women's Research Clinic (WRC) were analyzed according to the Amsel clinical criteria (Table 6) and the Nugent criteria (Table 7). Amsel criteria include the presence of at least 3 of 4 clinical elements, (1) thin, homogeneous, milky, vaginal discharge; (2) vaginal fluid pH greater than 4.5; (3) positive whiff test—production of fishy odor when 10% potassium hydroxide is added to a slide containing vaginal fluid; and (4) presence of clue cells (>20% of epithelial cells with adherent bacteria) on microscopic examination of vaginal fluid (Amsel et al. "Nonspecific vaginitis. Diagnostic criteria and microbial and epidemiologic associations" *Am J Med* 74:14-22 (1983)). Nugent criteria score vaginal fluid smears based on the quantity of *Lactobacillus, Gardnerella* and curved-rod morphotypes seen on gram stain. Subjects without BV have vaginal smears dominated by *Lactobacillus* morphotypes, whereas subjects with BV have vaginal smears dominated by *Gardnerella* and curved rod morphotypes (Nugent et al. "Reliability of diagnosing bacterial vaginosis is improved by a standardized method of gram stain interpretation" *J Clin Microbiol* 29:297-301 (1991); Spiegel et al. "Diagnosis of bacterial vaginosis by direct gram stain of vaginal fluid" *J Clin Microbiol* 18:170-7 (1983).

Samples from 48 patients at an STD clinic in Seattle were analyzed according to Amsel criteria only. Tables 6, 8 and 9 show the results of PCR comparisons of 1) samples from the WRC (Tabulated-WRC (n=216)), 2) samples from the STD clinic (STD Tabulated PCR results), and 3) a combination of the samples from the WRC and the STD clinic (Tabulated—All baseline (WRC+STD)), respectively. In the tables, the results of the PCR assay for each organism listed (PCR+ or PCR−) are shown in the first column, the results of the diagnostic tests carried out at either the WRC or the STD clinic according to the Amsel and/or Nugent criteria (BV+ or BV−) are shown in the second and third columns, the percent of positive PCR samples relative to the diagnostic results from the Amsel and/or Nugent assays (BV+ or BV−) are shown in the fourth and fifth columns, the sensitivity and specificity of each PCR analysis relative to the diagnostic results of the Amsel and/or Nugent assays are shown in the sixth and seventh columns and the Odds Ratio is shown in the last column.

Thus, as one example, by detecting BVAB 2 in a vaginal fluid sample using specific primers in the PCR assay of this invention, of 17 samples identified as positive by the Amsel criteria at the STD clinic, 16 of these samples were also positive by PCR analysis and one of these samples was negative by PCR analysis. Of 31 samples identified as negative by the Amsel criteria at the STD clinic, 3 of these samples were positive by PCR analysis and 28 were negative by PCR analysis. Thus, 94.1% of the Amsel criteria positive samples were PCR positive and 9.7% of the Amsel criteria negative samples were PCR positive, providing a PCR assay for detecting BVAB 2 in a vaginal fluid sample that has 94% sensitivity and 90% specificity in diagnosing bacterial vaginosis. The odds ratio is a measure of effect size. In this case, it is the ratio of the odds of having BV in one group (PCR+) to the odds of having BV in a second group (PCR−).

For instance, *Megaspheara* phylotype 1 was found in 95% of subjects with BV by Amsel criteria (sensitivity), but only 11% of subjects without BV, yielding a specificity of 89%. Similarly, BVAB2, a novel *Clostridium*-like bacterium, was detected by PCR in 86% of subjects with BV by Amsel criteria (sensitivity), but only 7% of subjects without BV, yielding a specificity of 93%. Similar excellent PCR performance was found when Nugent criteria were used as the gold standard for assessing BV.

The potential of combining some PCR assays results for use as a diagnostic test for BV was also examined. For instance, the utility of using a positive *Megasphaera* phylotype 1 PCR OR a positive BVAB2 PCR to define BV was investigated. This combination produced a sensitivity of 99% and a specificity of 89% using Amsel criteria as the gold standard. Using Nugent criteria as the gold standard, this PCR assay combination yielded a sensitivity of 96% and a specificity of 94%. For the PCR "false positives" by Amsel criteria, several of these subjects were positive for BV when Nugent criteria were used. Furthermore, two subjects who were considered false positive by both Amsel and Nugent criteria went on to develop BV in the subsequent weeks after sampling, indicating that these PCR assays may be useful for the early detection of BV (Table 11).

Example 3

Quantitative real time PCR. Vaginal fluid DNA extracted from swabs was added to PCR reactions containing master mix, primers (Table 10), a TaqMan® probe (dual labeled probe for detection with 5'-exonuclease based hydrolysis), and a thermally stable DNA polymerase. Other approaches for real time or endpoint detection of PCR products, such as the use of fluorescence resonance energy transfer (FRET) probes (see, e.g., Loeffler et al. "Quantification of fungal DNA by using fluorescence resonance energy transfer and the light cycler system" *J. Clin. Microbiol.* 38:586-590 (2000)), are also possible using these reagents.

In these experiments, the detection threshold for each assay was assessed using a dilution series of purified plasmids containing bacterial 16S rDNA sequences from specific bacterial species (Table 12) of known concentrations. A standard curve was generated for each assay using a plasmid of cloned 16S rDNA from the appropriate vaginal bacterium, thus assay results are expressed as 16S rDNA copies per swab. All assays have detection thresholds of 1-10 molecules of cloned 16S rDNA. As bacteria have between one and 15 copies of the rRNA operon, depending on species, these assays are capable of detecting DNA from a single bacterium used as template in a PCR and are thus highly sensitive. Cloned plasmids containing 16S rDNA from non-target vaginal bacteria were used to assess the specificity of these bacterium-specific qPCR assays. One million copies of non-target bacterial 16S rDNA representing about 35 vaginal bacteria were added to separate PCRs for each bacterium and validated that the detection thresholds were below the stated assay threshold for a positive result. No non-target bacteria were detected in these specific qPCR assays. There was also excellent concordance between the conventional bacterium-specific PCR results and the qPCR results when used in a positive/negative format (qualitative). The failure to detect a million copies of the non-target sequence while being able to detect 1-10 copies of the target 16S rDNA shows both the analytical sensitivity and the specificity for these assays.

The BVAB2 (novel Clostridium-like bacterium) and *Megasphaera* qPCR assays were applied to vaginal samples from women with and without BV to determine their diagnostic sensitivity and specificity for BV when applied in a qualitative fashion, calling any signal above the detection threshold a positive result. The qPCR assays have sensitivity and specificity comparable to conventional PCR assays described herein. In the present study, *Megasphaera* was found in 97% of subjects with BV and 9.6% of subjects without BV. BVAB-2 was found in 81% of subjects with BV and 6.5% of subjects without BV. Thus, using the *Megasphaera* phylotype 1 (elsdenii-like) qPCR assay to diagnose BV resulted in a sensitivity of 97% and a specificity of 90%. Using the BVAB2 qPCR assay to diagnose BV resulted in a sensitivity of 81% and a specificity of 93.5%. These quantitative PCR assays can be useful for defining threshold levels of vaginal bacteria that correlate with BV.

Example 4

Figure 4:
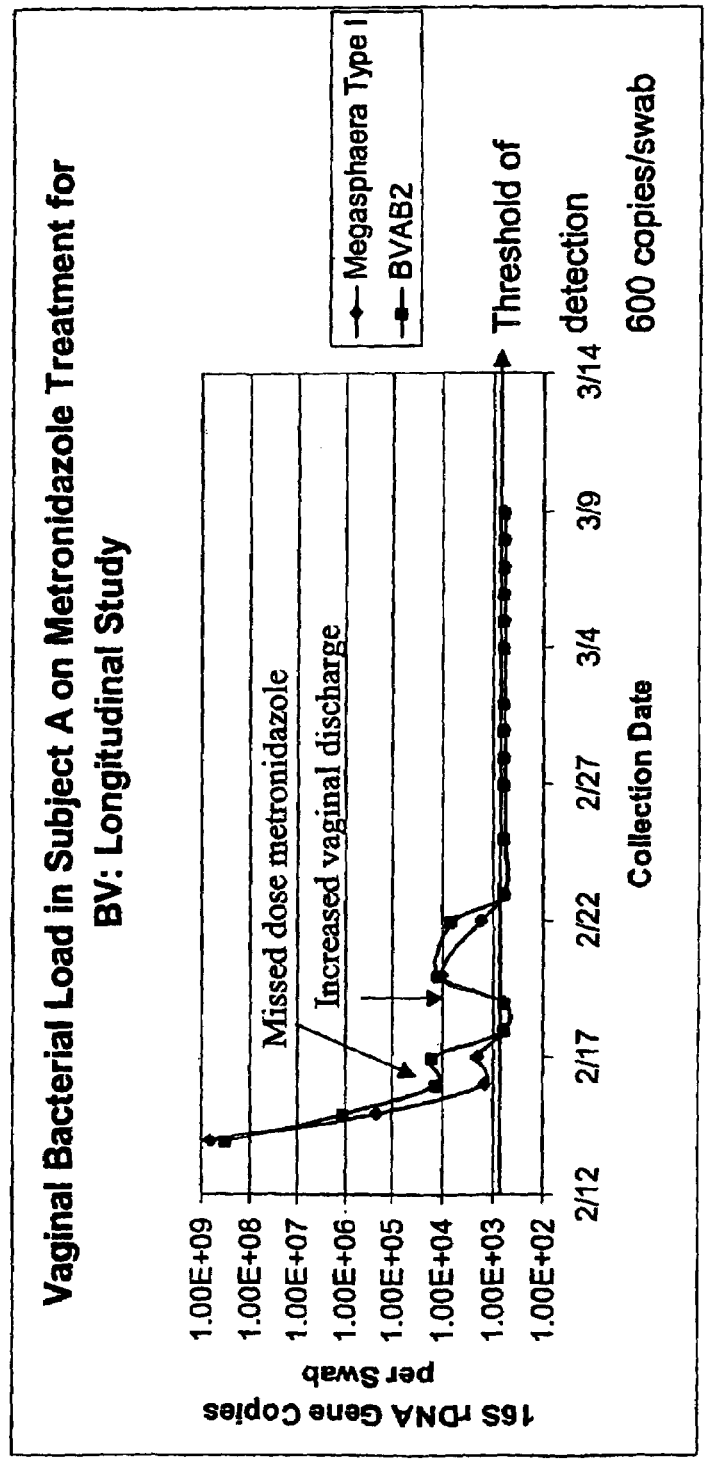
FIG. 4. Results of longitudinal quantitative PCR study of a subject diagnosed with bacterial vaginosis.

Longitudinal study of subject diagnosed with bacterial vaginosis. Daily vaginal swabs were obtained from one subject with bacterial vaginosis. DNA was extracted from the swabs and used in bacterium-specific quantitative real time PCR assays using a TaqMan® PCR platform. The subject was given a prescription for five days of intravaginal metronidazole. Prior to treatment, the subject had very high vaginal bacterial loads, with almost a billion copies of bacterial 16S rDNA form BVAB2 and *Megasphaera* per swab. After one day of intravaginal antibiotic, the bacteria load dropped several orders of magnitude and this continued after a second day of treatment. On her third treatment day, the subject missed a dose of her nightly metronidazole, resulting in an increase in bacterial load. After resuming antibiotic, the bacterial load fell, though the subject also had a late increase in bacterial load corresponding to an increase in symptoms of BV. Clinical cure was associated with eradication of bacteria as assessed by the failure to detect BVAB2 and *Megasphaera* at the 600 copies/swab detection threshold (FIG. 4). These data show that vaginal bacterial loads correlate with response to antibiotic therapy and BV status.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference into this application in order to more fully describe the state of the art to which this invention pertains.

REFERENCES

1. Wang J. Bacterial vaginosis. *Prim. Care Update Ob Gyns* 2000; 7:181-185.
2. Leitich H, Bodner-Adler B, Brunbauer M, Kaider A, Egarter C, Husslein P. Bacterial vaginosis as a risk factor for preterm delivery: a meta-analysis. *Am J Obstet Gynecol* 2003; 189:139-47.
3. Hillier S L, Krohn M A, Cassen E, Easterling T R, Rabe L K, Eschenbach D A. The role of bacterial vaginosis and vaginal bacteria in amniotic fluid infection in women in preterm labor with intact fetal membranes. *Clin Infect Dis* 1995; 20 Suppl 2:S276-8.
4. Peipert J F, Ness R B, Blume J, et al. Clinical predictors of endometritis in women with symptoms and signs of pelvic inflammatory disease. *Am J Obstet Gynecol* 2001; 184: 856-63; discussion 863-4.
5. Hillier S L, Kiviat N B, Hawes S E, et al. Role of bacterial vaginosis-associated microorganisms in endometritis. *Am J Obstet Gynecol* 1996; 175:435-41.
6. Martin H L, Richardson B A, Nyange P M, et al. Vaginal lactobacilli, microbial flora, and risk of human immunodeficiency virus type 1 and sexually transmitted disease acquisition. *J Infect Dis* 1999; 180:1863-8.
7. Moodley P, Connolly C, Sturm A W. Interrelationships among Human Immunodeficiency Virus Type 1 Infection, Bacterial Vaginosis, Trichomoniasis, and the Presence of Yeasts. *J Infect Dis* 2002; 185:69-73.
8. Klebanoff M A, Schwebke J R, Zhang J, Nansel T R, Yu K F, Andrews W W. Vulvovaginal symptoms in women with bacterial vaginosis. *Obstet Gynecol* 2004; 104:267-72.
9. Gardner H L, Dukes C D. Haemophilus vaginalis vaginitis: a newly defined specific infection previously classified "nonspecific" vaginitis. *Am J Obstet Gynecol* 1955; 69:962-76.
10. Spiegel C A, Eschenbach D A, Amsel R, Holmes K K. Curved anaerobic bacteria in bacterial (nonspecific) vaginosis and their response to antimicrobial therapy. *J Infect Dis* 1983; 148:817-22.
11. Spiegel C A. Bacterial vaginosis. *Clin Microbiol Rev* 1991; 4:485-502.
12. Amsel R, Totten P A, Spiegel C A, Chen K C, Eschenbach D, Holmes K K. Nonspecific vaginitis. Diagnostic criteria and microbial and epidemiologic associations. *Am J Med* 1983; 74:14-22.
13. Nugent R P, Krohn M A, Hillier S L. Reliability of diagnosing bacterial vaginosis is improved by a standardized method of gram stain interpretation. *J Clin Microbiol* 1991; 29:297-301.
14. Spiegel C A, Amsel R, Holmes K K. Diagnosis of bacterial vaginosis by direct gram stain of vaginal fluid. *J Clin Microbiol* 1983; 18:170-7.
15. Hugenholtz P, Goebel B M, Pace N R. Impact of culture-independent studies on the emerging phylogenetic view of bacterial diversity. *J Bacteriol* 1998; 180:4765-74.
16. Pace N R. A molecular view of microbial diversity and the biosphere. *Science* 1997; 276:734-40.

17. Hillier S L, Critchlow C W, Stevens C E, et al. Microbiological, epidemiological and clinical correlates of vaginal colonisation by Mobiluncus species. *Genitourin Med* 1991; 67:26-31.
18. Hallen A, Pahlson C, Forsum U. Bacterial vaginosis in women attending STD clinic: diagnostic criteria and prevalence of Mobiluncus spp. *Genitourin Med* 1987; 63:386-9.
19. Berger B J, Kolton S, Zenilman J M, Cummings M C, Feldman J, McCormack W M. Bacterial vaginosis in lesbians: a sexually transmitted disease. *Clin Infect Dis* 1995; 21:1402-5.
20. Marrazzo J M, Koutsky L A, Eschenbach D A, Agnew K, Stine K, Hillier S L. Characterization of vaginal flora and bacterial vaginosis in women who have sex with women. *J Infect Dis* 2002; 185:1307-13.
21. Sexually transmitted diseases treatment guidelines 2002. Centers for Disease Control and Prevention. *MMWR Recomm Rep* 2002; 51:1-78.
22. Sobel J D. Bacterial vaginosis—an ecologic mystery. *Ann Intern Med* 1989; 111:551-3.
23. Fredricks D N, Relman D A. Sequence-based identification of microbial pathogens: a reconsideration of Koch's postulates. *Clin Microbiol Rev* 1996; 9:18-33.
24. Burton J P, Devillard E, Cadieux P A, Hammond J A, Reid G. Detection of Atopobium vaginae in postmenopausal women by cultivation-independent methods warrants further investigation. *J Clin Microbiol* 2004; 42:1829-31.
25. Ferris M J, Masztal A, Aldridge K E, Fortenberry J D, Fidel P L, Jr., Martin D H. Association of Atopobium vaginae, a recently described metronidazole resistant anaerobe, with bacterial vaginosis. *BMC Infect Dis* 2004; 4:5.
26. Verhelst R, Verstraelen H, Claeys G, et al. Cloning of 16S rRNA genes amplified from normal and disturbed vaginal microflora suggests a strong association between *Atopobium vaginae, Gardnerella vaginalis* and bacterial vaginosis. *BMC Microbiol* 2004; 4:16.
27. Zhou X, Bent S J, Schneider M G, Davis C C, Islam M R, Forney L J. Characterization of vaginal microbial communities in adult healthy women using cultivation-independent methods. *Microbiology* 2004; 150:2565-73.
28. Hillier S L, Krohn M A, Nugent R P, Gibbs R S. Characteristics of three vaginal flora patterns assessed by gram stain among pregnant women. Vaginal Infections and Prematurity Study Group. *Am J Obstet Gynecol* 1992; 166: 938-44.
29. Hill G B, Livengood C H, 3rd. Bacterial vaginosis-associated microflora and effects of topical intravaginal clindamycin. *Am J Obstet Gynecol* 1994; 171:1198-204.
30. Puapermpoonsiri S, Kato N, Watanabe K, Ueno K, Chongsomchai C, Lumbiganon P. Vaginal microflora associated with bacterial vaginosis in Japanese and Thai pregnant women. *Clin Infect Dis* 1996; 23:748-52.
31. Fredricks D N, Relman D A. Paraffin removal from tissue sections for digestion and PCR analysis. *Biotechniques* 1999; 26:198-200.
32. Fredricks D N, Relman D A. Improved amplification of microbial DNA from blood cultures by removal of the PCR inhibitor sodium polyanetholesulfonate. *J Clin Microbiol* 1998; 36:2810-6.
33. Fredricks D N, Relman D A. Localization of *Tropheryma whippelii* rRNA in tissues from patients with Whipple's disease. *J Infect Dis* 2001; 183:1229-37.

TABLE 1

Primers used for PCR and labeled oligonucleotide probes used for FISH. Fluorophores used to label probes: Cy5 is Cyanine 5 dye, Cy3 is Cyanine 3 dye, and Fl is fluorescein. All FISH assays were performed at 45° C. with the effective melting temperature of probes adjusted with formamide.

| Bacteria | Oligo | Sequence | Annealing Temp. | Cycle Number |
|---|---|---|---|---|
| PCR assay Broad range bacteria | Primer Bact-338F | 5'-ACTCCTRCGGGAGGCAGCAG-3' (SEQ ID NO:1) | 55° C. | 21-25 |
| | Bact-1407R | 5'-GACGGGCGGTGWGTRCA-3' (SEQ ID NO:2) | | |
| BVAB 1 | (Uncxb1-649F) BVAB1-1019F | 5'-GTATATTTTCTACGGAACACAGG-3' (SEQ ID NO:3) | 55° C. | 40 |
| | (Uncxb1-908R) BVAB1-1280R | 5'-TTTGCTCCGGATCGCTCCTT-3' (SEQ ID NO:4) | | |
| BVAB 2 | (Uncxb2-619F) BVAB2-619F | 5'-TTAACCTTGGGGTTCATTACAA-3' (SEQ ID NO:5) | 55° C. | 40 |
| | (Uncxb2-1023R) BVAB2-1024R | 5'-AATTCAGTCTCCTGAATCGTCAGA-3' (SEQ ID NO:6) | | |
| BVAB 3 | (Uncxb3-1000F) BVAB3-999F | 5'-CTTGAWCGATGTAGAGATACATAA-3' (SEQ ID NO:7) | 55° C. | 40 |
| | (Uncxb3-1278R) BVAB3-1278R | 5'-TGCTTCGCCTCGCGACGTC-3' (SEQ ID NO:8) | | |
| *Gardnerella vaginalis* | (G. vag 643F) G. vag 644F | 5'-GGGCGGGCTAGAGTGCA-3' (SEQ ID NO:9) | 62° C. | 40 |
| | (G. vag 846R) G. vag 851R | 5'-GAACCCGTGGAATGGGCC-3' (SEQ ID NO:10) | | |

TABLE 1-continued

Primers used for PCR and labeled oligonucleotide probes used for FISH.
Fluorophores used to label probes: Cy5 is Cyanine 5 dye, Cy3 is Cyanine
3 dye, and Fl is fluorescein. All FISH assays were performed at
45° C. with the effective melting temperature of probes adjusted
with formamide.

| Bacteria | Oligo | Sequence | Annealing Temp. | Cycle Number |
|---|---|---|---|---|
| *Atopobium* sp. | (Ato-441F) Atop-442F (Ato-1016R) Atop-1017R | 5'-GCAGGGACGAGGCCGCAA-3' (SEQ ID NO:11) 5'-GTGTTTCCACTGCTTCACCTAA-3' (SEQ ID NO:12) | 55° C. | 40 |
| *Eggerthella*-like uncultured bacterium | (Egger-620F) Egger-621F (Egger-854R) Egger-859R | 5'-AACCTCGAGCCGGGTTCC-3' (SEQ ID NO:13) 5'-TCGGCACGGAAGATGTAATCT-3' (SEQ ID NO:14) | 55° C. | 40 |
| *Leptotrichia* sp. | (Lepto-394F) Lepto-395F (Lepto-645R) Lepto-646R | 5'CAATTCTGTGTGTGTGAAGAAG-3' (SEQ ID NO:15) 5'-ACAGTTTTGTAGGCAAGCCTAT-3' (SEQ ID NO:16) | 55° C. | 40 |
| Megasphaera Type II | MegaM-453F MegaM-666R | 5'-AAGGTGGTAAATAGCCATCATGAG-3' (SEQ ID NO:17) 5'-CTCTCCGACACTCAAGTCTTC-3' (SEQ ID NO:18) | 57° C. | 40 |
| Megasphaera Type I | (MegaE-458F) MegaE-456F (MegaE-666R) MegaE-667R | 5'-GATGCCAACAGTATCCGTCCG-3 (SEQ ID NQ:19) 5'-CCTCTCCGACACTCAAGTTCGA-3' (SEQ ID NO:20) | 55° C. | 40 |
| BVAB-TM7 | TM7-641F TM7-1020R | 5'-AACTGCTTGGCTCGAGATTATC-3' (SEQ ID NO:21) 5'-TCTCCTTTCGGAGAAATTCTAGG-3' (SEQ ID NO:22) | 53° C. | 45 |
| *Peptoniphilus lacrimalis* | P. lacri-999F Pepton-1184R | 5'-AAGAGACGAACTTAGAGATAAGTTTT-3' (SEQ ID NO:23) 5'-CACCTTCCTCCGATTTATCATC-3' (SEQ ID NO:24) | 55° C. | 40 |
| *Peptoniphilus* sp. | Pepton-1003F Pepton-1184R | 5'-GACCGGTATAGAGATATACCCT-3' (SEQ ID NO:25) 5'-CACCTTCCTCCGATTTATCATC-3' (SEQ ID NO:24) | 55° C. | 40 |
| *Mobiluncus curtisii* | M. curt-440F M. curt-1026R | 5'-TTCTCGCGAAAAAGGCACAG-3' (SEQ ID NO:26) 5'-CTGGCCCATCTCTGGAACCA-3' (SEQ ID NO:27) | 57° C. | 40 |
| *Mobiluncus mulieris* | Mobil-577F M. mulie-1026R | 5'-GCTCGTAGGTGGTTCGTCGC-3' (SEQ ID NO:28) 5'-CCACACCATCTCTGGCATG-3' (SEQ ID NO:29) | 62° C. | 40 |
| Prevotella G1 | PrevG1-468F PrevG1-857R | 5'-GTCCCTTATTGCATGTACCATAC-3' (SEQ ID NO:30) 5'-GCCGCTAACACTAGGTGCTA-3' (SEQ ID NO:31) | 55° C. | 40 |
| Prevotella G2 | PrevG2-648F PrevG2-871R | 5'-CGACTTGAGTATGCAGGAAGT-3' (SEQ ID NO:32) 5'-AATGTTTTCACTTGGCCACTCATC-3' (SEQ ID NO:33) | 55° C. | 40 |
| *Lactobacillus crispatus* | L. crisp-452F L. crisp-1023R | 5'-GATAGAGGTAGTAACTGGCCTTTA-3' (SEQ ID NO:34) 5'-CTTTGTATCTCTACAAATGGCACTA-3' (SEQ ID NO:35) | 54° C. | 45 |

TABLE 1-continued

Primers used for PCR and labeled oligonucleotide probes used for FISH. Fluorophores used to label probes: Cy5 is Cyanine 5 dye, Cy3 is Cyanine 3 dye, and Fl is fluorescein. All FISH assays were performed at 45° C. with the effective melting temperature of probes adjusted with formamide.

| Bacteria | Oligo | Sequence | Annealing Temp. | Cycle Number |
|---|---|---|---|---|
| Lactobacillus iners | L. iners-453F | 5'-ACAGGGGTAGTAACTGACCTTTG-'3 (SEQ ID NO:36) | 55° C. | 40 |
|  | L. iners-1022R | 5'-ATCTAATCTCTTAGACTGGCTATG-3' (SEQ ID NO:37) |  |  |
| Beta-globin | GH20 | 5'-GAAGAGCCAAGGACAGGTAC-3' (SEQ ID NO:38) | 55° C. | 40 |
|  | PC04 | 5'-CAACTTCATCCACGTTCACC-3' (SEQ ID NO:39) |  |  |
| FISH assay Broad range bacteria | Probe Eub-338-Cy5 | 5'-GCTGCCTCCCGTAGGAGT-Cy5-3' (SEQ ID NO:40) | 45° C. |  |
| Negative Control | Non-338-Cy5 | 5'-ACTCCTACGGGAGGCAGC-Cy3-5' (SEQ ID NO:41) | 45° C. |  |
| BVAB 1 | Uncxb1-134-Fl | 5'-CTGCTATCCCCCCGGTACAGG-Fl-3' (SEQ ID NO:42) | 45° C. |  |
| BVAB 2 | Uncxb2-1244-Cy3 | 5'-CCCTCTTGCTTCCCTCTGTCACA-Cy3-3' (SEQ ID NO:43) | 45° C. |  |
| BVAB 3 | Uncxb3-1244-Cy3 | 5'-CGACGTCGCTGCTCTCTGTTGTA-Cy3-3' (SEQ ID NO:44) | 45° C. |  |
| Mobiluncus | Mobil-125-Cy3 | 5'-TCCCAAAGAAAAGGACAGGTTACTC-Cy3-3' (SEQ ID NO:45) | 45° C. |  |
| Gardnerella | G. vag-200-Cy3 | 5'-CCACTAAACACTTTCCCAACAAGA-Cy3-3' (SEQ ID NO:46) | 45° C. |  |
| Atopobium | Ato-291-Cy3 | 5'-GGTCGGTCTCTCAACCC-Cy3-3' (SEQ ID NO:47) | 45° C. |  |

TABLE 2

Characteristics of Subjects, According to the Presence of Bacterial Vaginosis (BV)

|  | BV present N = 27 | BV absent N = 46 |
|---|---|---|
| Site of enrollment - no. (%) |  |  |
| Sexually Transmitted Disease Clinic | 8 (29.6) | 6 (13.0) |
| Research Clinic | 19 (70.4) | 40 (87.0) |
| Age - yr. |  |  |
| Median | 25 | 24 |
| Range | 20–42 | 18–38 |
| White race - no. (%) | 16 (59.3) | 40 (87.0) |
| Male sex partners, prior 60 days* |  |  |
| Median no. | 1 | 1 |
| Range | 1–4 | 1–4 |
| Female sex partners, prior 60 days |  |  |
| Median no. | 1 | 1 |
| Range | 1–2 | 1–3 |
| Sex with men, prior 3 months - no. (%) | 12 (44.4) | 38 (82.6) |
| Sex with women, prior 3 months - no. (%) | 19 (70.3) | 40 (87.0) |
| Vaginal symptoms† present - no (%) | 15 (55.6) | 12 (26.1) |
| Concurrent genitourinary infection present - no (%) |  |  |
| Vulvovaginal candidiasis | 0 (0) | 4 (8.7) |
| Trichomoniasis | 0 (0) | 0 (0) |
| Chlamydia trachomatis | 2 (7.4) | 0 (0) |

*Among subjects who reported these behaviors
†Defined as increased or malodorous vaginal discharge.
Race is self-reported.

TABLE 3

Identification of bacteria in vaginal fluid by broad range 16S rDNA PCR for subjects with BV, without BV (controls), and with changing clinical status (longitudinal study). The percentage of clones from each bacterial 16S rDNA phylotype or species (row) is displayed for each sample library (column). For sequences with less than 98% similarity to known 16S rDNA sequences, the percent similarity to the closest match in GenBank is listed along with the GenBank accession number for that most similar sequence. Apart from colonization with *C. vaginalis* and *Lactobacillus iners*, there was little overlap between the bacteria detected in subjects with BV and without BV. Numerous novel bacterial species were detected in subjects with BV.

| | Bacterial vaginosis | | | | | | | | | Controls | | | | |
|---|---|---|---|---|---|---|---|---|---|---|---|---|---|---|
| | Subject | | | | | | | | | | | | | |
| Broad Range 16S rDNA PCR Clones | BV1 | BV2 | BV3 | BV4 | BV5 | BV6 | BV7 | BV8 | BV9 | C1 | C2 | C3 | C4 | C5 |
| 16 S Bacterial rDNA sequence | | | | | | | | | | | | | | |
| *Lactobacillus crispatus* | | | | | | | | | | 49% | 74% | 99% | 48% | 60% |
| *Lactobacillus jensenii* | | | | | | | | | | | | | 2% | |
| *Lactobacillus gallinarum* | | | | | | | | | | 13% | | | | |
| *Lactobacillus gasseri* | | | | | | | | | | | 9% | | | 1% |
| *Lactobacillus vaginalis* | | | | | | | | | | | | | 2% | |
| *Staphylococcus epidermidis* | | | | | | | | | | | 2% | | | |
| *Staphylococcus lugdunensis* | | | | | | | | | | | | | 1% | |
| *Clostridium perfringens* 96% AB045286 | | | | | | | | | | | | | | 3% |
| *Ureaplasma parvum* | | | | | | | | | | | 1% | | | |
| *Lactobacillus iners* | | | | 7% | 22% | 3% | | 1% | 5% | 38% | | 1% | 46% | 36% |
| *Gardnerella vaginalis* | 35% | 13% | 2% | 4% | 28% | 1% | 25% | 31% | 39% | | 14% | | | |
| uncultured AB034121 90.6% (BVAB 1) | | 43% | 66% | 34% | | 36% | 17% | | 26% | | | | | |
| uncultured AF407407 90.9% (BVAB 2) | 10% | 4% | | 10% | 3% | 5% | 4% | | 4% | | | | | |
| uncultured ULO278163 92.9% (BVAB 3) | 1% | 1% | | | | | 1% | | | | | | | |
| *Atopobium vaginae* | 5% | | 3% | 21% | 1% | 3% | 3% | 11% | 11% | | | | | |
| *Leptotrichia amnionii* | 6% | | 2% | 8% | 1% | 3% | 10% | 10% | | | | | | |
| *Megasphaera elsdenii* 93.8% AY038994 | 4% | 10% | 7% | 1% | 18% | 3% | 2% | 13% | 6% | | | | | |
| *Megasphaera micronuciformis* 94.6% AF473833 | | | | | | | 1% | | | | | | | |
| *Eggerthella hongkongensis* 91.8% AY288517 | 2% | 2% | 2% | 1% | 4% | 1% | 3% | 8% | | | | | | |
| *Porphyromonas asaccharolytica* | | | | 2% | | 5% | | | | | | | | |
| *Dialister* sp (α) | 1% | 1% | 2% | 2% | | | | | | | | | 1% | |
| *Dialister* sp (β) 94.8% AF371693 | | 1% | 2% | | | 2% | 2% | 1% | | | | | | |
| *Sneathia sanguinegens* | 3% | | 2% | | 16% | 9% | 9% | | | | | | | |
| *Prevotella* geno group 1 | 21% | 24% | | 1% | 7% | 9% | 12% | 20% | | | | | | |
| *Prevotella* geno group 2 | 7% | | | 4% | | 6% | 7% | | 1% | | | | | |
| *Prevotella* geno group 3 | | | 7% | | | | | 3% | | | | | | |
| *Prevotella bivia* | | | | | | | | | | | | | | |
| *Prevotella buccalis* | | | | | | | | 6% | | | | | | |
| *Prevotella dentalis* 93.2% X81876 | | | | | | 2% | 2% | | | | | | | |
| *Prevotella disiens* | | | | | | | | | | | | | | |
| *Prevotella oulora* 90.6% L16472 | | | | | | | | | | | | | | |
| *Prevotella shahii* 90.7% AB108825 | | | | | | | | | | | | | | |
| uncultured 4C28d-23 91.2% AB034149 | 1% | | 3% | 1% | | 2% | | | | | | | | |
| *Candidate* TM7 93.7% AF125206 | | | 2% | 2% | | 8% | | | | | | | | |
| *Mobiluncus mulieris* | | | | | | | | | | | | | | |
| *Peptoniphilus lacrimalis* | | | | | | | 1% | | | | | | | |
| *Peptoniphilus* sp. | | 1% | | | | 2% | | | | | | | | |
| *Peptstreptococcus micros* 97.8% AF542231 | 3% | | 2% | | | | 1% | | | | | | | |
| *Gemella bergeriae* 95.8% Y13365 | 1% | | | | | | | | | | | | | |
| *Aerococcus* sp. | | | | | | | 1% | 2% | | | | | | |
| *Anaerococcus tetradius* | | | | | | | | | | | | | | |
| uncultured AF371910 89.8% | | | | | | | | | | | | | | |
| uncultured AJ400235 88.4% | | | | | | | | | | | | | | |
| *Veillonella* sp. | | | | | | | 1% | | | | | | | |

| | | | | Longitudinal | | | | | | | | | |
|---|---|---|---|---|---|---|---|---|---|---|---|---|---|
| | | | | Incident | | | Cured | | Relapsed | | | Persistent | | |
| | | | | BV− | BV− | BV+ | BV+ | BV− | BV+ | BV− | BV+ | BV+ | BV+ | BV+ |
| | | | | Day Number | | | | | | | | | | |
| | | | | 0 | 28 | 52 | 0 | 30 | 0 | 28 | 100 | 0 | 34 | 64 |
| | Controls | | | Subject | | | | | | | | | | |
| Broad Range 16S rDNA PCR Clones | C6 | C7 | C8 | L1a | L1b | L1c | L2a | L2b | L3a | L3b | L3c | L4a | L4b | L4c |
| 16 S Bacterial rDNA sequence | | | | | | | | | | | | | | |
| *Lactobacillus crispatus* | 89% | 40% | 100% | 89% | 99% | | 99% | | | | | | | |
| *Lactobacillus jensenii* | 1% | | | 1% | | | | | | | | | | |
| *Lactobacillus gallinarum* | | | | | | | | | | | | | | |
| *Lactobacillus gasseri* | | | | | | | | | | | | | | |
| *Lactobacillus vaginalis* | | | | | | | | | | | | 2% | | |

TABLE 3-continued

Identification of bacteria in vaginal fluid by broad range 16S rDNA PCR for subjects with BV, without BV (controls), and with changing clinical status (longitudinal study). The percentage of clones from each bacterial 16S rDNA phylotype or species (row) is displayed for each sample library (column). For sequences with less than 98% similarity to known 16S rDNA sequences, the percent similarity to the closest match in GenBank is listed along with the GenBank accession number for that most similar sequence. Apart from colonization with C. vaginalis and Lactobacillus iners, there was little overlap between the bacteria detected in subjects with BV and without BV. Numerous novel bacterial species were detected in subjects with BV.

| | 1 | 2 | 3 | 4 | 5 | 6 | 7 | 8 | 9 | 10 | 11 | 12 | 13 |
|---|---|---|---|---|---|---|---|---|---|---|---|---|---|
| *Staphylococcus epidermidis* | | | | | | | | | | | | | |
| *Staphylococcus lugdunensis* | | | | | | | | | | | | | |
| *Clostridium perfringens* 96% AB045286 | | | | | | | | | | | | | |
| *Ureaplasma parvum* | | | | | | | | 3% | | | | | |
| *Lactobacillus iners* | 10% | 60% | 10% | 1% | 7% | | 1% | 1% | 95% | | 2% | | 7% |
| *Gardnerella vaginalis* | | | | | 44% | 43% | | 34% | | 13% | 33% | 12% | 49% |
| uncultured AB034121 90.6% (BVAB 1) | | | | | | | | | | | 11% | 16% | |
| uncultured AF407407 90.9% (BVAB 2) | | | | | | 14% | | 10% | | | 5% | 1% | |
| uncultured ULO278163 92.9% (BVAB 3) | | | | 1% | | | | | | | 1% | | 3% |
| *Atopobium vaginae* | | | | | 6% | 9% | | 16% | | 6% | 11% | 2% | 8% |
| *Leptotrichia amnionii* | | | | | 6% | 2% | | 6% | | | 7% | 14% | 11% |
| *Megasphaera elsdenii* 93.8% AY038994 | | | | | 5% | 3% | | 8% | | 11% | 1% | 1% | |
| *Megasphaera micronuciformis* 94.6% AF473833 | | | | | | | | | | | | | |
| *Eggerthella hongkongensis* 91.8% AY288517 | | | | | 3% | 1% | | 3% | | | | 2% | 1% |
| *Porphyromonas asaccharolytica* | | | | | 1% | 2% | | 3% | | 63% | | 5% | 4% |
| *Dialister* sp (α) | | | | | 2% | 2% | | 3% | | 1% | | 1% | 1% |
| *Dialister* sp (β) 94.8% AF371693 | | | | | 1% | 1% | | | | | 1% | 1% | 1% |
| *Sneathia sanguinegens* | | | | | | | | | | | 1% | 6% | |
| *Prevotella* geno group 1 | | | | | 18% | | | | | | 5% | 12% | 12% |
| *Prevotella* geno group 2 | | | | | 11% | 6% | | 7% | | 5% | 9% | | 1% |
| *Prevotella* geno group 3 | | | | | | | | | | | 2% | 4% | |
| *Prevotella bivia* | | | | | | 2% | | 1% | | 1% | | 2% | |
| *Prevotella buccalis* | | | | | | 7% | | 6% | | | | | |
| *Prevotella dentalis* 93.2% X81876 | | | | | | | | | | | | | |
| *Prevotella disiens* | | | | | | | | | | | 10% | | |
| *Prevotella oulora* 90.6% L16472 | | | | | | | | | | | | | 1% |
| *Prevotella shahii* 90.7% AB108825 | | | | | | | | | | | | | 1% |
| uncultured 4C28d-23 91.2% AB034149 | | | | | 2% | 1% | | | | | 6% | | 1% |
| Candidate TM7 93.7% AF125206 | | | | | | | | | | | 1% | | |
| *Mobiluncus mulieris* | | | | | | | | | | | | 1% | |
| *Peptoniphilus lacrimalis* | | | | | | | | | | | 2% | 2% | |
| *Peptoniphilus* sp. | | | | | | | | | | | 2% | | |
| *Peptstreptococcus micros* 97.8% AF542231 | | | | | | | | | | | | 3% | |
| *Gemella bergeriae* 95.8% Y13365 | | | | | | | | | 1% | | | | |
| *Aerococcus* sp. | | | | | | | | | 1% | | | 1% | |
| *Anaerococcus tetradius* | | | | | | | | | | | | | 1% |
| uncultured AF371910 89.8% | | | | | | | | | | | 1% | | |
| uncultured AJ400235 88.4% | | | | | | | | | | | | | 1% |
| *Veillonella* sp. | | | | | | | | | | | | | |

TABLE 4

Bacterium-specific PCR assay results are presented for 27 baseline vaginal fluid samples from subjects with BV and 46 samples from subjects without BV, with odds ratios and exact 95% confidence intervals unadjusted and adjusted for subject age, site of clinic enrollment, report of abnormal vaginal discharge, and report of sex with men and sensitivity and specificity with exact 95% confidence intervals. Bacterial Vaginosis Associated Bacterium (BVAB) 1, 2, and 3, *Leptotrichia* species, and the combination of BVAB 1 and BVAB 3 were very specific indicators of BV. BVAB 2 and *Leptotrichia* were also found in a high percentage of subjects with disease. *Atopobium* species, an *Eggerthella*-like bacterium, and *Megasphaera* were found in most subjects with BV and few subjects without BV. The presence of *G. vaginalis* in vaginal fluid by PCR was a highly sensitive indicator of BV but had poor specificity; in contrast, the presence of either BVAB2 or *Megasphaera* α maximized sensitivity for presence of BV while retaining high specificity.

| Bacterium-specific PCR Result | | BV Present N = 27 | BV Absent N = 46 | Sensitivity (95% CI) | Specificity (95% CI) | Unadjusted odds ratio (95% CI) | Adjusted odds ratio (95% CI) |
|---|---|---|---|---|---|---|---|
| BVAB 1 | Yes | 11 | 1 | 40.7 (22.4–61.2) | 97.8 (88.5–99.9) | 30.9 (3.8–1359.9) | 19.0 (2.2–910.7) |
| | No | 16 | 45 | | | | |
| BVAB 2 | Yes | 24 | 2 | 88.9 (70.8–97.6) | 95.7 (85.2–99.5) | 176.0 (22.8–1862.8) | 106.1 (14.3–4755.1) |
| | No | 3 | 44 | | | | |
| BVAB 3 | Yes | 11 | 1 | 40.7 (22.4–61.2) | 97.8 (88.5–99.9) | 30.9 (3.8–1359.9) | 21.9 (2.5–1056.4) |
| | No | 16 | 45 | | | | |
| *Gardnerella* | Yes | 27 | 27 | 100.0 (89.5–100.0) | 41.3 (27.0–56.8) | ∞ (5.2–∞) | 27.7 (3.9–∞) |
| | No | 0 | 19 | | | | |
| *Atopobium* sp. | Yes | 26 | 9 | 96.3 (81.0–99.9) | 80.4 (66.1–90.6) | 106.9 (12.9–4493.6) | 95.0 (14.6–∞) |
| | No | 1 | 37 | | | | |

TABLE 4-continued

Bacterium-specific PCR assay results are presented for 27 baseline vaginal fluid samples from subjects with BV and 46 samples from subjects without BV, with odds ratios and exact 95% confidence intervals unadjusted and adjusted for subject age, site of clinic enrollment, report of abnormal vaginal discharge, and report of sex with men and sensitivity and specificity with exact 95% confidence intervals. Bacterial Vaginosis Associated Bacterium (BVAB) 1, 2, and 3, *Leptotrichia* species, and the combination of BVAB 1 and BVAB 3 were very specific indicators of BV. BVAB 2 and *Leptotrichia* were also found in a high percentage of subjects with disease. *Atopobium* species, an *Eggerthella*-like bacterium, and *Megasphaera* were found in most subjects with BV and few subjects without BV. The presence of *G. vaginalis* in vaginal fluid by PCR was a highly sensitive indicator of BV but had poor specificity; in contrast, the presence of either BVAB2 or *Megasphaera* α maximized sensitivity for presence of BV while retaining high specificity.

| Bacterium-specific PCR Result | | BV Present N = 27 | BV Absent N = 46 | Sensitivity (95% CI) | Specificity (95% CI) | Unadjusted odds ratio (95% CI) | Adjusted odds ratio (95% CI) |
|---|---|---|---|---|---|---|---|
| *Eggerthella*-like uncultured bact. | Yes | 25 | 4 | 92.6 (75.7–99.1) | 91.3 (79.2–97.6) | 131.3 (19.0–1323.6) | 103.8 (13.5–4812.8) |
| | No | 2 | 42 | | | | |
| *Leptotrichia* sp. | Yes | 23 | 2 | 85.2 (70.8–97.6) | 95.7 (85.2–99.5) | 126.5 (18.3–1279.6) | 330.6 (23.1–∞) |
| | No | 4 | 44 | | | | |
| *Megasphaera*-α | Yes | 26 | 4 | 96.3 (81.0–99.9) | 91.3 (79.2–97.6) | 273.0 (26.6–11428.3) | 134.4 (16.6–6509.8) |
| | No | 1 | 42 | | | | |
| BVAB1 and BVAB3 | Yes | 9 | 0 | 33.3 (16.5–54.0) | 100.0 (93.7–100.0) | ∞ (5.7–∞) | 24.7 (3.2–∞) |
| | No | 18 | 46 | | | | |
| BVAB2 or *Megasphaera* α | Yes | 27 | 4 | 100.0 (89.5–100.0) | 91.3 (79.2–97.6) | ∞ (57.2–∞) | 190.1 (28.3–∞) |
| | No | 0 | 42 | | | | |

TABLE 5

Table of GenBank Sequences.

| Locus/ Accession No. | Length/Type | Species | Definition | SEQ ID NO: |
|---|---|---|---|---|
| AY738656 | 1000 bp DNA linear | *Eggerthella*-like | Uncultured *Eggerthella* sp. clone 123-f2 68 16S ribosomal RNA gene, partial sequence. | 48 |
| AY738657 | 1008 bp DNA linear | *Atopobium vaginae* α | Uncultured *Atopobium* sp. clone 127-b 4 16S ribosomal RNA gene, partial sequence. | 49 |
| AY738658 | 1008 bp DNA linear | *Atopobium vaginae* β | Uncultured *Atopobium* sp. clone 123-f 36 16S ribosomal RNA gene, partial sequence. | 50 |
| AY738659 | 1009 bp DNA linear | *Sneathia sanguinegens* | Uncultured *Sneathia* sp. clone 123-f 47 16S ribosomal RNA gene, partial sequence. | 51 |
| AY738660 | 1034 bp DNA linear | *Lactobacillus jensenii* | Uncultured *Lactobacillus* sp. clone vag4-103 16S ribosomal RNA gene, partial sequence. | 52 |
| AY738661 | 1038 bp DNA linear | *Dialister* sp β | Uncultured *Dialister* sp. clone 123-b 15 16S ribosomal RNA gene, partial sequence | 53 |
| AY738662 | 1037 bp DNA linear | *Dialister* sp α | Uncultured *Dialister* sp. clone 127-Q 46 16S ribosomal RNA gene, partial sequence. | 54 |
| AY738663 | 1033 bp DNA linear | *Lactobacillus crispatus* α | Uncultured *Lactobacillus* sp. clone vag1-10 16S ribosomal RNA gene, partial sequence. | 55 |
| AY738664 | 1033 bp DNA linear | *Lactobacillus crispatus* β | Uncultured *Lactobacillus* sp. clone vag1-50 16S ribosomal RNA gene, partial sequence. | 56 |
| AY738665 | 1018 bp DNA linear | *Gardnerella vaginalis* Type 1 | Uncultured *Gardnerella* sp. clone 123-b 2 16S ribosomal RNA gene, partial sequence. | 57 |
| AY738666 | 1019 bp DNA linear | *Gardnerella vaginalis* Type 2 | Uncultured *Gardnerella* sp. clone BV8-3 16S ribosomal RNA gene, partial sequence. | 58 |
| AY738667 | 1018 bp DNA linear | *Gardnerella vaginalis* Type 4 | Uncultured *Gardnerella* sp. clone BV6-77 16S ribosomal RNA gene, partial sequence. | 59 |
| AY738668 | 1018 bp DNA linear | *Gardnerella vaginalis* Type 5 | Uncultured *Gardnerella* sp. clone 127-b 3 16S ribosomal RNA gene, partial sequence | 60 |
| AY738669 | 1033 bp DNA linear | *Lactobacillus iners* | Uncultured *Lactobacillus* sp. clone BV5-12 16S ribosomal RNA gene, partial sequence. | 61 |
| AY738670 | 1033 bp DNA linear | *Lactobacillus gasseri* Type 1 | Uncultured *Lactobacillus* sp. clone vag2-70 16S ribosomal RNA gene, partial sequence | 62 |
| AY738671 | 1033 bp DNA linear | *Lactobacillus gasseri* Type 2 | Uncultured *Lactobacillus* sp. clone vag2-24 16S ribosomal RNA gene, partial sequence. | 63 |
| AY738672 | 1038 bp DNA linear | *Megasphaera* sp Type 1 | Uncultured *Megasphaera* sp. clone 127-Q 35 16S ribosomal RNA gene, partial sequence. | 64 |
| AY738673 | 1027 bp DNA linear | *Porphyromonas asaccharolytica* Type 1 | Uncultured *Porphyromonas* sp. clone 127-Q 58 16S ribosomal RNA gene, partial sequence. | 65 |
| AY738674 | 1027 bp DNA linear | *Porphyromonas asaccharolytica* Type 2 | Uncultured *Porphyromonas* sp. clone 123-f 45 16S ribosomal RNA gene, partial sequence. | 66 |
| AY738675 | 1023 bp DNA linear | *Prevotella bivia* | Uncultured *Prevotella* sp. clone 127-Q 23 16S ribosomal RNA gene, partial sequence. | 67 |
| AY738676 | 1025 bp DNA linear | *Prevotella* genogroup 1A | Uncultured *Prevotella* sp. clone 123-f 21 16S ribosomal RNA gene, partial sequence. | 68 |

TABLE 5-continued

Table of GenBank Sequences.

| Locus/ Accession No. | Length/Type | Species | Definition | SEQ ID NO: |
|---|---|---|---|---|
| AY738677 | 1025 bp DNA linear | *Prevotella* genogroup 1B | Uncultured *Prevotella* sp. clone 123-f2 42 16S ribosomal RNA gene, partial sequences. | 69 |
| AY738678 | 1026 bp DNA linear | *Prevotella* genogroup 2 | Uncultured *Prevotella* sp. clone 123-b 46 16S ribosomal RNA gene, partial sequence. | 70 |
| AY738679 | 1026 bp DNA linear | *Prevotella* genogroup 3 | Uncultured *Prevotella* sp. clone 123-f 110 16S ribosomal RNA gene, partial sequence. | 71 |
| AY738680 | 1033 bp DNA linear | *Lactobacillus* sp | Uncultured *Lactobacillus* sp. clone vag1-89 16S ribosomal RNA gene, partial sequence. | 72 |
| AY738681 | 1033 bp DNA linear | *Lactobacillus vaginalis* | Uncultured *Lactobacillus* sp. clone vag4-18 16S ribosomal RNA gene, partial sequence. | 73 |
| AY738682 | 1035 bp DNA linear | *Staphylococcus lugdunensis* | Uncultured *Staphylococcus* sp. clone vag4-92 16S ribosomal RNA gene, partial sequence. | 74 |
| AY738683 | 1039 bp DNA linear | *Gemella* sp. | Uncultured *Gemella* sp. clone BV7-73 16S ribosomal RNA gene, partial sequence. | 75 |
| AY738684 | 1027 bp DNA linear | *Mobiluncus mulieris* | Uncultured *Mobiluncus* sp. clone 123-f 85 16S ribosomal RNA gene, partial sequence | 76 |
| AY738685 | 1025 bp DNA linear | *Prevotella buccalis* | Uncultured *Prevotella* sp. clone 136-b 40 16S ribosomal RNA gene, partial sequence. | 77 |
| AY738686 | 1024 bp DNA linear | *Prevotella disiens* | Uncultured *Prevotella* sp. clone 123-f 19 16S ribosomal RNA gene, partial sequence. | 78 |
| AY738687 | 1026 bp DNA linear | *Prevotella*-like vaginal clone | Uncultured *Prevotella* sp. clone 123-f2 36 16S ribosomal RNA gene, partial sequence. | 79 |
| AY738688 | 1025 bp DNA linear | *Prevotella*-like vaginal clone | Uncultured *Prevotella* sp. clone 123-f2 72 16S ribosomal RNA gene, partial sequence. | 80 |
| AY738689 | 1025 bp DNA linear | uncultured bacterium clone 3BV-10 | Uncultured bacterium clone BV3-10 16S ribosomal RNA gene, partial sequence. | 81 |
| AY738690 | 997 bp DNA linear | TM7 related bacteria | Uncultured candidate division TM7 bacterium clone 4BVQ-92 16S ribosomal RNA gene, partial sequence. | 82 |
| AY738691 | 1001 bp DNA linear | *Peptoniphilus* sp | Uncultured *Peptoniphilus* sp. clone 123-b 21 16S ribosomal RNA gene, partial sequence. | 83 |
| AY738692 | 1001 bp DNA linear | *Peptoniphilus lacrimalis* | Uncultured *Peptoniphilus* sp. clone 123-b 35 16S ribosomal RNA gene, partial sequence | 84 |
| AY738693 | 1003 bp DNA linear | *Peptostreptococcus* sp. | Uncultured *Peptostreptococcus* sp. clone BV1-84 16S ribosomal RNA gene, partial sequence. | 85 |
| AY738694 | 1004 bp DNA linear | *Anaerococcus tetradius* | Uncultured *Anaerococcus* sp. clone 123-f2 5 16S ribosomal RNA gene, partial sequence. | 86 |
| AY738695 | 1018 bp DNA linear | *Gardnerella vaginalis* Type 3 | Uncultured *Gardnerella* sp. clone BV5-62 16S ribosomal RNA gene, partial sequence. | 87 |
| AY738696 | 1033 bp DNA linear | *Aerococcus* sp | Uncultured *Aerococcus* sp. clone 141-b 19 16S ribosomal RNA gene, partial sequence. | 88 |
| AY738697 | 1038 bp DNA linear | *Megasphaera* sp Type 2 | Uncultured *Megasphaera* sp. clone 123-Q 3 16S ribosomal RNA gene, partial sequence. | 89 |
| AY738698 | 1038 bp DNA linear | uncultured bacterium clone 2BV-33 | Uncultured bacterium clone BV2-33 16S ribosomal RNA gene, partial sequence. | 90 |
| AY738699 | 1030 bp DNA linear | uncultured bacterium clone 123f2-102 | Uncultured bacterium clone 123f2-102 16S ribosomal RNA gene, partial sequence. | 91 |
| AY738700 | 1025 bp DNA linear | *Prevotella*-like vaginal clone | Uncultured *Prevotella* sp. clone 7BVA-26 16S ribosomal RNA gene, partial sequence. | 92 |
| AY738701 | 1031 bp DNA linear | uncultured bacterium clone 123-f-67 | Uncultured bacterium clone 123-f 67 16S ribosomal RNA gene, partial sequence. | 93 |
| AY738702 | 1010 bp DNA linear | *Ureaplasma urealyticum* | Uncultured Ureaplasma sp. clone 127-f 65 16S ribosomal RNA gene, partial sequence. | 94 |
| AY738703 | 1018 bp DNA linear | *Staphylococcus epidermidis* | Uncultured *Staphylococcus* sp. clone 2vag-69 16S ribosomal RNA gene, partial sequence. | 95 |
| AY738704 | 989 bp DNA linear | *Clostridium* sp. Vaginal clone | Uncultured *Clostridium* sp. clone 5vag-39 16S ribosomal RNA gene, partial sequence. | 96 |
| AY738705 | 1036 bp DNA linear | *Veillonella* sp. | Uncultured *Veillonella* sp. clone 7BVA-4 16S ribosomal RNA gene, partial sequence. | 97 |
| AY738706 | 1025 bp DNA linear | uncultured bacterium clone BV-27 | Uncultured bacterium clone BV1-27 16S ribosomal RNA gene, partial sequence. | 98 |
| AY724739 | 1007 bp DNA linear | BVAB 1 | Uncultured bacterium clone 123-f 57 16S ribosomal RNA gene, partial sequence | 99 |
| AY724740 | 1009 bp DNA linear | BVAB 2 | Uncultured bacterium clone 123-f 23 16S ribosomal RNA gene, partial sequence. | 100 |
| AY724741 | 1010 bp DNA linear | BVAB 3 | Uncultured bacterium clone 123 f 17 16S ribosomal RNA gene, partial sequence. | 101 |
| AY724742 | 1009 bp DNA linear | *Leptotrichia amnionii* | Uncultured *Leptotrichia* sp. clone 123-b 6 16S ribosomal RNA gene, partial sequence. | 102 |
| bankit643633 | 1007 bp DNA linear | BVAB 1 | Bacterial vaginosis associated bacterium 1, clone 123-f 57, 16S rRNA gene, partial sequence. | 103 |

TABLE 5-continued

Table of GenBank Sequences.

| Locus/<br>Accession No. | Length/Type | Species | Definition | SEQ<br>ID NO: |
|---|---|---|---|---|
| bankit655126 | 1009 bp DNA linear | BVAB 2 | Bacterial vaginosis associated bacterium 2, clone 123-f 23, 16S rRNA gene, partial sequence. | 104 |
| bankit655138 | 1010 bp DNA linear | BVAB 3 | Bacterial vaginosis associated bacterium 3, clone 123-f 17, 16S rRNA gene, partial sequence. | 105 |

TABLE 6

Comparison of PCR assays with standard assays for bacterial vaginosis analyzed according to the Amsel clinical criteria (WRC)
Tabulated-WRC (n = 216)

| ID | PCR + or − | BV + (n = 64) | BV − (n = 152) | BV+ | BV− | Sensitivity | Specificity | Odds Ratio |
|---|---|---|---|---|---|---|---|---|
| BVAB 1 | PCR + | 23 | 4 | 35.9% | 2.6% | 0.3594 | 0.9737 | 20.756 |
|  | PCR − | 41 | 148 |  |  |  |  |  |
| BVAB 2 | PCR + | 54 | 10 | 84.4% | 6.6% | 0.8438 | 0.9442 | 76.680 |
|  | PCR − | 10 | 142 |  |  |  |  |  |
| BVAB 3 | PCR + | 19 | 4 | 29.7% | 2.6% | 0.2969 | 0.9737 | 15.622 |
|  | PCR − | 45 | 148 |  |  |  |  |  |
| *Gardnerella vaginalis* | PCR + | 61 | 107 | 95.3% | 70.4% | 0.9531 | 0.2961 | 8.551 |
|  | PCR − | 3 | 45 |  |  |  |  |  |
| *Atopobium* sp. | PCR + | 61 | 31 | 95.3% | 20.4% | 0.9531 | 0.7961 | 79.366 |
|  | PCR − | 3 | 121 |  |  |  |  |  |
| *Eggerthella*-like uncultured bacterium | PCR + | 57 | 16 | 89.1% | 10.5% | 0.8906 | 0.8947 | 69.214 |
|  | PCR − | 7 | 136 |  |  |  |  |  |
| *Leptotrichia* sp. | PCR + | 50 | 13 | 78.1% | 8.6% | 0.7813 | 0.9145 | 38.187 |
|  | PCR − | 14 | 139 |  |  |  |  |  |
| *Megasphaera* phylotype 1 (*elsdenii*-like) | PCR + | 61 | 16 | 95.3% | 10.5% | 0.9531 | 0.8947 | 172.833 |
|  | PCR − | 3 | 136 |  |  |  |  |  |
| *Megasphaera* phylotype 2 (*micronuciformis*-like) | PCR + | 5 | 0 | 7.8% | 0.0% | 0.0781 | 1.000 | infinity |
|  | PCR − | 59 | 152 |  |  |  |  |  |
| either *Megasphaera* phylotype | PCR + | 62 | 16 | 96.9% | 10.5% | 0.9688 | 0.8947 | 263.5 |
|  | PCR − | 2 | 136 |  |  |  |  |  |
| TM7 | PCR + | 15 | 4 | 23.4% | 2.6% | 0.2344 | 0.9737 | 11.327 |
|  | PCR − | 49 | 148 |  |  |  |  |  |
| *Mobiluncus curtisii* | PCR + | 34 | 12 | 53.1% | 7.9% | 0.5313 | 0.9211 | 13.222 |
|  | PCR − | 30 | 140 |  |  |  |  |  |
| *Mobiluncus mulieris* | PCR + | 14 | 0 | 21.9% | 0.0% | 0.2188 | 1.000 | infinity |
|  | PCR − | 50 | 152 |  |  |  |  |  |
| either *Mobiluncus* sp. | PCR + | 40 | 12 | 62.5% | 7.9% | 0.625 | 0.9211 | 19.444 |
|  | PCR − | 24 | 140 |  |  |  |  |  |
| *Peptoniphilus* sp. | PCR + | 53 | 51 | 82.8% | 33.6% | 0.8281 | 0.6645 | 9.542 |
|  | PCR − | 11 | 101 |  |  |  |  |  |
| *P. lacrimalis* | PCR + | 42 | 25 | 65.6% | 16.4% | 0.6563 | 0.8355 | 9.698 |
|  | PCR − | 22 | 127 |  |  |  |  |  |
| either *Peptoniphilus* | PCR + | 56 | 57 | 87.5% | 37.5% | 0.875 | 0.625 | 11.667 |
|  | PCR − | 8 | 95 |  |  |  |  |  |
| *Prevotella* G1 | PCR + | 35 | 6 | 54.7% | 3.9% | 0.5469 | 0.9605 | 29.368 |
|  | PCR − | 29 | 146 |  |  |  |  |  |
| *Lactobacillus crispatus* | PCR + | 10 | 142 | 15.6% | 93.4% | 0.1563 | 0.0658 | 0.013 |
|  | PCR − | 54 | 10 |  |  |  |  |  |
| *L. iners* | PCR + | 64 | 141 | 100.0% | 92.8% | 1.000 | 0.0724 | infinity |
|  | PCR − | 0 | 11 |  |  |  |  |  |
| either BVAB1 or BVAB2 | PCR + | 55 | 10 | 85.9% | 6.6% | 0.8594 | 0.9342 | 86.778 |
|  | PCR − | 9 | 142 |  |  |  |  |  |
| either BVAB1 or BVAB3 | PCR + | 24 | 7 | 37.5% | 4.6% | 0.375 | 0.9539 | 12.429 |
|  | PCR − | 40 | 145 |  |  |  |  |  |
| either BVAB2 or BVAB3 | PCR + | 55 | 10 | 85.9% | 6.6% | 0.8594 | 0.9342 | 86.778 |
|  | PCR − | 9 | 142 |  |  |  |  |  |
| either BVAB1, BVAB2, BVAB3 | PCR + | 55 | 10 | 85.9% | 6.6% | 0.8594 | 0.9342 | 86.778 |
|  | PCR − | 9 | 142 |  |  |  |  |  |
| either BVAB or *Megasphaera* phylotype 1 | PCR + | 63 | 16 | 98.4% | 10.5% | 0.9844 | 0.8947 | 535.5 |
|  | PCR − | 1 | 136 |  |  |  |  |  |

TABLE 7

Comparison of PCR assays with standard assays for bacterial vaginosis analyzed according to the Nugent clinical criteria (WRC)
Tabulated-WRC (n = 216)

| ID | PCR + or − | BV + (n = 73) | BV − (n = 143) | BV+ | BV− | Sensitivity | Specificity | Odds Ratio |
|---|---|---|---|---|---|---|---|---|
| BVAB 1 | PCR + | 23 | 4 | 31.5% | 2.8% | 0.3151 | 0.9303 | 15.985 |
|  | PCR − | 50 | 139 |  |  |  |  |  |
| BVAB 2 | PCR + | 59 | 5 | 80.8% | 3.5% | 0.8082 | 0.965 | 116.314 |
|  | PCR − | 14 | 138 |  |  |  |  |  |
| BVAB 3 | PCR + | 19 | 4 | 26.0% | 2.8% | 0.2603 | 0.972 | 12.227 |
|  | PCR − | 54 | 139 |  |  |  |  |  |
| *Gardnerella vaginalis* | PCR + | 71 | 78 | 97.3% | 54.5% | 0.9726 | 0.4545 | 29.583 |
|  | PCR − | 2 | 65 |  |  |  |  |  |
| *Atopobium* sp. | PCR + | 70 | 22 | 95.9% | 15.4% | 0.9589 | 0.8462 | 128.333 |
|  | PCR − | 3 | 121 |  |  |  |  |  |
| *Eggerthella*-like uncultured bacterium | PCR + | 65 | 8 | 89.0% | 5.6% | 0.8904 | 0.9441 | 137.109 |
|  | PCR − | 8 | 135 |  |  |  |  |  |
| *Leptotrichia* sp. | PCR + | 54 | 9 | 74.0% | 6.3% | 0.7387 | 0.9371 | 42.316 |
|  | PCR − | 19 | 134 |  |  |  |  |  |
| *Megasphaera* phylotype 1 (*elsdenii*-like) | PCR + | 69 | 8 | 94.5% | 5.6% | 0.9452 | 0.9441 | 291.094 |
|  | PCR − | 4 | 135 |  |  |  |  |  |
| *Megasphaera* phylotype 2 (*micronuciformis*-like) | PCR + | 5 | 0 | 6.8% | 0.0% | 0.0685 | 1.000 | infinity |
|  | PCR − | 68 | 143 |  |  |  |  |  |
| either *Megasphaera* phylotype | PCR + | 70 | 8 | 95.9% | 5.6% | 0.9589 | 0.9441 | 393.750 |
|  | PCR − | 3 | 135 |  |  |  |  |  |
| TM7 | PCR + | 18 | 1 | 24.7% | 0.7% | 0.2466 | 0.993 | 46.473 |
|  | PCR − | 55 | 142 |  |  |  |  |  |
| *Mobiluncus curtisii* | PCR + | 36 | 10 | 49.3% | 7.0% | 0.4932 | 0.9301 | 12.941 |
|  | PCR − | 37 | 133 |  |  |  |  |  |
| *Mobiluncus mulieris* | PCR + | 12 | 2 | 16.4% | 1.4% | 0.1644 | 0.9860 | 13.869 |
|  | PCR − | 61 | 141 |  |  |  |  |  |
| either *Mobiluncus* sp. | PCR + | 40 | 12 | 54.8% | 8.4% | 0.5479 | 0.9161 | 13.232 |
|  | PCR − | 33 | 131 |  |  |  |  |  |
| *Peptoniphilus* sp. | PCR + | 57 | 47 | 78.1% | 32.9% | 0.7808 | 0.6713 | 7.277 |
|  | PCR − | 16 | 96 |  |  |  |  |  |
| *P. lacrimalis* | PCR + | 45 | 22 | 61.6% | 15.4% | 0.6164 | 0.8462 | 8.839 |
|  | PCR − | 28 | 121 |  |  |  |  |  |
| either *Peptoniphilus* | PCR + | 60 | 53 | 82.2% | 37.1% | 0.8219 | 0.6294 | 7.837 |
|  | PCR − | 13 | 90 |  |  |  |  |  |
| *Prevotella* G1 | PCR+ | 37 | 4 | 50.7% | 2.8% | 0.5068 | 0.972 | 35.715 |
|  | PCR − | 36 | 139 |  |  |  |  |  |
| *Lactobacillus crispatus* | PCR + | 6 | 134 | 8.2% | 93.7% | 0.0822 | 0.0629 | 0.006 |
|  | PCR − | 67 | 9 |  |  |  |  |  |
| *L. iners* | PCR + | 69 | 126 | 94.5% | 88.1% | 0.9452 | 0.1189 | 2.327 |
|  | PCR − | 4 | 17 |  |  |  |  |  |

TABLE 8

Comparison of PCR assays with standard assays for bacterial vaginosis analyzed according to the Amsel clinical criteria (STD).
STD Tabulated PCR results

| ID | PCR + or − | BV + (n = 17) | BV − (n = 31) | BV+ | BV− | Sensitivity | Specificity | Odds Ratio |
|---|---|---|---|---|---|---|---|---|
| BVAB 1 | PCR + | 12 | 2 | 70.6% | 6.5% | 0.7059 | 0.9355 | 34.800 |
|  | PCR − | 5 | 29 |  |  |  |  |  |
| BVAB 2 | PCR + | 16 | 3 | 94.1% | 9.7% | 0.9412 | 0.9032 | 149.333 |
|  | PCR − | 1 | 28 |  |  |  |  |  |
| BVAB 3 | PCR + | 15 | 2 | 88.2% | 6.5% | 0.8824 | 0.9355 | 108.750 |
|  | PCR − | 2 | 29 |  |  |  |  |  |
| *Gardnerella vaginalis* | PCR + | 17 | 22 | 100.0% | 71.0% | 1.000 | 0.2903 | infinity |
|  | PCR − | 0 | 9 |  |  |  |  |  |
| *Atopobium* sp. | PCR + | 17 | 11 | 100.0% | 35.5% | 1.000 | 0.6452 | infinity |
|  | PCR − | 0 | 20 |  |  |  |  |  |
| *Eggerthella*-like uncultured bacterium | PCR + | 17 | 9 | 100.0% | 29.0% | 1.000 | 0.7097 | infinity |
|  | PCR − | 0 | 22 |  |  |  |  |  |
| *Leptotrichia* sp. | PCR + | 17 | 7 | 100.0% | 22.6% | 1.000 | 0.77 | infinity |
|  | PCR − | 0 | 24 |  |  |  |  |  |
| *M. elsdenii* | PCR + | 16 | 5 | 94.1% | 16.1% | 0.941 | 0.8387 | 83.200 |
|  | PCR − | 1 | 26 |  |  |  |  |  |
| *M. micronuciformis* | PCR + | 10 | 2 | 58.8% | 6.5% | 0.5882 | 0.9355 | 20.714 |
|  | PCR − | 7 | 29 |  |  |  |  |  |
| either *Megasphaera* | PCR + | 17 | 5 | 100.0% | 16.1% | 1.000 | 0.8387 | infinity |
|  | PCR − | 0 | 26 |  |  |  |  |  |
| TM7 | PCR + | 12 | 0 | 70.6% | 0.0% | 0.7059 | 1.000 | infinity |
|  | PCR − | 5 | 31 |  |  |  |  |  |

TABLE 8-continued

Comparison of PCR assays with standard assays for bacterial vaginosis analyzed according to the Amsel clinical criteria (STD).
STD Tabulated PCR results

| ID | PCR + or − | BV + (n = 17) | BV − (n = 31) | BV+ | BV− | Sensitivity | Specificity | Odds Ratio |
|---|---|---|---|---|---|---|---|---|
| *Mobiluncus curtisii* | PCR + | 11 | 1 | 64.7% | 3.2% | 0.647 | 0.9677 | 55.000 |
|  | PCR − | 6 | 30 |  |  |  |  |  |
| *Mobiluncus mulieris* | PCR + | 4 | 0 | 23.5% | 0.0% | 0.2353 | 1.000 | infinity |
|  | PCR − | 13 | 31 |  |  |  |  |  |
| either *Mobiluncus* sp. | PCR + | 13 | 1 | 76.5% | 3.2% | 0.7647 | 0.9677 | 97.500 |
|  | PCR − | 4 | 30 |  |  |  |  |  |
| *P. lacrimalis* | PCR + | 14 | 4 | 82.4% | 12.9% | 0.8235 | 0.871 | 31.500 |
|  | PCR − | 3 | 27 |  |  |  |  |  |
| *Peptoniphilus* sp. | PCR + | 15 | 15 | 93.8% | 48.4% | 0.9375 | 0.5161 | 16.000 |
|  | PCR − | 1 | 16 |  |  |  |  |  |
| either *Peptoniphilus* sp. | PCR + | 16 | 15 | 94.1% | 48.4% | 0.9412 | 0.5161 | 17.067 |
|  | PCR − | 1 | 16 |  |  |  |  |  |
| *Prevotella* G1 | PCR + | 16 | 5 | 94.1% | 16.1% | 1 | 0.8387 | infinity |
|  | PCR − | 0 | 26 |  |  |  |  |  |
| *L. crispatus* | PCR + | 3 | 22 | 17.6% | 71.0% | 0.177 | 0.2903 | 0.088 |
|  | PCR − | 14 | 9 |  |  |  |  |  |
| *Lactobacillus iners* | PCR + | 16 | 26 | 94.1% | 83.9% | 0.9412 | 0.1613 | 3.077 |
|  | PCR − | 1 | 5 |  |  |  |  |  |
| either BVAB1 or BVAB2 | PCR + | 16 | 3 | 94.1% | 9.7% | 0.9412 | 0.9032 | 149.333 |
|  | PCR − | 1 | 28 |  |  |  |  |  |
| either BVAB1 or BVAB3 | PCR + | 15 | 2 | 88.2% | 6.5% | 0.8824 | 0.9355 | 108.75 |
|  | PCR − | 2 | 29 |  |  |  |  |  |
| either BVAB2 or BVAB3 | PCR + | 16 | 3 | 94.1% | 9.7% | 0.9412 | 0.9032 | 149.333 |
|  | PCR − | 1 | 28 |  |  |  |  |  |
| either BVAB1, BVAB2, BVAB3 | PCR + | 16 | 3 | 94.1% | 9.7% | 0.9412 | 0.9032 | 149.333 |
|  | PCR − | 1 | 28 |  |  |  |  |  |
| either BVAB2 or *Megasphaera* phylotype 1 | PCR + | 17 | 5 | 100.0% | 16.1% | 1 | 0.8387 | infinity |
|  | PCR − | 0 | 26 |  |  |  |  |  |

TABLE 9

Comparison of PCR assays with standard assays for bacterial vaginosis analyzed according to the Amsel clinical criteria (WRC + STD).
Tabulated - All baseline (WRC + STD)

| ID | PCR + or − | BV + (n = 81) | BV − (n = 183) | BV+ | BV− | Sensitivity | Specificity | Odds Ratio |
|---|---|---|---|---|---|---|---|---|
| BVAB 1 | PCR + | 35 | 6 | 43.2% | 3.3% | 0.4321 | 0.9672 | 22.446 |
|  | PCR − | 46 | 177 |  |  |  |  |  |
| BVAB 2 | PCR + | 70 | 13 | 86.4% | 7.1% | 0.8642 | 0.929 | 83.217 |
|  | PCR − | 11 | 170 |  |  |  |  |  |
| BVAB 3 | PCR + | 34 | 6 | 42.0% | 3.3% | 0.4198 | 0.9672 | 21.34 |
|  | PCR − | 47 | 177 |  |  |  |  |  |
| *Gardnerella vaginalis* | PCR + | 78 | 129 | 96.3% | 70.5% | 0.963 | 0.2951 | 10.884 |
|  | PCR − | 3 | 54 |  |  |  |  |  |
| *Atopobium* sp. | PCR + | 78 | 42 | 96.3% | 23.0% | 0.963 | 0.7705 | 87.286 |
|  | PCR − | 3 | 141 |  |  |  |  |  |
| *Eggerthella*-like uncultured bacterium | PCR + | 74 | 25 | 91.4% | 13.7% | 0.9136 | 0.8634 | 66.811 |
|  | PCR − | 7 | 158 |  |  |  |  |  |
| *Leptotrichia* sp. | PCR + | 67 | 20 | 82.7% | 10.9% | 0.8272 | 0.8907 | 39.004 |
|  | PCR − | 14 | 163 |  |  |  |  |  |
| *Megasphaera* phylotype 1 (*elsdenii*-like) | PCR + | 77 | 21 | 95.1% | 11.5% | 0.9506 | 0.8852 | 148.5 |
|  | PCR − | 4 | 162 |  |  |  |  |  |
| *Megasphaera* phylotype 2 (*micronuciformis*-like) | PCR + | 15 | 2 | 18.5% | 1.1% | 0.1852 | 0.9891 | 20.568 |
|  | PCR − | 66 | 181 |  |  |  |  |  |
| either *Megasphaera* phylotype | PCR + | 79 | 21 | 97.5% | 11.5% | 0.9753 | 0.8852 | 304.714 |
|  | PCR − | 2 | 162 |  |  |  |  |  |
| TM7 | PCR + | 27 | 4 | 33.3% | 2.2% | 0.3333 | 0.9781 | 22.375 |
|  | PCR − | 54 | 179 |  |  |  |  |  |
| *Mobiluncus curtisii* | PCR + | 45 | 13 | 55.6% | 7.1% | 0.5556 | 0.929 | 16.346 |
|  | PCR − | 36 | 170 |  |  |  |  |  |
| *Mobiluncus mulieris* | PCR + | 18 | 0 | 22.2% | 0.0% | 0.2222 | 1.0000 | infinity |
|  | PCR − | 63 | 183 |  |  |  |  |  |
| either *Mobiluncus* sp. | PCR + | 53 | 13 | 65.4% | 7.1% | 0.6543 | 0.929 | 24.753 |
|  | PCR − | 28 | 170 |  |  |  |  |  |
| *Peptoniphilus* sp. | PCR + | 67 | 55 | 82.7% | 30.1% | 0.8375 | 0.6995 | 11.994 |
|  | PCR − | 13 | 128 |  |  |  |  |  |
| *P. lacrimalis* | PCR + | 57 | 40 | 70.4% | 21.9% | 0.7037 | 0.7814 | 8.491 |
|  | PCR − | 24 | 143 |  |  |  |  |  |
| either *Peptoniphilus* | PCR + | 72 | 72 | 88.9% | 39.3% | 0.8889 | 0.6066 | 12.333 |
|  | PCR − | 9 | 111 |  |  |  |  |  |

TABLE 9-continued

Comparison of PCR assays with standard assays for bacterial vaginosis analyzed according to the Amsel clinical criteria (WRC + STD).
Tabulated - All baseline (WRC + STD)

| ID | PCR + or − | BV + (n = 81) | BV − (n = 183) | BV+ | BV− | Sensitivity | Specificity | Odds Ratio |
|---|---|---|---|---|---|---|---|---|
| *Prevotella* G1 | PCR+ | 51 | 11 | 63.0% | 6.0% | 0.6375 | 0.9399 | 27.498 |
|  | PCR − | 29 | 172 |  |  |  |  |  |
| *Lactobacillus crispatus* | PCR + | 13 | 164 | 16.0% | 89.6% | 0.1605 | 0.1038 | 0.022 |
|  | PCR − | 68 | 19 |  |  |  |  |  |
| *L. iners* | PCR + | 80 | 167 | 98.8% | 91.3% | 0.9877 | 0.0874 | 7.665 |
|  | PCR − | 1 | 16 |  |  |  |  |  |
| either BVAB1 or BVAB2 | PCR + | 71 | 13 | 87.7% | 7.1% | 0.8765 | 0.9290 | 92.846 |
|  | PCR − | 10 | 170 |  |  |  |  |  |
| either BVAB1 or BVAB3 | PCR + | 39 | 9 | 48.1% | 4.9% | 0.4815 | 0.9508 | 17.952 |
|  | PCR − | 42 | 174 |  |  |  |  |  |
| either BVAB2 or BVAB3 | PCR + | 71 | 13 | 87.7% | 7.1% | 0.8765 | 0.9290 | 92.846 |
|  | PCR − | 10 | 170 |  |  |  |  |  |
| either BVAB1, BVAB2, BVAB3 | PCR + | 71 | 13 | 87.7% | 7.1% | 0.8765 | 0.9290 | 92.846 |
|  | PCR − | 10 | 170 |  |  |  |  |  |
| either BVAB2 or *Megasphaera* phylotype 1 | PCR + | 80 | 21 | 98.8% | 11.5% | 0.9877 | 0.8852 | 617.143 |
|  | PCR − | 1 | 162 |  |  |  |  |  |

TABLE 10

Primers and probes used in qPCR assays for bacterial vaginosis.

| qPCR | Primers/Probe | Primer/Probe sequence | PCR conditions | Cycles | Amplicon size | Sensitivity (gene copies) |
|---|---|---|---|---|---|---|
| Megasphaera Type I | 456F_MegaE | 5'-GATGCCAACAGTATCCGTCC G-3' (SEQ ID NO:106) | 55° C. Anneal 39 sec./ 72° C. Extend 30 sec. | 45 | 211 | 10 |
|  | 667R_MegaE | 5'-CCTCTCCGACACTCAAGTTCG A-3' (SEQ ID NO:107) |  |  |  |  |
|  | Mega_485-506 | 5'-VIC-GTACCGTAAGAGAAAGC CACGG-TAMRA-3' (SEQ ID NO:108) |  |  |  |  |
| BVAB-1 | 576F_BVAB1 | 5'-GGAGTGTAGGCGGCACTA-3' (SEQ ID NO:109) | 57° C. Anneal 39 sec./ 72° C. Extend 30 sec. | 45 | 90 | 5-1 |
|  | 666R_BVAB1 | 5'-TAGAGCTGGAGTATCGGAGA G-3' (SEQ ID NO:110) |  |  |  |  |
|  | BVAB1_610-637 | 5'-FAM-ACCTAAGGCTTAACCAT AGGATTGCATT-3' (SEQ ID NO:111) |  |  |  |  |
| BVAB 2 | 619F_BVAB2 | 5'-TTAACCTTGGGGTTCATTACA A-3' (SEQ ID NO:112) | 59° C. Anneal 39 sec./ 65° C. Extend 30 sec. | 45 | 260 | 5 |
|  | 879R_BVAB2 | 5'-GAATACTTATTGTGTTAACTG CGC-3' (SEQ ID NO:113) |  |  |  |  |
|  | BVAB2_643-665 | 5'-FAM-TCTCCAGCACTCAAGCT AAACAG-TAMRA-3' (SEQ ID NO:114) |  |  |  |  |
| BVAB2_PATH | 585F_BVAB2 | 5'-GCGGCTAGATAAGTGTGATGT TT-3' (SEQ ID NO:115) | 65° C. Anneal/ Extend 1 min. |  | 81 | 5 |
|  | 666R_BVAB2 | 5'-TTTAGCTTGAGTGCTGGAGA G-3' (SEQ ID NO:116) |  |  |  |  |
|  | BVAB2_613-641 | 5'-FAM-CAAGGCTTAACCTTGGG GTTCATTACAA-3' (SEQ ID NO:117) |  |  |  |  |
| BVAB 3 | 1132F_BVAB3 | 5'-CATTTAGTTGGGCACTCAGG C-3' (SEQ ID NO:118) | 65° C. Anneal/ Extend 1 min. | 45 | 160 | 10 |
|  | 1292R_BVAB3 | 5'-GGCGAAGCAAATCCCCAAATG T-3' (SEQ ID NO:119) |  |  |  |  |

TABLE 10-continued

Primers and probes used in qPCR assays for bacterial vaginosis.

| qPCR | Primers/Probe | Primer/Probe sequence | PCR conditions | Cycles | Amplicon size | Sensitivity (gene copies) |
|---|---|---|---|---|---|---|
| | BVAB3_1232-1256 | 5'-TACTACAATGGCTACAACAGA GAGC-TAMRA-3' (SEQ ID NO:120) | | | | |
| G. vaginalis | 983F_Gvag | 5'-ACCTGGGCTTGACATGTGCC T-3' (SEQ ID NO:121) | 67° C. Anneal/ Extend 1 min. | 45 | 76 | 5-1 |
| | 1059R_Gvag | 5'-CAGGTTCACAGGTGGTGCAT G-3' (SEQ ID NO:122) | | | | |
| | G.vag_1008-1032 | 5'-FAM-CTGCAGAGATGTGGTTT CCYTTCG-TAMRA-3' (SEQ ID NO:123) | | | | |
| Leptotrichia/ Sneathia | 559F_Lepto/ Sneath | 5'-AATTATTGGGCTTAAAGGGCA TC-3' (SEQ ID NO:124) | 65° C. Anneal/ Extend 1 min. | 45 | 100-101 | 5 |
| | 659R_Lepto | 5'-CTACAAAACTGTTGAACTAGA GTAC-3' (SEQ ID NO:125) | | | | |
| | 660R_Sneath | 5'-CTACAAAACTGTATAACTAGA GTACT-3' (SEQ ID NO:126) | | | | |
| | Lepto/ Sneath_593-618 | 5'-FAM-ACAAGTTGAAGGTGAAA ACCTRTGGC-TAMRA-3' (SEQ ID NO:127) | | | | |
| Lactobacillus genus | 1130F_J Lacto | 5'-AKCATTAAGTTGGGCACTCTA WT-3' (SEQ ID NO:128) | 65° C. Anneal/ Extend 1 min. | 45 | 153 | 5-1 |
| | 1283R_Lacto | 5'-CCTGYGAAGGCAAGCGGATC T-3' (SEQ ID NO:129) | | | | |
| | Lacto_1234-1261 | 5'-FAM-TCGCTTCTCGTTGTACY GYCCATTGTAG-TAMRA-3' (SEQ ID NO:130) | | | | |

TABLE 11

| PCR Assay/Nugent | 0 v134 | 10 v137 | 7 v139 | 6 v144 | 7 v175 | 0 v177 |
|---|---|---|---|---|---|---|
| BVAB1 | − | + | − | − | − | − |
| BVAB2 | − | + | − | + | + | + |
| BVAB3 | − | − | − | + | − | − |
| G. vaginalis | + | + | + | + | + | + |
| Atopobium | − | + | + | + | + | + |
| Eggerthella | − | + | + | + | + | − |
| Leptotrichia | − | − | − | + | + | − |
| P. lacrimalis | − | − | + | − | + | − |
| Peptoniphilus sp. | + | + | + | − | + | + |
| Megasphaera phylotype 2 (micronucifeormis-like) | − | − | − | − | − | − |
| Megasphaera phylotype 1 (elsdeni-like) | + | + | + | + | + | + |
| TM7 | − | − | + | − | − | − |
| Mobiluncus curtisii | − | + | − | − | + | − |
| Mobiluncus mulieris | − | − | − | − | − | − |
| PrevG1 *(2nd Prev present) | − | + | (+)* | − | + | − |
| PrevG2 | − | | | | | |
| L. crispatus | + | − | − | − | − | − |
| L. iners | + | + | + | + | + | + |

TABLE 12

Plasmids tested in qPCR assays (Example 3)

| | | |
|---|---|---|
| Aerococcus | Peptoniphilus sp. | Prevotella dentalis* |
| Anerococcus* | Peptostreptococcus micros | Prevotella disiens* |
| Atopobium vaginae | Porphyromonas | Prevotella oulorum* |
| BVAB1 | PrevG1 | Prevotella shahii |
| BVAB2 | PrevG2 | Sneathia sanguinegens |
| BVAB3 | PrevG3 | Staphylococcus epidermidis |
| Clostridium sp.* | Prevotella bivia | Staphylococcus lugdunensis |
| Dialister alpha | Lactobacillus crispatus | Sutterella canis* |
| Dialister beta | Lactobacillus gallinarum | TM7 |

TABLE 12-continued

| Plasmids tested in qPCR assays (Example 3) | | |
|---|---|---|
| *E. coli* (genomic DNA) | *Lactobacillus gasseri* | Uncultured bact. 4C28D |
| *Eggerthella hongkongensis* | *Lactobacillus iners* | *Ureaplasma parvulum* |
| *Fusobacterium** | *Lactobacillus jensenii* | *Veillonella* sp.* |
| *G. vaginalis* | *Lactobacillus vaginalis* | |
| *Gemella** | *Leptotrichia amnioni* | |
| *Mobiluncus curtisii* | *Megasphaera* Type I | |
| *Mobiluncus mulieris* | *Megasphaera* Type II | |
| *P. lacrimalis* | *Prevotella buccalis* | |

(*not tested in all assays)

What is claimed is:

1. A method of detecting *Megasphaera* in a sample, comprising:
   a) contacting the sample with a primer pair specific for nucleic acid comprising the nucleotide sequence of SEQ ID NO:64 under conditions whereby nucleic acid amplification can occur; and
   b) detecting amplification of the nucleic acid of (a), thereby detecting *Megasphaera* in the sample, wherein the primer pair comprises 1) a forward primer comprising the nucleotide sequence of SEQ ID NO: 19, and 2) a reverse primer comprising the nucleotide sequence of SEQ ID NO: 20.

2. A method of detecting *Megasphaera* in a sample, comprising:
   a) contacting the sample with a primer pair specific for nucleic acid comprising the nucleotide sequence of SEQ ID NO:64 under conditions whereby nucleic acid amplification can occur; and
   b) detecting amplification of the nucleic acid of (a), thereby detecting *Megasphaera* in the sample, wherein the primer pair comprises 1) a forward primer comprising the nucleotide sequence of (SEQ ID NO: 106, ) and 2) a reverse primer comprising the nucleotide sequence of SEQ ID NO: 107.

3. A method of determining the amount of *Megasphaera* in a sample, comprising:
   a) contacting the sample with a primer pair specific for nucleic acid comprising the nucleotide sequence of SEQ ID NO:64 under conditions whereby nucleic acid amplification can occur and the amount of amplified nucleic acid can be determined; and
   b) detecting amplification of the nucleic acid of (a) and determining the amount of *Megasphaera* nucleic acid and the amount of *Megasphaera* bacteria in the sample, wherein the primer pair comprises 1) a forward primer comprising the nucleotide sequence of SEQ ID NO: 106, and 2) a reverse primer comprising, the nucleotide sequence of SEQ ID NO: 107 and the amplification of nucleic acid of (a) is detected by contacting the nucleic acid of (a) with a detectably labeled probe comprising the nucleotide sequence of SEQ ID NO: 108.

* * * * *

UNITED STATES PATENT AND TRADEMARK OFFICE
CERTIFICATE OF CORRECTION

| | | |
|---|---|---|
| PATENT NO. | : 7,625,704 B2 | Page 1 of 1 |
| APPLICATION NO. | : 11/607639 | |
| DATED | : December 1, 2009 | |
| INVENTOR(S) | : Fredricks et al. | |

It is certified that error appears in the above-identified patent and that said Letters Patent is hereby corrected as shown below:

On Title Page:

Item 54 and in Column 1, Line 3: Please correct the title: "WITH BACTERIA VAGINOSIS"
to read -- WITH BACTERIAL VAGINOSIS --

In the Claims:

Column 156, Claim 2, Line 1: Please correct "(SEQ ID NO: 106,)"
to read -- SEQ ID NO: 106, --

Column 156, Claim 3, Line 16: Please delete the "," in "comprising, the"

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,625,704 B2
APPLICATION NO. : 11/607639
DATED : December 1, 2009
INVENTOR(S) : Fredricks et al.

It is certified that error appears in the above-identified patent and that said Letters Patent is hereby corrected as shown below:

In the Patent:
Column 1, STATEMENT OF GOVERNMENT SUPPORT, Lines 16-19:
Please delete the paragraph in its entirety and replace with the following:

-- This invention was made with government support under grant numbers AI053250, AI052228, and AI061628 awarded by National Institutes of Health. The government has certain rights in the invention --

Signed and Sealed this
Eighth Day of May, 2012

David J. Kappos
*Director of the United States Patent and Trademark Office*

SEQUENCE LISTING

```
<160> NUMBER OF SEQ ID NOS: 130

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
actcctrcgg gaggcagcag                                              20

<210> SEQ ID NO 2
<211> LENGTH: 17
<212> TYPE: DNA
<213> ORGANISM: Artificial
<220> FEATURE:
<223> OTHER INFORMATION: PCR primer

<400> SEQUENCE: 2
gacgggcggt gwgtrca                                                 17

<210> SEQ ID NO 3
<211> LENGTH: 23
<212> TYPE: DNA
<213> ORGANISM: Artificial
<220> FEATURE:
<223> OTHER INFORMATION: PCR primer

<400> SEQUENCE: 3
gtatattttc tacggaacac agg                                          23

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
tttgctccgg atcgctcctt                                              20

<210> SEQ ID NO 5
<211> LENGTH: 22
<212> TYPE: DNA
<213> ORGANISM: Artificial
<220> FEATURE:
<223> OTHER INFORMATION: PCR primer

<400> SEQUENCE: 5
```

```
ttaaccttgg ggttcattac aa                                          22

<210> SEQ ID NO 6
<211> LENGTH: 24
<212> TYPE: DNA
<213> ORGANISM: Artificial
<220> FEATURE:
<223> OTHER INFORMATION: PCR primer

<400> SEQUENCE: 6
aattcagtct cctgaatcgt caga                                        24

<210> SEQ ID NO 7
<211> LENGTH: 24
<212> TYPE: DNA
<213> ORGANISM: Artificial
<220> FEATURE:
<223> OTHER INFORMATION: PCR primer

<400> SEQUENCE: 7
cttgawcgat gtagagatac ataa                                        24

<210> SEQ ID NO 8
<211> LENGTH: 19
<212> TYPE: DNA
<213> ORGANISM: Artificial
<220> FEATURE:
<223> OTHER INFORMATION: PCR primer

<400> SEQUENCE: 8
tgcttcgcct cgcgacgtc                                              19

<210> SEQ ID NO 9
<211> LENGTH: 17
<212> TYPE: DNA
<213> ORGANISM: Artificial
<220> FEATURE:
<223> OTHER INFORMATION: PCR primer

<400> SEQUENCE: 9
gggcgggcta gagtgca                                                17

<210> SEQ ID NO 10
<211> LENGTH: 18
<212> TYPE: DNA
<213> ORGANISM: Artificial
<220> FEATURE:
<223> OTHER INFORMATION: PCR primer

<400> SEQUENCE: 10
gaacccgtgg aatgggcc                                               18

<210> SEQ ID NO 11
<211> LENGTH: 18
<212> TYPE: DNA
<213> ORGANISM: Artificial
<220> FEATURE:
<223> OTHER INFORMATION: PCR primer

<400> SEQUENCE: 11
gcagggacga ggccgcaa                                               18

<210> SEQ ID NO 12
<211> LENGTH: 22
<212> TYPE: DNA
<213> ORGANISM: Artificial
```

```
<220> FEATURE:
<223> OTHER INFORMATION: PCR primer

<400> SEQUENCE: 12
gtgtttccac tgcttcacct aa                                              22

<210> SEQ ID NO 13
<211> LENGTH: 18
<212> TYPE: DNA
<213> ORGANISM: Artificial
<220> FEATURE:
<223> OTHER INFORMATION: PCR primer

<400> SEQUENCE: 13
aacctcgagc cgggttcc                                                   18

<210> SEQ ID NO 14
<211> LENGTH: 21
<212> TYPE: DNA
<213> ORGANISM: Artificial
<220> FEATURE:
<223> OTHER INFORMATION: PCR primer

<400> SEQUENCE: 14
tcggcacgga agatgtaatc t                                               21

<210> SEQ ID NO 15
<211> LENGTH: 22
<212> TYPE: DNA
<213> ORGANISM: Artificial
<220> FEATURE:
<223> OTHER INFORMATION: PCR primer

<400> SEQUENCE: 15
caattctgtg tgtgtgaaga ag                                              22

<210> SEQ ID NO 16
<211> LENGTH: 22
<212> TYPE: DNA
<213> ORGANISM: Artificial
<220> FEATURE:
<223> OTHER INFORMATION: PCR primer

<400> SEQUENCE: 16
acagttttgt aggcaagcct at                                              22

<210> SEQ ID NO 17
<211> LENGTH: 24
<212> TYPE: DNA
<213> ORGANISM: Artificial
<220> FEATURE:
<223> OTHER INFORMATION: PCR primer

<400> SEQUENCE: 17
aaggtggtaa atagccatca tgag                                            24

<210> SEQ ID NO 18
<211> LENGTH: 21
<212> TYPE: DNA
<213> ORGANISM: Artificial
<220> FEATURE:
<223> OTHER INFORMATION: PCR primer

<400> SEQUENCE: 18
ctctccgaca ctcaagtctt c                                               21
```

```
<210> SEQ ID NO 19
<211> LENGTH: 21
<212> TYPE: DNA
<213> ORGANISM: Artificial
<220> FEATURE:
<223> OTHER INFORMATION: PCR primer

<400> SEQUENCE: 19
gatgccaaca gtatccgtcc g                                              21

<210> SEQ ID NO 20
<211> LENGTH: 22
<212> TYPE: DNA
<213> ORGANISM: Artificial
<220> FEATURE:
<223> OTHER INFORMATION: PCR primer

<400> SEQUENCE: 20
cctctccgac actcaagttc ga                                             22

<210> SEQ ID NO 21
<211> LENGTH: 22
<212> TYPE: DNA
<213> ORGANISM: Artificial
<220> FEATURE:
<223> OTHER INFORMATION: PCR primer

<400> SEQUENCE: 21
aactgcttgg ctcgagatta tc                                             22

<210> SEQ ID NO 22
<211> LENGTH: 23
<212> TYPE: DNA
<213> ORGANISM: Artificial
<220> FEATURE:
<223> OTHER INFORMATION: PCR primer

<400> SEQUENCE: 22
tctcctttcg gagaaattct agg                                            23

<210> SEQ ID NO 23
<211> LENGTH: 26
<212> TYPE: DNA
<213> ORGANISM: Artificial
<220> FEATURE:
<223> OTHER INFORMATION: PCR primer

<400> SEQUENCE: 23
aagagacgaa cttagagata agtttt                                         26

<210> SEQ ID NO 24
<211> LENGTH: 22
<212> TYPE: DNA
<213> ORGANISM: Artificial
<220> FEATURE:
<223> OTHER INFORMATION: PCR primer

<400> SEQUENCE: 24
caccttcctc cgatttatca tc                                             22

<210> SEQ ID NO 25
<211> LENGTH: 22
<212> TYPE: DNA
<213> ORGANISM: Artificial
<220> FEATURE:
<223> OTHER INFORMATION: PCR primer
```

```
<400> SEQUENCE: 25
gaccggtata gagatatacc ct                                        22

<210> SEQ ID NO 26
<211> LENGTH: 20
<212> TYPE: DNA
<213> ORGANISM: Artificial
<220> FEATURE:
<223> OTHER INFORMATION: PCR primer

<400> SEQUENCE: 26
ttctcgcgaa aaaggcacag                                           20

<210> SEQ ID NO 27
<211> LENGTH: 20
<212> TYPE: DNA
<213> ORGANISM: Artificial
<220> FEATURE:
<223> OTHER INFORMATION: PCR primer

<400> SEQUENCE: 27
ctggcccatc tctggaacca                                           20

<210> SEQ ID NO 28
<211> LENGTH: 20
<212> TYPE: DNA
<213> ORGANISM: Artificial
<220> FEATURE:
<223> OTHER INFORMATION: PCR primer

<400> SEQUENCE: 28
gctcgtaggt ggttcgtcgc                                           20

<210> SEQ ID NO 29
<211> LENGTH: 19
<212> TYPE: DNA
<213> ORGANISM: Artificial
<220> FEATURE:
<223> OTHER INFORMATION: PCR primer

<400> SEQUENCE: 29
ccacaccatc tctggcatg                                            19

<210> SEQ ID NO 30
<211> LENGTH: 23
<212> TYPE: DNA
<213> ORGANISM: Artificial
<220> FEATURE:
<223> OTHER INFORMATION: PCR primer

<400> SEQUENCE: 30
gtcccttatt gcatgtacca tac                                       23

<210> SEQ ID NO 31
<211> LENGTH: 20
<212> TYPE: DNA
<213> ORGANISM: Artificial
<220> FEATURE:
<223> OTHER INFORMATION: PCR primer

<400> SEQUENCE: 31
gccgctaaca ctaggtgcta                                           20

<210> SEQ ID NO 32
```

```
<211> LENGTH: 21
<212> TYPE: DNA
<213> ORGANISM: Artificial
<220> FEATURE:
<223> OTHER INFORMATION: PCR primer

<400> SEQUENCE: 32
cgacttgagt atgcaggaag t                                               21

<210> SEQ ID NO 33
<211> LENGTH: 24
<212> TYPE: DNA
<213> ORGANISM: Artificial
<220> FEATURE:
<223> OTHER INFORMATION: PCR primer

<400> SEQUENCE: 33
aatgttttca cttggccact catc                                            24

<210> SEQ ID NO 34
<211> LENGTH: 24
<212> TYPE: DNA
<213> ORGANISM: Artificial
<220> FEATURE:
<223> OTHER INFORMATION: PCR primer

<400> SEQUENCE: 34
gatagaggta gtaactggcc ttta                                            24

<210> SEQ ID NO 35
<211> LENGTH: 25
<212> TYPE: DNA
<213> ORGANISM: Artificial
<220> FEATURE:
<223> OTHER INFORMATION: PCR primer

<400> SEQUENCE: 35
ctttgtatct ctacaaatgg cacta                                           25

<210> SEQ ID NO 36
<211> LENGTH: 23
<212> TYPE: DNA
<213> ORGANISM: Artificial
<220> FEATURE:
<223> OTHER INFORMATION: PCR primer

<400> SEQUENCE: 36 acagggtag taactgacct ttg                                              23

<210> SEQ ID NO 37
<211> LENGTH: 24
<212> TYPE: DNA
<213> ORGANISM: Artificial
<220> FEATURE:
<223> OTHER INFORMATION: PCR primer

<400> SEQUENCE: 37
atctaatctc ttagactggc tatg                                            24

<210> SEQ ID NO 38
<211> LENGTH: 20
<212> TYPE: DNA
<213> ORGANISM: Artificial
<220> FEATURE:
<223> OTHER INFORMATION: PCR primer

<400> SEQUENCE: 38
```
gaagagccaa ggacaggtac                                              20

<210> SEQ ID NO 39
<211> LENGTH: 20
<212> TYPE: DNA
<213> ORGANISM: Artificial
<220> FEATURE:
<223> OTHER INFORMATION: PCR primer

<400> SEQUENCE: 39
caacttcatc cacgttcacc                                              20

<210> SEQ ID NO 40
<211> LENGTH: 18
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (18)..(18)
<223> OTHER INFORMATION: Cy5 label

<400> SEQUENCE: 40
gctgcctccc gtaggagt                                                18

<210> SEQ ID NO 41
<211> LENGTH: 18
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (18)..(18)
<223> OTHER INFORMATION: Cy3 label

<400> SEQUENCE: 41
actcctacgg gaggcagc                                                18

<210> SEQ ID NO 42
<211> LENGTH: 21
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (21)..(21)
<223> OTHER INFORMATION: Fluoroscein label

<400> SEQUENCE: 42
ctgctatccc cccggtacag g                                            21

<210> SEQ ID NO 43
<211> LENGTH: 23
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (23)..(23)
<223> OTHER INFORMATION: Cy3 label

<400> SEQUENCE: 43
ccctcttgct tccctctgtc aca                                          23

<210> SEQ ID NO 44
<211> LENGTH: 23
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (23)..(23)
<223> OTHER INFORMATION: Cy3 label

<400> SEQUENCE: 44
cgacgtcgct gctctctgtt gta                                           23

<210> SEQ ID NO 45
<211> LENGTH: 25
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (25)..(25)
<223> OTHER INFORMATION: Cy3 label

<400> SEQUENCE: 45
tcccaaagaa aaggacaggt tactc                                         25

<210> SEQ ID NO 46
<211> LENGTH: 24
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (24)..(24)
<223> OTHER INFORMATION: Cy3 label

<400> SEQUENCE: 46
ccactaaaca ctttcccaac aaga                                          24

<210> SEQ ID NO 47
<211> LENGTH: 17
<212> TYPE: DNA
<213> ORGANISM: Artificial
<220> FEATURE:
<223> OTHER INFORMATION: FISH probe
<220> FEATURE:
<221> NAME/KEY: misc_feature
<222> LOCATION: (17)..(17)
<223> OTHER INFORMATION: Cy3 label

<400> SEQUENCE: 47
ggtcggtctc tcaaccc                                                  17

<210> SEQ ID NO 48
<211> LENGTH: 1000
<212> TYPE: DNA
<213> ORGANISM: uncultured Eggerthella sp.

<400> SEQUENCE: 48
tggggaatat tgcgcaatgg gggaaaccct gacgcagcaa cgccgcgtgc gggatgaagg    60
ccttcgggtt gtaaaccgct ttcagcaggg aagacatcga cggtacctgc agaagaagcc   120
ccggctaact acgtgccagc agccgcggta atacgtaggg ggcgagcgtt atccggattc   180
attgggcgta aagcgcgcgc aggcggttgc tcaagcggaa cctctaatct cggggcttaa   240

```
cctcgagccg ggttccgaac tggacgactc gagtgcggta gaggcagatg gaattcccgg      300
tgtagcggtg gaatgcgcag atatcgggaa gaacaccaac ggcgaaggca gtctgctggg      360
ccgtcactga cgctgaggcg cgaaagctgg gggagcgaac aggattagat accctggtag      420
tcccagccgt aaacgatgag cgctgggtgt gggagattac atcttccgtg ccgaagctaa      480
cgcattaagc gctccgcctg gggagtacgg ccgcaaggct aaaactcaaa ggaattgacg      540
ggggcccgca caagcagcgg agcatgtggc ttaattcgaa gcaacgcgaa gaaccttacc      600
agggcttgac atgtaggtga agcggcgaaa cgtcgtggc cgaaaggagc ctacacaggt       660
ggtgcatggc tgtcgtcagc tcgtgtcgtg agatgttggg ttaagtcccg caacgagcgc      720
aacccctgcc ccgtgttacc agcatttagt tggggactcg cggggactg ccggcgtcaa       780 gccggaggaa ggcggggatg acgtcaagtc atcatgcccc ttatgccctg gccgcacac      840 gtgctacaat ggccggcaca gcgggctgca acctagcgat aggaagcgaa tcccgtaaag      900
ccggtcccag ttcggattgg aggctgaaac ccgcctccat gaagccggag ttgctagtaa      960
tcgcggatca gcacgccgcg gtgaatgcgt tcccgggcct                           1000
```

<210> SEQ ID NO 49
<211> LENGTH: 1008
<212> TYPE: DNA
<213> ORGANISM: uncultured Atopobium sp.

<400> SEQUENCE: 49

```
tggggaatct tgcacaatgg gcgaaagcct gatgcagcga cgccgcgtgc gggatgaagg       60
ccttcgggtt gtaaaccgct ttcagcaggg acgaggccgc aaggtgacgg tacctgcaga     120
agaagccccg gctaactacg tgccagcagc cgcggtaata cgtaggggc aagcgttatc      180 cggattcatt gggcgtaaag cgcgcgtagg cggtctgtta ggtcaggagt taaatctggg     240
ggctcaaccc ctatccgctc ctgataccgg caggcttgag tctggtaggg gaagatggaa     300
ttccaagtgt agcggtgaaa tgcgcagata tttggaagaa caccggtggc gaaggcggtc     360
ttctgggcca tgactgacgc tgaggcgcga aagctagggg agcgaacagg attagatacc     420
ctggtagtcc tagctgtaaa cgatggacac taggtgtggg gagattatac tttccgtgcc     480
gcagctaacg cattaagtgt cccgcctggg gagtacggtc gcaagactaa aactcaaagg     540
aattgacggg ggcccgcaca agcagcggag catgtggctt aattcgaagc aacgcgaaga     600
accttaccag ggcttgacat ttaggtgaag cagtggaaac actgtggccg aaaggagcct     660
aaacaggtgg tgcatggctg tcgtcagctc gtgtcgtgag atgttgggtt aagtcccgca     720
acgagcgcaa cccttgtcgc atgttgccag cggttcggcc gggcacccat gcagaccgc      780 cggcgttaag ccggaggaag gtggggacga cgtcaagtca tcatgcccct tatgtcctgg     840
gctgcacacg tgctacaatg gccggcacag agggctgcta ctgcgcgagc aggagcgaat     900
ccctaaagcc ggtcccagtt cggattggag gctgcaactc gcctccatga agtcggagtt     960
gctagtaatc gcggatcagc acgccgcggt gaatgcgttc ccgggcct                  1008
```

<210> SEQ ID NO 50
<211> LENGTH: 1008
<212> TYPE: DNA
<213> ORGANISM: uncultured Atopobium sp.

<400> SEQUENCE: 50

```
tggggatctt gcacaatggg cgaaagcctg atgcagcgac gccgcgtgcg ggatgaaggc       60
```

```
cttcgggttg taaaccgctt tcagcaggga cgaggccgca aggtgacggt acctgcagaa    120
gaagccccgg ctaactacgt gccagcagcc gcggtaatac gtaggggca agcgttatcc     180 ggattcattg ggcgtaaagc gcgcgtaggc ggtttgttag gtcaggagtt aaatctgggg    240
gctcaacccc tatccgctcc tgataccggc aggcttgagt ctggtagggg aaggcggaat    300
tccaagtgta gcggtgaaat gcgcagatat ttggaagaac accggtggcg aaggcggcct    360
tctgggccac gactgacgct gaggcgcgaa agctagggga gcgaacagga ttagataccc    420
tggtagtcct agccgtaaac gatggacact aggtgtgggg agattatact ttccgtgccg    480
cagccaacgc attaagtgtc ccgcctgggg agtacggtcg caagactaaa actcaaagga    540
attgacgggg gcccgcacaa gcagcggagc atgtggctta attcgaagca acgcgaagaa    600
ccttaccagg gcttgacatt taggtgaagc agtggaaaca ctgtggccga aggagccta    660 aacaggtggt gcatggctgt cgtcagctcg tgtcgtgaga tgttgggtta agtcccgcaa    720
cgagcgcaac ccttgtcgca tgttgccagc ggttaaagcc gggcacccat gcagaccgc    780 cggcgttaag ccggaggaag gtggggacga cgtcaagtca tcatgcccct tatgtcctgg    840
gctgcacacg tgctacaatg gccggcacag agggctgcaa ctgcgcgagc agaagcgaat    900
ccctaaagcc ggtcccagtt cggattggag gctgcaaccc gcctccatga agtcggagtt    960
gctagtaatc gcggatcagc acgccgcggt gaatgcgttc ccgggcct               1008

<210> SEQ ID NO 51
<211> LENGTH: 1009
<212> TYPE: DNA
<213> ORGANISM: uncultured Sneathia sp.

<400> SEQUENCE: 51
tggggaatat tggacaatgg aggcaactct gatccagcaa ttctgtgtgt gtgaagaagg     60
ttttaggact gtaaaacact tttagtaggg aagaaagaaa tgacggtacc tacagaagaa    120
gcgacggcta aatacgtgcc agcagccgcg gtaatacgta tgtcgcgagc gttatccgga    180
attattgggc ttaaagggca tctaggcggt taaacaagtt gaaggtgaaa acctgtggct    240
caaccatagg cttgcctaca aaactgtata actagagtac tggaaaggtg gtggaactaa    300
cacgagtaga ggtgaaattc gtagatatgt gtaggaatgc cgatgatgaa gataactcac    360
tggacagcaa ctgacgctga agtgcgaaag ctaggggagc aaacaggatt agataccctg    420
gtagtcctag ctgtaaacga tgatcactgg gtgtggggat tcgaagtctc tgtgccgaag    480
caaaagcgat aagtgatccg cctggggagt acgttcgcaa gaatgaaact caaaggaatt    540 gacgggacc cgcacaagtg gtggagcatg tggtttaatt cgacgcaacg cgaggaacct    600
taccagatct tgacatcctc cgaagagcat agaagtatgc ttgtgcctac gggaacggag    660
agacaggtgg tgcatggctg tcgacagctc gtgttgtgag atgttgggtt aagtcccgca    720
acgagcgaaa cccctatcat tagttaccat cattaagttg gggactctaa tgaaactgcc    780
tacgaagagt aggaggaagg tgggatgac gtcaagtcat catgcccctt atgatctggg     840
ctacacacgt gctacaatgg atagtacaaa gagaagcttt gtagcgatac atggcaaaac    900
taagaaagct attcttagtt cggattgaag tctgcaactc gacttcatga agttggaatc    960
actagtaatc gtgaatcagc aatgtcacgg tgaatacgtt ctcgggtct              1009

<210> SEQ ID NO 52
<211> LENGTH: 1034
<212> TYPE: DNA
<213> ORGANISM: uncultured Lactobacillus sp.
```

<400> SEQUENCE: 52

```
tagggaaatc ttccacaatg gacgcaagtc tgatggagca acgccgcgtg agtgaagaag      60
gttttcggat cgtaaagctc tgttgttggt gaagaaggat agaggtagta actggccttt     120
atttgacggt aatcaaccag aaagtcacgg ctaactacgt gccagcagcc gcggtaatac     180
gtaggtggca agcgttgtcc ggatttattg ggcgtaaagc gagcgcaggc ggattgataa     240
gtctgatgtg aaagccttcg gctcaaccga gaactgcat cagaaactgt caatcttgag      300
tgcagaagag gagagtggaa ctccatgtgt agcggtggaa tgcgtagata tatggaagaa     360
caccagtggc gaaggcggct ctctggtctg taactgacgc tgaggctcga aagcatgggt     420
agcgaacagg attagatacc ctggtagtcc atgccgtaaa cgatgagtgc taagtgttgg     480
gaggtttccg cctctcagtg ctgcagctaa cgcattaagc actccgcctg gggagtacga     540
ccgcaaggtt gaaactcaaa ggaattgacg ggggcccgca caagcggtgg agcatgtggt     600
ttaattcgaa gcaacgcgaa gaaccttacc aggtcttgac atcctttgac cacctaagag     660
attaggtttt cccttcgggg acaaagagac aggtggtgca tggctgtcgt cagctcgtgt     720
cgtgagatgt tgggttaagt cccgcaacga gcgcaaccct tgttaatagt tgccagcatt     780
aagttgggca ctctattgag actgccggtg acaaaccgga ggaaggtggg gatgacgtca     840
agtcatcatg ccccttatga cctgggctac acacgtgcta caatgggcag tacaacgaga     900
gcgaacctg tgaaggcaag cggatctctt aaagctgttc tcagttcgga ctgtaggctg      960
caactcgcct acacgaagct ggaatcgcta gtaatcgcgg atcagcacgc cgcggtgaat    1020
acgttcccgg gcct                                                      1034
```

<210> SEQ ID NO 53
<211> LENGTH: 1038
<212> TYPE: DNA
<213> ORGANISM: uncultured Dialister sp.

<400> SEQUENCE: 53

```
tggggaatct tccgcaatgg gcgaaagcct gacggagcaa cgccgcgtga gtgaagacgg      60
ccttcgggtt gtaaaactct gtgattcggg acgaaagata agtagacgaa taatctgcat    120
aagtgacggt accgaaaaag caagccacgg ctaactacgt gccagcagcc gcggtaatac    180
gtaggtggca agcgttgtcc ggaattattg ggcgtaaagc gcgcgcaggc ggctacttaa    240
gtccatctta aaagtgcggg gcttaacccc gtgatgggg ggaaactgag aagctggagt      300
gtcggagagg aaagtggaat tcctagtgta gcggtgaaat gcgtagagat taggaagaac    360
accggtggcg aaggcgactt tctggacgac aactgacgct taggcgcgaa agcgtgggga    420
gcaaacagga ttagataccc tggtagtcca cgccgtaaac gatggatact aggtgtagga    480
ggtatcgacc ccttctgtgc cggagttaac gcaataagta tcccgcctgg gaagtacgat    540
cgcaagatta aaactcaaag gaattgacgg gggcccgcac aagcggtgga gtatgtggtt    600
taattcgacg caacgcgaag aaccttacca ggtcttgaca ttgatcgcta ttttcagaaa    660
tgagaagttc ccttcgggga cgagaaaa caggtggtgc acggctgtcg tcagctcgtg      720
tcgtgagatg ttgggttaag tcccgcaacg agcgcaaccc ctatcatttg ttgccagcac    780
gcaaaggtgg gaactcaaat gagaccgccg cagacaatgc ggaggaaggc ggggacgacg    840
tcaagtcatc atgcccctta tgacctgggc tacacacgta ctacaatggg tgtcaacaaa    900
gagaagcgaa ggagcgatcc ggagcaaacc tcaaaaacac acccccagtt cagatcgcag    960
```

```
gctgcaactc gcctgcgtga agcaggaatc gctagtaatc gcgggtcagc ataccgcggt   1020
gaatacgttc ccgggcct                                                  1038

<210> SEQ ID NO 54
<211> LENGTH: 1037
<212> TYPE: DNA
<213> ORGANISM: uncultured Dialister sp.

<400> SEQUENCE: 54
tggggaatct tccgcaatgg acgaaagtct gacggagcaa cgccgcgtga gtgaagacgg     60
ccttcgggtt gtaaagctct gtgattcggg acgaaaggcc atatgtgaat aatatatgga    120
aatgacggta ccgaaaaagc aagccacggc taactacgtg ccagcagccg cggtaatacg    180
taggtggcaa gcgttgtccg gaattattgg gcgtaaagcg cgcgcaggcg gtcacttaag    240
tccatcttag aagtgcgggg cttaaccccg tgatgggatg gaaactggga gactggagta    300
tcggagagga agtggaatt cctagtgtag cggtgaaatg cgtagatatt aggaagaaca    360
ccggtggcga aggcgacttt ctggacgaaa actgacgctg aggcgcgaaa gcgtggggag    420
caaacaggat tagataccct ggtagtccac gccgtaaacg atggatacta ggtgtaggag    480
gtatcgaccc cttctgtgcc ggagttaacg caataagtat cccgcctggg aagtacgatc    540
gcaagattaa aactcaaagg aattgacggg ggccccgcaca agcggtggag tatgtggttt    600
aattcgacgc aacgcgaaga accttaccaa gtcttgacat tgatcgccat ccaagagat    660 tggaagttct ccttcgggag acgagaaaac aggtggtgca cggctgtcgt cagctcgtgt    720
cgtgagatgt tgggttaagt cccgcaacga gcgcaacccc tatcttttgt tgccagcacg    780
tagaggtggg aactcagaag agaccgccgc agacaatgcg gaggaaggtg gggatgacgt    840
caagtcatca tgccccttat gacttgggct acacacgtac tacaatgggc tttaacaaag    900
agcagcgaaa ccgcgaggtg gagcgaaact caaaaacaag cccccagttc agatcgcagg    960
ctgcaactcg cctgcgtgaa gcaggaatcg ctagtaatcg cgggtcagca taccgcggtg   1020
aatacgttcc cgggcct                                                  1037

<210> SEQ ID NO 55
<211> LENGTH: 1033
<212> TYPE: DNA
<213> ORGANISM: uncultured Lactobacillus sp.

<400> SEQUENCE: 55
tagggaatct tccacaatgg acgcaagtct gatggagcaa cgccgcgtga gtgaagaagg     60
ttttcggatc gtaaagctct gttgttggtg aagaaggata gaggtagtaa ctggccttta    120
tttgacggta atcaaccaga aagtcacggc taactacgtg ccagcagccg cggtaatacg    180
taggtggcaa gcgttgtccg gatttattgg gcgtaaagcg agcgcaggcg gaagaataag    240
tctgatgtga aagccctcgg cttaaccgag gaactgcatc ggaaactgtt tttcttgagt    300
gcagaagagg agagtggaac tccatgtgta gcggtggaat gcgtagatat atggaagaac    360
accagtggcg aaggcggctc tctggtctgc aactgacgct gaggctcgaa agcatgggta    420
gcgaacagga ttagataccc tggtagtcca tgccgtaaac gatgagtgct aagtgttggg    480
aggtttccgc ctctcagtgc tgcagctaac gcattaagca ctccgcctgg ggagtacgac    540
cgcaaggttg aaactcaaag gaattgacgg gggcccgcac aagcggtgga gcatgtggtt    600
taattcgaag caacgcgaag aaccttacca ggtcttgaca tctagtgcca tttagaga    660 tacaaagttc ccttcgggga cgctaagaca ggtggtgcat ggctgtcgtc agctcgtgtc    720
```

| | |
|---|---:|
| gtgagatgtt gggttaagtc ccgcaacgag cgcaacccett gttattagtt gccagcatta | 780 |
| agttgggcac tctaatgaga ctgccggtga caaaccggag gaaggtgggg atgacgtcaa | 840 |
| gtcatcatgc cccttatgac ctgggctaca cacgtgctac aatggacggt acaacgagaa | 900 |
| gcgaccctgt gaaggcaagc ggatctctga aagccgttct cagttcggat tgcaggctgc | 960 |
| aactcgcctg catgaagctg gaatcgctag taatcgcaaa tcagcacgtt gcggtgaata | 1020 |
| cgttcccggg cct | 1033 |

<210> SEQ ID NO 56
<211> LENGTH: 1033
<212> TYPE: DNA
<213> ORGANISM: uncultured Lactobacillus sp.

<400> SEQUENCE: 56

| | |
|---|---:|
| tagggaatct tccacaatgg acgcaagtct gatggagcaa cgccgcgtga gtgaagaagg | 60 |
| ttttcggatc gtaaagctct gttgttggtg aagaaggata gaggtagtaa ctggcctttta | 120 |
| tttgacggta atcaaccaga aagtcacggc taactacgtg ccagcagccg cggtaatacg | 180 |
| taggtggcaa gcgttgtccg gatttattgg gcgtaaagcg agcgcaggcg gaagaataag | 240 |
| tctgatgtga aagccctcgg cttaaccgag gaactgcatc ggaaactgtt tttcttgagt | 300 |
| gcagaagagg agagtggaac tccatgtgta gcggtggaat gcgtagatat atggaagaac | 360 |
| accagtggcg aaggcggctc tctggtctgc aactgacgct gaggctcgaa agcatgggta | 420 |
| gcgaacagga ttagataccc tggtagtcca tgccgtaaac gatgagtgct aagtgttggg | 480 |
| aggtttccgc ctctcagtgc tgcagctaac gcattaagca ctccgcctgg ggagtacgac | 540 |
| cgcaaggttg aaaactcaaag gaattgacgg gggcccgcac aagcggtgga gcatgtggtt | 600 |
| taattcgaag caacgcgaag aaccttacca ggtcttgaca tctagtgcca tttgtagaga | 660 |
| tacaaagttc ccttcgggga cgctaagaca ggtggtgcat ggctgtcgtc agctcgtgtc | 720 |
| gtgagatgtt gggttaagtc ccgcaacgag cgcaacccctt gttattagtt gccagcatta | 780 |
| agttgggcac tctaatgaga ctgccggtga caaaccggag gaaggtgggg atgacgtcaa | 840 |
| gtcatcatgc cccttatgac ctgggctaca cacgtgctac aatgggcagt acaacgagaa | 900 |
| gcgagcctgc gaaggcaagc gaatctctga aagctgttct cagttcggac tgcagtctgc | 960 |
| aactcgactg cacgaagctg gaatcgctag taatcgcgga tcagcacgcc gcggtgaata | 1020 |
| cgttcccggg cct | 1033 |

<210> SEQ ID NO 57
<211> LENGTH: 1018
<212> TYPE: DNA
<213> ORGANISM: uncultured Gardnerella sp.

<400> SEQUENCE: 57

| | |
|---|---:|
| tgggaatat tgcgcaatgg gggaaaccct gacgcagcga cgccgcgtgc gggatgaagg | 60 |
| ccttcgggtt gtaaaccgct tttgattggg agcaagcctt cgggtgagtg tacctttcga | 120 |
| ataagcgccg gctaactacg tgccagcagc cgcggtaata cgtagggcgc aagcgttatc | 180 |
| cggaattatt gggcgtaaag agcttgtagg cggttcgtcg cgtctggtgt gaaagcccat | 240 |
| cgcttaacgg tgggtctgcg ccgggtacgg gcgggctaga gtgcagtagg ggagactgga | 300 |
| attcccggtg taacggtgga atgtgtagat atcgggaaga acaccaatgg cgaaggcagg | 360 |
| tctctgggct gttactgacg ctgagaagcg aaagcgtggg gagcgaacag gattagatac | 420 |

```
cctggtagtc cacgccgtaa acggtggacg ctggatgtgg ggcccattcc acgggttccg      480
tgtcggagct aacgcgttaa gcgtcccgcc tggggagtac ggccgcaagg ctaaaactca      540
aagaaattga cggggcccg cacaagcggc ggagcatgcg gattaattcg atgcaacgcg       600
aagaacctta cctgggcttg acatgtgcct gtcgactgca gagatgtggt ttcccttcgg      660
ggcaggttca caggtggtgc atggtcgtcg tcagctcgtg tcgtgagatg ttgggttaag      720
tcccgcaacg agcgcaaccc tcgccctgtg ttgccagcgg ttatgccgg gaactcacgg       780 gggaccgccg ggttaactc ggaggaaggt ggggatgacg tcagatcatc atgcccctta      840
cgtccagggc ttcacgcatg ctacaatggc cggtacaacg gatgcgaca tggtgacatg       900 gagcggatcc cttaaaaccg gtctcagttc ggatcgtagt ctgcaactcg actacgtgaa      960
ggcggagtcg ctagtaatcg cgaatcagca acgtcgcggt gaatgcgttc ccgggcct     1018
```

<210> SEQ ID NO 58
<211> LENGTH: 1019
<212> TYPE: DNA
<213> ORGANISM: uncultured Gardnerella sp.

<400> SEQUENCE: 58

```
tggggaatat tgcgcaatgg gggaaaccct gacgcagcga cgccgcgtgc gggatgaagg       60
ccttcgggtt gtaaaccgct tttgattggg agcaagcctt tgggtgagt gtacctttcg      120 aataagcgcc ggctaactac gtgccagcag ccgcggtaat acgtagggcg caagcgttat      180
ccggaattat tgggcgtaaa gagcttgtag gcggttcgtc gcgtctggtg tgaaagccca      240
tcgcttaacg gtgggtctgc gccgggtacg gcgggctag agtgcagtag gggagactgg      300
aattcccggt gtaacggtgg aatgtgtaga tatcgggaag aacaccaatg gcgaaggcag      360
gtctctgggc tgttactgac gctgagaagc gaaagcgtgg ggagcgaaca ggattagata      420
ccctggtagt ccacgccgta aacggtggac gctggatgtg gggcccattc acgggttcc      480 gtgtcggagc taacgcgtta agcgtcccgc ctggggagta cggccgcaag gctaaaactc      540
aaagaaattg acggggccc gcacaagcgg cggagcatgc ggattaattc gatgcaacgc      600
gaagaaccct acctgggctt gacatgtgcc tgacagctgc agagatgtgg tttcccttcg     660
gggcaggttc acaggtggtg catggtcgtc gtcagctcgt gtcgtgagat gttgggttaa     720
gtcccgcaac gagcgcaacc ctcgccctgt gttgccagcg ggttatgccg ggaactcatg      780
ggggaccgcc ggggttaact cggaggaagg tggggatgac gtcagatcat catgcccctt      840
acgtccaggg cttcacgcat gctacaatgg ccggtacaac gggatgcgac atggtgacat      900
ggagcggatc ccttaaaacc ggtctcagtt cggatcgtag tctgcaactc gactacgtga      960
aggcggagtc gctagtaatc gcgaatcagc aacgtcgcgg tgaatgcgtt cccgggcct    1019
```

<210> SEQ ID NO 59
<211> LENGTH: 1018
<212> TYPE: DNA
<213> ORGANISM: uncultured Gardnerella sp.

<400> SEQUENCE: 59

```
tggggaatat tgcgcaatgg gggaaaccct gacgcagcga cgccgcgtgc gggatgaagg       60
ccttcgggtt gtaaaccgct tttgattggg agcaagcctt cggtgagtg taccttcga       120 ataagcgccg gctaactacg tgccagcagc cgcggtaata cgtagggcgc aagcgttatc      180
cggatttatt gggcgtaaag agcttgtagg cggttcgtcg cgtctggtgt gaaagcccat     240
cgcttaacgg tgggtctgcg ccgggtacgg cgggctaga gtgcagtagg ggaaactgga      300
```

-continued

```
attctcggtg taacggtgga atgtgtagat atcgggaaga acaccaatgg cgaaggcagg    360
tttctgggct gttactgacg ctgagaagcg aaagcgtggg gagcgaacag gattagatac    420
cctggtagtc cacgccgtaa acggtggacg ctggatgtgg ggcccattcc acgggttccg    480
tgtcggagct aacgcgttaa gcgtcccgcc tggggagtac ggccgcaagg ctaaaactca    540
aagaaattga cgggggcccg cacaagcggg ggagcatgcg gattaattcg atgcaacgcg    600
aagaacctta cctgggcttg acatgtgcct gatgactgca gagatgtggt ttcctttcgg    660
ggcaggttca caggtggtgc atggtcgtcg tcagctcgtg tcgtgagatg ttgggttaag    720
tcccgcaacg agcgcaaccc tcgccctgtg ttgccagcgg ttatgccgg gaactcacgg     780 gggaccgccg gggttaactc ggaggaaggt ggggatgacg tcagatcatc atgcccctta    840 cgtccaggc ttcacgcatg ctacaatggc cggtacaacg gggtgcgaca tggtgacatg      900
gagctaatcc cttaaaaccg gtctcagttc ggatcgtagt ctgcaactcg actacgtgaa    960
ggcggagtcg ctagtaatcg cgaatcagca acgtcgcggt gaatgcgttc ccgggcct     1018
```

<210> SEQ ID NO 60
<211> LENGTH: 1018
<212> TYPE: DNA
<213> ORGANISM: uncultured Gardnerella sp.

<400> SEQUENCE: 60

```
tggggaatat tgcgcaatgg gggaaaccct gacgcagcga cgccgcgtgc gggatgaagg    60
ccttcgggtt gtaaaccgct tttgattggg agcaagcttt cgggtgagtg tacctttcga    120
ataagcgccg gctaactacg tgccagcagc cgcggtaata cgtagggcgc aagcgttatc    180
cggaattatt gggcgtaaag agcttgtagg cggttcgtcg cgtctggtgt gaaagcccat    240
cgcttaacgg tgggtttgcg ccgggtacgg gcgggctaga gtgcagtagg ggagactgga    300
attctcggtg taacggtgga atgtgtagat atcgggaaga acaccaatgg cgaaggcagg    360
tctctgggct gttactgacg ctgagaagcg aaagcgtggg gagcgaacag gattagatac    420
cctggtagtc cacgccgtaa acggtggacg ctggatgtgg ggcccattcc acgggttctg    480
tgtcggagct aacgcgttaa gcgtcccgcc tggggagtac ggccgcaagg ctaaaactca    540
aagaaattga cgggggcccg cacaagcggg ggagcatgcg gattaattcg atgcaacgcg    600
aagaacctta cctgggcttg acatgtgcct gattactgca gagatgtggt ttcctttcgg    660
ggcaggttca caggtggtgc atggtcgtcg tcagctcgtg tcgtgagatg ttgggttaag    720
tcccgcaacg agcgcaaccc tcgccctgtg ttgccagcgg ttatgccgg gaactcacgg     780 gggaccgccg gggttaactc ggaggaaggt ggggatgacg tcagatcatc atgcccctta    840 cgtccaggc ttcacgcatg ctacaatggc cggtacaacg ggatgcgaca tggtgacatg      900
gagcggatcc cttaaaaccg gtctcagttc ggatcgtagt ctgcaactcg actacgtgaa    960
ggcggagtcg ctagtaatcg cgaatcagca acgtcgcggt gaatgcgttc ccgggcct     1018
```

<210> SEQ ID NO 61
<211> LENGTH: 1033
<212> TYPE: DNA
<213> ORGANISM: uncultured Lactobacillus sp.

<400> SEQUENCE: 61

```
tagggaatct tccacaatgg acgcaagtct gatggagcaa cgccgcgtga gtgaagaagg    60
gtttcggctc gtaaagctct gttgttggtg aagaaggaca ggggtagtaa ctgacctttg    120
```

-continued

```
tttgacggta atcaattaga aagtcacggc taactacgtg ccagcagccg cggtaatacg      180
taggtggcaa gcgttgtccg gatttattgg gcgtaaagcg agtgcaggcg gctcgataag      240
tctgatgtga aagccttcgg ctcaaccgga gaattgcatc agaaactgtc gagcttgagt      300
acagaagagg agagtggaac tccatgtgta gcggtgaaat gcgtagatat atggaagaac      360
accggtggcg aaggcggctc tctggtctgt tactgacgct gaggctcgaa agcatgggta      420
gcgaacagga ttagataccc tggtagtcca tgccgtaaac gatgagtgct aagtgttggg      480
aggtttccgc ctctcagtgc tgcagctaac gcattaagca ctccgcctgg ggagtacgac      540
cgcaaggttg aaactcaaag gaattgacgg gggcccgcac aagcggtgga gcatgtggtt      600
taattcgaag caacgcgaag aaccttacca ggtcttgaca tccatagcca gtctaagaga      660
ttagatgttc ccttcgggga ctatgagaca ggtggtgcat ggctgtcgtc agctcgtgtc      720
gtgagatgtt gggttaagtc cgcaacgagc gcaacccctt gtcattagtt gccagcatta      780
agttgggcac tctaatgaga ctgccggtga caaaccggag gaaggtgggg atgacgtcaa      840
gtcatcatgc cccttatgac ctgggctaca cacgtgctac aatggacggt acaacgagaa      900
gcgaccctgt gaaggcaagc ggatctctga aagccgttct cagttcggat tgcaggctgc      960
aactcgcctg catgaagctg gaatcgctag taatcgcaaa tcagcacgtt gcggtgaata     1020
cgttcccggg cct                                                        1033
```

<210> SEQ ID NO 62
<211> LENGTH: 1033
<212> TYPE: DNA
<213> ORGANISM: uncultured Lactobacillus sp.

<400> SEQUENCE: 62

```
tagggaatct tccacaatgg acgcaagtct gatggagcaa cgccgcgtga gtgaagaagg       60
gtttcggctc gtaaagctct gttggtagtg aagaaagata gaggtagtaa ctggcccttta    120 tttgacggta attacttaga aagccacggc taactacgtg ccagcagccg cggtaatacg      180
taggtggcaa gcgttgtccg gatttattgg gcgtaaagcg agtgcaggcg gttcaataag      240
tctgatgtga aagccttcgg ctcaaccgga gaattgcatc agaaactgtt gaacttgagc      300
gcagaagagg agagtggaac tccatgtgta gcggtgaaat gcgtagatat atggaagaac      360
accagtggcg aaggcggctc tctggtctgc aactgacgct gaggctcgaa agcatgggta      420
gcgaacagga ttagataccc tggtagtcca tgccgtaaac gatgagtgct aagtgttggg      480
aggtttccgc ctctcagtgc tgcagctaac gcattaagca ctccgcctgg ggagtacgac      540
cgcaaggttg aaactcaaag gaattgacgg gggcccgcac aagcggtgga gcatgtggtt      600
taattcgaag caacgcgaag aaccttacca ggtcttgaca tccagtgcaa acctaagaga      660
ttaggagttc ccttcgggga cgctgagaca ggtggtgcat ggctgtcgtc agctcgtgtc      720
gtgagatgtt gggttaagtc cgcaacgagc gcaacccctt gccattagtt gccatcatta      780
agttgggcac tctaatgaga ctgccggtga caaaccggag gaaggtgggg atgacgtcaa      840
gtcatcatgc cccttatgac ctgggctaca cacgtgctac aatggacggt acaacgagaa      900
gcgaacctgc gaaggcaagc ggatctctga aagccgttct cagttcggac tgtaggctgc      960
aactcgccta cacgaagctg gaatcgctag taatcgcgga tcagcacgcc gcggtgaata     1020
cgttcccggg cct                                                        1033
```

<210> SEQ ID NO 63
<211> LENGTH: 1033

<212> TYPE: DNA
<213> ORGANISM: uncultured Lactobacillus sp.

<400> SEQUENCE: 63

```
tagggaatct tccacaatgg acacaagtct gatggagcaa cgccgcgtga gtgaagaagg      60
gtttcggctc gtaaagctct gttggtagtg aagaaagata gaggtagtaa ctggccttta     120
tttgacggta attacttaga aagtcacggc taactacgtg ccagcagccg cggtaatacg     180
taggtggcaa gcgttgtccg gatttattgg gcgtaaagcg agtgcaggcg gttcaataag     240
tctgatgtga aagccttcgg ctcaaccgga gaattgcatc agaaactgtt gaacttgagt     300
gcagaagagg agagtggaac tccatgtgta gcggtggaat gcgtagatat atggaagaac     360
accagtggcg aaggcggctc tctggtctgc aactgacgct gaggctcgaa agcatgggta     420
gcgaacagga ttagataccc tggtagtcca tgccgtaaac gatgagtgct aagtgttggg     480
aggtttccgc ctctcagtgc tgcagctaac gcattaagca ctccgcctgg ggagtacgac     540
cgcaaggttg aaactcaaag gaattgacgg gggcccgcac aagcggtgga gcatgtggtt     600
taattcgaag caacgcgaag aaccttacca ggtcttgaca tccagtgcaa acctaagaga     660
ttaggagttc ccttcgggga cgctgagaca ggtggtgcat ggctgtcgtc agctcgtgtc     720
gtgagatgtt gggttaagtc ccgcaacgag cgcaacccct tgtcattagt tgccatcatta    780
agttgggcac tctaatgaga ctgccggtga caaaccggag gaaggtgggg atgacgtcaa    840
gtcatcatgc cccttatgac ctgggctaca cacgtgctac aatggacggt acaacgagaa    900
gcgaacctgc gaaggcaagc ggatctctga aagccgttct cagttcggac tgtaggctgc    960
aactcgccta cacgaagctg aatcgctag taatcgcgga tcagcacgcc gcggtgaata    1020
cgttcccggg cct                                                       1033
```

<210> SEQ ID NO 64
<211> LENGTH: 1038
<212> TYPE: DNA
<213> ORGANISM: uncultured Megasphaera sp.

<400> SEQUENCE: 64

```
tggggaatct tccgcaatgg acgaaagtct gacggagcaa cgccgcgtga gtgaagaagg      60
tcttcggatt gtaaagctct gttatacggg acgaaaaaga cggatgccaa cagtatccgt     120
ccgtgacggt accgtaagag aaagccacgg ctaactacgt gccagcagcc gcggtaatac     180
gtaggtggca agcgttgtcc ggaattattg ggcgtaaagg cgcgcaggc ggttcggtaa     240
gtctgtctta aaagtgcggg gcttaacccc gtgagggac ggaaactgtc gaacttgagt     300
gtcggagagg aaagcggaat tcctagtgta gcggtgaaat gcgtagatat taggaggaac     360
accggtggcg aaagcggctt tctggacgac aactgacgct gaggcgcgaa agcgtgggga    420
gcaaacagga ttagataccc tggtagtcca cgccgtaaac gatggatact aggtgtagga    480
ggtatcgacc ccttctgtgc cgtagttaac gctataagta tcccgcctgg ggagtacggc    540
cgcaaggttg aaactcaaag gaattgacgg gggcccgcac aagcggtgga gtatgtggtt   600
taattcgacg caacgcgaag aaccttacca agccttgaca ttgatcgcaa ttttcagaga    660
tgagaagttc ctcttcggag gacgagaaaa caggtggtgc acggctgtcg tcagctcgtg   720
tcgtgagatg ttgggttaag tcccgcaacg agcgcaaccc ctatcttctg ttaccagcac    780
gtaaaggtgg ggactcagga gagactgccg cagacaatgc ggaggaaggc ggggatgacg    840
tcaagtcatc atgccccctta tggcttgggc tacacacgta ctacaatggc tctaaataga    900
```

```
gggaagcgaa ggagcgatcc ggagcaaaac ccaaaaacag agtcccagtt cggattgcag    960
gctgcaactc gcctgcatga agcaggaatc gctagtaatc gcaggtcagc atactgcggt   1020
gaatacgttc ccgggcct                                                 1038
```

<210> SEQ ID NO 65
<211> LENGTH: 1027
<212> TYPE: DNA
<213> ORGANISM: uncultured Porphyromonas sp.

<400> SEQUENCE: 65

```
tgaggaatat tggtcaatgg gcgagagcct gaaccagcca agtcgcgtga aggaagactg     60
cccgcaaggg ttgtaaactt cttttgtatg ggattaaagt cgtctacgtg tagacgtttg    120
cagttaccat acgaataagc atcggctaac tccgtgccag cagccgcggt aatacggagg    180
atgcgagcgt tatccggaat tattgggttt aaagggtgcg taggttgcaa gggaagtcag    240
gggtgaaaag ctatagctca actatggtct tgcctttgaa actctctagc tagagtgtac    300
tggaggtacg tggaacgtgt ggtgtagcgg tgaaatgcat agatatcaca cagaactccg    360
attgcgcagg cagcgtacta cattacaact gacactgaag cacgaaagcg tgggtatcaa    420
acaggattag ataccctggt agtccacgca gtaaacgatg aatactagat ctatgcgata    480
tgacagtatg ggtctaagcg aaagcgataa gtattccacc tggggagtac gccggcaacg    540
gtgaaactca aagagattgg cggggtccg cacaagcgga ggaacatgtg gtttaattcg    600
atgatacgcg aggaaccta cccgggattg aaatgtagat gcatgaggct gagaggtctc    660
ttcccttcgg ggcttctatg taggtgctgc atggttgtcg tcagctcgtg ccgtgaggtg    720
tcggcttaag tgccataacg agcgcaaccc gcgtcgatag ttactaacga gttaagtcga    780
ggactctatc gagacagccg tcgtaagacg agaggaagga gcggatgacg tcaaatcagc    840
acggccctta catccggggc gacacacgtg ttacaatggt agggacagcg agcagccatc    900
tggcgacaga gagctaatct ataaacccta tcccagttcg gatcggagtc tgcaactcga    960
ctctgtgaag ctggattcgc tagtaatcgc gcatcagcca tggcgcggtg aatacgttcc   1020
cggtcct                                                            1027
```

<210> SEQ ID NO 66
<211> LENGTH: 1027
<212> TYPE: DNA
<213> ORGANISM: uncultured Porphyromonas sp.

<400> SEQUENCE: 66

```
tgaggaatat tggtcaatgg gcgagagcct gaaccagcca agtcgcgtga aggaagactg     60
cccgcaaggg ttgtaaactt cttttgtatg ggattaaagt cacctacgtg taggtgtttg    120
cagttaccat acgaataagc atcggctaac tccgtgccag cagccgcggt aatacggagg    180
atgcgagcgt tatccggaat tattgggttt aaagggtgcg taggttgcaa gggaagtcag    240
gggtgaaaag ctatagctca actatggtct tgcctttgaa actctctagc tagagtgtac    300
tggaggtacg tggaacgtgt ggtgtagcgg tgaaatgcat agatatcaca cagaactccg    360
attgcgcagg cagcgtacta cattacaact gacactgaag cacgaaagcg tgggtatcaa    420
acaggattag ataccctggt agtccacgca gtaaacgatg aatactagat ctatgcgata    480
tgacagtatg ggtctaagcg aaagcgataa gtattccacc tggggagtac gccggcaacg    540
gtgaaactca aagagattgg cggggtccg cacaagcgga ggaacatgtg gtttaattcg    600
atgatacgcg aggaaccta cccgggattg aaatgtagat gcatgaggct gagaggtctc    660
```

```
ttcccttcgg ggcttctatg taggtgctgc atggttgtcg tcagctcgtg ccgtgaggtg    720
tcggcttaag tgccataacg agcgcaaccc gcgtcgatag ttactaacga gttaagtcga    780
ggactctatc gagacagccg tcgtaagacg agaggaagga gcggatgacg tcaaatcagc    840
acggccctta catccggggc gacacacgtg ttacaatggt agggacagcg agcagccatc    900
tggcgacaga gagctaatct ataaacccta tcccagttcg gatcggagtc tgcaactcga    960
ctctgtgaag ctggattcgc tagtaatcgc gcatcagcca tggcgcggtg aatacgttcc   1020
cggtcct                                                             1027
```

<210> SEQ ID NO 67
<211> LENGTH: 1023
<212> TYPE: DNA
<213> ORGANISM: uncultured Prevotella sp.

<400> SEQUENCE: 67

```
tgaggaatat tggtcaatgg acgcaagtct gaaccagcca agtagcgtgc aggatgacgg     60
ccctatgggt tgtaaactgc ttttatatgg gataaagtg gggaacgtgt tcccttttgc    120
aggtaccata tgaataagga ccggctaatt ccgtgccagc agccgcggta atacggaagg    180
ttcgggcgtt atccggattt attgggttta agggagcgt aggccgtttg gtaagcgtgt    240
tgtgaaatgt aggagctcaa cttctagatt gcagcgcgaa ctgtcagact tgagtgcgca    300
caacgtaggc ggaattcatg gtgtagcggt gaaatgctta gatatcatga agaactccga    360
ttgcgaaggc agcttacggg agcgcaactg acgctgaagc tcgaaggtgc gggtatcgaa    420
caggattaga taccctggta gtccgcacag taaacgatgg atgcccgctg ttagcaccta    480
gtgttagcgg ctaagcgaaa gcattaagca tcccacctgg ggagtacgcc ggcaacggtg    540
aaactcaaag gaattgacgg gggcccgcac aagcggagga acatgtggtt taattcgatg    600
atacgcgagg aaccttaccc gggcttgaat tgcagatgaa cgatttagag ataatgaggt    660
ccttcgggac atctgtgaag gtgctgcatg gttgtcgtca gctcgtgccg tgaggtgtcg    720
gcttaagtgc cataacgagc gcaaccccett tctttagttg ccatcaggtc atgctgggca    780
ctctggagat actgccaccg taaggtgtga ggaaggtggg gatgacgtca aatcagcacg    840
gcccttacgt ccggggctac acacgtgtta caatgggtgg tacagatagt tggtcgtgtg    900
caaatacgat ctaatcctta aaaccattct cagttcggac tggggtctgc aacccgaccc    960
cacgaagctg gattcgctag taatcgcgca tcagccatgg cgcggtgaat acgttcccgg   1020
cct                                                                1023
```

<210> SEQ ID NO 68
<211> LENGTH: 1025
<212> TYPE: DNA
<213> ORGANISM: uncultured Prevotella sp.

<400> SEQUENCE: 68

```
tgaggaatat tggtcaatgg gcgagagcct gaaccagcca agtagcgtgc aggatgacgg     60
ccctatgggt tgtaaactgc ttttatatgg gaataaagtg agggacgtgt cccttattgc    120
atgtaccata cgaataagga ccggctaatt ccgtgccagc agccgcggta atacggaagg    180
tccaggcgtt atccggattt attgggttta aagggagcgt aggctgtttg ttaagcgtgt    240
tgtgaaatgt aggagctcaa cttttagatt gcagcgcgaa ctggcagact tgagtgcgca    300
caacgtaggc ggaattcatg gtgtagcggt gaaatgctta gatatcatga cgaactccga    360
```

```
ttgcgaaggc agcttacggg agcgcaactg acgctaaagc tcgaaggtgc gggtatcgaa    420
caggattaga taccctggta gtccgcacag taaacgatgg atgcccgctg ttagcaccta    480
gtgttagcgg ctaagcgaaa gcattaagca tcccacctgg ggagtacgcc ggcaacggtg    540
aaactcaaag gaattgacgg gggcccgcac aagcggagga acatgtggtt taattcgatg    600
atacgcgagg aaccttaccc gggcttgaat tgcagatgtt tatatcagag atgatatatt    660
cccttcgggg catttgtgaa ggtgctgcat ggttgtcgtc agctcgtgcc gtgaggtgtc    720
ggcttaagtg ccataacgag cgcaaccect tttttagtt gccatcaggt agtgctgggc     780
actctagaga tactgccacc gtaaggtgtg aggaaggtgg ggatgacgtc aaatcagcac    840
ggcccttacg tccggggcta cacacgtgtt acaatgggtg gtacagagag ttggttgtac    900
gcaagtgcaa tctaatccta aaaaccattc tcagttcgga ctggggtctg caacccgacc    960
ccacgaagct ggattcgcta gtaatcgcgc atcagccatg gcgcggtgaa tacgttcccg   1020
ggcct                                                               1025
```

<210> SEQ ID NO 69
<211> LENGTH: 1025
<212> TYPE: DNA
<213> ORGANISM: uncultured Prevotella sp.

<400> SEQUENCE: 69

```
tgaggaatat tggtcaatgg gcgagagcct gaaccagcca agtagcgtgc aggatgacgg      60
ccctatgggt tgtaaactgc ttttatatgg gaataaagtg agggacgtgt cccttattgc     120
atgtaccata cgaataagga ccggctaatt ccgtgccagc agccgcggta atacggaagg    180
tccaggcgtt atccggattt attgggttta aagggagcgt aggctgtttg ttaagcgtgt    240
tgtgaaatgt aagagctcaa cttttagatt gcagcgcgaa ctggcagact tgagtgcgca    300
caacgtaggc ggaattcatg gtgtagcggt gaaatgctta gatatcatga cgaactccga    360
ttgcgaaggc agcttacggg agcgcaactg acgctaaagc tcgaaggtgc gggtatcgaa    420
caggattaga taccctggta gtccgcacag taaacgatgg atgcccgctg ttagcaccta    480
gtgttagcgg ctaagcgaaa gcattaagca tcccacctgg ggagtacgcc ggcaacggtg    540
aaactcaaag gaattgacgg gggcccgcac aagcggagga acatgtggtt taattcgatg    600
atacgcgagg aaccttaccc gggcttgaat tgcagatgtt tatatcagag atgatatatt    660
cccttcgggg catttgtgaa ggtgctgcat ggttgtcgtc agctcgtgcc gtgaggtgtc    720
ggcttaagtg ccataacgag cgcaaccect tttttagtt gccatcaggt aatgctgggc     780
actctagaga tactgccacc gtaaggtgtg aggaaggtgg ggatgacgtc aaatcagcac    840
ggcccttacg tccggggcta cacacgtgtt acaatgggtg gtacagagag ttggttgtac    900
gcaagtgcaa tctaatccta aaaaccattc tcagttcgga ctggggtctg caacccgacc    960
ccacgaagct ggattcgcta gtaatcgcgc atcagccatg gcgcggtgaa tacgttcccg   1020
ggcct                                                               1025
```

<210> SEQ ID NO 70
<211> LENGTH: 1026
<212> TYPE: DNA
<213> ORGANISM: uncultured Prevotella sp.

<400> SEQUENCE: 70

```
tgaggaatat tggtcaatgg gcgagagcct gaaccagcca agtagcgtgc aggatgacgg      60
ccctatgggt tgtaaactgc ttttatgtgg ggataaagtg cgtgacgtgt catgcattgc    120
```

```
aggtaccaca tgaataagga ccggctaatt ccgtgccagc agccgcggta atacggaagg    180
tccgggcgtt atccggattt attgggttta aagggagcgt aggctgtcta ttaagcgtgt    240
tgtgaaattt accggctcaa ccggtggctt gcagcgcgaa ctggtcgact tgagtatgca    300
ggaagtaggc ggaattcatg gtgtagcggt gaaatgctta gatatcatga cgaactccga    360
ttgcgcaggc agcttactgt agcataactg acgctgatgc tcgaaagtgc gggtatcaaa    420
caggattaga taccctggta gtccgcacgg taaacgatgg atgctcgcta ttcgtcctat    480
ttggatgagt ggccaagtga aaacattaag catcccacct ggggagtacg ccggcaacgg    540
tgaaactcaa aggaattgac gggggcccgc acaagcggag gaacatgtgg tttaattcga    600
tgatacgcga ggaaccttac ccgggcttga actgccagcg aacgatacag agatgttgag    660
gcccttcggg gcgctggtgg agtgctgca tggttgtcgt cagctcgtgc cgtgaggtgt    720
cggcttaagt gccataacga gcgcaaccct tttctttagt tgccatcagg taatgctggg    780
cactctatgg atactgccac cgtaaggtgt gaggaaggtg gggatgacgt caaatcagca    840
cggcccttac gtccggggct acacacgtgt tacaatgggg catacagagt gttggcttaa    900
cgcaagtttg gtctaatctt caaagtgtct cccagttcgg attgggtct gcaacccgac    960 cccatgaagc tggattcgct agtaatcgcg catcagccat ggcgcggtga atacgttccc    1020
gggcct                                                             1026

<210> SEQ ID NO 71
<211> LENGTH: 1026
<212> TYPE: DNA
<213> ORGANISM: uncultured Prevotella sp.

<400> SEQUENCE: 71
tgaggaatat tggtcaatgg gcgagagcct gaaccagcca gtagcgtgc aggatgacgg    60 ccctatgggt tgtaaactgc ttttacgcgg ggataaagtg cgtgacgtgt ctcgcattgc    120
aggtaccgcg tgaataagga ccggctaatt ccgtgccagc agccgcggta atacggaagg    180
tccgggcgtt atccggattt attgggttta aagggagcgc aggccgcccg ataagcgtgt    240
tgtgaaatgt accggctcaa ccggtgagtt gcagcgcgaa ctgtcaggct tgagtgcacg    300
gtaagcaggc ggaattcatg gtgtagcggt gaaatgctta gatatcatga ggaactccga    360
ttgcgaaggc agcttgctgc agtgcgactg acgcttaggc tcgaaggtgc gggtatcaaa    420
caggattaga taccctggta gtccgcacgg taaacgatgg atgcccgctg tccgcccatt    480
cgtggcgggc ggccaagcga aagcgttaag catcccacct ggggagtacg ccggcaacgg    540
tgaaactcaa aggaattgac gggggcccgc acaagcggag gaacatgtgg tttaattcga    600
tgatacgcga ggaaccttac ccgggcttga actgccagtg aacgatacag agatgttgag    660
gcccttcggg gcgctggtgg agtgctgca tggttgtcgt cagctcgtgc cgtgaggtgt    720
cggcttaagt gccataacga gcgcaacccc tctcttcagt tgccatcagg tgatgctggg    780
cactctggag acactgccac cgcaaggtgt gaggaaggtg gggatgacgt caaatcagca    840
cggcccttac gtccggggct acacacgtgt tacaatgggg catacagagc gtcggttcaa    900
cgcaagttgg acccaatctt caaagtgcct cccagttcgg actggggtct gcaacccgac    960
cccacgaagc tggattcgct agtaatcgcg catcagccat ggcgcggtga atacgttccc    1020
gggcct                                                             1026

<210> SEQ ID NO 72
```

```
<211> LENGTH: 1033
<212> TYPE: DNA
<213> ORGANISM: uncultured Lactobacillus sp.

<400> SEQUENCE: 72
tagggaatct tccacaatgg acgcaagtct gatggagcaa cgccgcgtga gtgaagaagg      60
ttttcggatc gtaaagctct gttgttggtg aagaaggata gaggtagtaa ctggccttta     120
tttgacggta atcaaccaga aagtcacggc taactacgtg ccagcagccg cggtaatacg     180
taggtggcaa gcgttgtccg gatttattgg gcgtaaagcg agcgcaggcg gaagaataag     240
tctgatgtga aagccctcgg cttaaccgag gaactgcatc ggaaactgtt tttcttgagt     300
gcagaagagg agagtggaac tccatgtgta gcggtggaat gcgtagatat atggaagaac     360
accagtggcg aaggcggctc tctggtctgc aactgacgct gaggctcgaa agcatgggta     420
gcgaacagga ttagataccc tggtagtcca tgccgtaaac gatgagtgct aagtgttggg     480
aggtttccgc ctctcagtgc tgcagctaac gcattaagca ctccgcctgg ggagtacgac     540
cgcaaggttg aaactcaaag gaattgacgg gggcccgcac aagcggtgga gcatgtggtt     600
taattcgaag caacgcgaag aaccttacca ggtcttgaca tccatagcca gtctaagaga     660
ttagatgttc ccttcgggga ctatgagaca ggtggtgcat ggctgtcgtc agctcgtgtc     720
gtgagatgtt gggttaagtc ccgcaacgag cgcaacccct tgcattagtt gccagcatta     780
agttgggcac tctaatgaga ctgccggtga caaaccggag gaaggtgggg atgacgtcaa     840
gtcatcatgc cccttatgac ctgggctaca cacgtgctac aatggacggt acaacgagaa     900
gcgaccctgt gaaggcaagc ggatctctga aagccgttct cagttcggat tgcaggctgc     960
aactcgcctg catgaagctg gaatcgctag taatcgcaaa tcagcacgtt gcggtgaata    1020
cgttcccggg cct                                                       1033

<210> SEQ ID NO 73
<211> LENGTH: 1033
<212> TYPE: DNA
<213> ORGANISM: uncultured Lactobacillus sp.

<400> SEQUENCE: 73
tagggaatct tccacaatgg gcgcaagcct gatggaacaa caccgcgtga gtgaagaagg      60
gtttcggctc gtaaagctct gttgttggag aagaacgtgc gtgagagtaa ctgttcacgc     120
agtgacggta tccaaccaga aagtcacggc taactacgtg ccagcagccg cggtaatacg     180
taggtggcaa gcgttatccg gatttattgg gcgtaaagcg agcgcaggcg gttgcttagg     240
tctgatgtga aagccttcgg cttaaccgaa gaagtgcatc ggaaaccggg cgacttgagt     300
gcagaagagg acagtggaac tccatgtgta gcggtggaat gcgtagatat atggaagaac     360
accagtggcg aaggcggctg tctggtctgc aactgacgct gaggctcgaa agcatgggta     420
gcgaacagga ttagataccc tggtagtcca tgccgtaaac gatgagtgct aggtgttgga     480
gggtttccgc ccttcagtgc cggagctaac gcattaagca ctccgcctgg ggagtacgac     540
cgcaaggttg aaactcaaag gaattgacgg gggcccgcac aagcggtgga gcatgtggtt     600
taattcgaag ctacgcgaag aaccttacca ggtcttgaca tcttgcgcta acctaagaga     660
ttaggcgttc ccttcgggga cgcaatgaca ggtggtgcat ggtcgtcgtc agctcgtgtc     720
gtgagatgtt gggttaagtc ccgcaacgag cgcaacccct gttactagtt gccagcattt     780
agttgggcac tctagtgaga ctgccggtga caaaccggag gaaggtgggg acgacgtcag     840
atcatcatgc cccttatgac ctgggctaca cacgtgctac aatggacggt acaacgagtt     900
```

```
gcgaactcgc gagagtaagc taatctctta aagccgttct cagttcggac tgtaggttgc    960
aactcgccta cacgaagtcg gaatcgctag taatcgcgga tcagcatgcc gcggtgaata   1020
cgttcccggg cct                                                     1033

<210> SEQ ID NO 74
<211> LENGTH: 1035
<212> TYPE: DNA
<213> ORGANISM: uncultured Staphylococcus sp.

<400> SEQUENCE: 74
tagggaatct tccgcaatgg gcgaaagcct gacggagcaa cgccgcgtga gtgatgaagg     60
tcttaggatc gtaaaactct gttattaggg aagaacaaac gtgtaagtaa ctgtgcacgt    120
cttgacggta cctaatcaga aagccacggc taactacgtg ccagcagccg cggtaatacg    180
taggtggcaa gcgttatccg gaattattgg gcgtaaagcg cgcgtaggcg gttttttaag    240
tctgatgtga agcccacggg ctcaaccgtg gagggtcatt ggaaactgga aaacttgagt    300
gcagaagagg aaagtggaat tccatgtgta gcggcgaaat gcgcagagat atggaggaac    360
accagtggcg aaggcgactt tctggtctgt aactgacgct gatgtgcgaa agcgtgggga    420
tcaaacagga ttagataccc tggtagtcca cgccgtaaac gatgagtgct aagtgttagg    480
gggtttccgc cccttagtgc tgcagctaac gcattaagca ctccgcctgg ggagtacgac    540
cgcaaggttg aaactcaaag gaattgacgg ggacccgcac aagcggtgga gcatgtggtt    600
taattcgaag caacgcgaag aaccttacca atcttgaca tccttgacc gctctagaga    660 tagagtcttc cccttcgggg acaaagtga caggtggtgc atggttgtcg tcagctcgtg    720
tcgtgagatg ttgggttaag tcccgcaacg agcgcaaccc ttaagcttag ttgccatcat    780
ttagttgggc actctaagtt gactgccggt gacaaaccgg aggaaggtgg ggatgacgtc    840
aaatcatcat gccccttatg atttgggcta cacacgtgct acaatggaca atacaaaggg    900
cagcgaaacc gcgaggtcaa gcaaatccca taaagttgtt ctcagttcgg attgtagtct    960
gcaactcgac tacatgaagc tggaatcgct agtaatcgta gatcagcatg ctacggtgaa   1020
tacgttcccg ggtct                                                   1035

<210> SEQ ID NO 75
<211> LENGTH: 1039
<212> TYPE: DNA
<213> ORGANISM: uncultured Gemella sp.

<400> SEQUENCE: 75
tagggaatct tccgcaatgg acgaaagtct gacggagcaa cgccgcgtga gtgaagaagg     60
atttcggttc gtaaaactct gttgttaggg aagaaaaaat gtatagtaac tatatacaaa    120
agagacggta cctaaccaga aagccacggc taactacgtg ccagcagccg cggtaatacg    180
taggtggcaa gcgttgtccg gaattattgg gcgtaaagcg cgcgcaggtg gtttagaaag    240
tctgatgtga agcccacggg ctcaaccgtg gagggtcatt ggaaactaat aaacttgagt    300
gcaggagaga aagtggaat tcctagtgta gcggtgaaat gcgtagagat taggaggaac    360
accggtggcg aaagcggctt tttggcctgc aactgacact gaggcgcgaa agcgtgggga    420
gcaaacagga ttagataccc tggtagtcca cgccgtaaac gatgagtgct aagtgttgga    480
gtcaaaagac ttcagtgctg cagcaaacgc attaagcact ccgcctgggg agtacgatcg    540
caagattgaa actcaaagga attgacgggg acccgcacaa gcggtggagt atgtggttta    600
```

```
attcgaagca acgcgaagaa ccttaccaag tcttgacata cagtgaagat ataagaaatt    660
atattgtttt aatgtttaca ttaaacactg atacaggtgg tgcatggttg tcgtcagctc    720
gtgtcgtgag atgttgggtt aagtcccgca acgagcgcaa cccttatatc tagttaccag    780
cagtaagatg gggactctag atagactgcc agtgacaaac tggaggaagg tggggatgac    840
gtcaaatcat catgcccctt atgacttggg ctacacacgt actacaatgg ataggaacaa    900
agagaagcga cctcgcaaga gcaagccaac ctcagaaaac tattctcagt tcggattgta    960
ggctgcaact cgcctacatg aagctggaat cgctagtaat cgcgaatcag aatgtcgcgg   1020
tgaatacgtt cccgggtct                                                1039

<210> SEQ ID NO 76
<211> LENGTH: 1027
<212> TYPE: DNA
<213> ORGANISM: uncultured Mobiluncus sp.

<400> SEQUENCE: 76
tggggaatat tgcacaatgg acggaagttt gatgcagcga cgccgcgtgg agggtgtagg     60
ccttcgggtt gtgaactcct tttctcgtg aaaaaggcat gcttttgggt gtgttgatgg    120
tagcggggga agaagcgccg gctaactacg tgccagcagc cgcggtaata cgtagggcgc    180
gagcgttgtc cggatttatt gggcgtaaag agctcgtagg tggttcgtcg cgtctgtcgt    240
gaaagccagc agcttaactg ttggtctgcg gtgggtacgg gcgggcttga gtgcggtagg    300
ggtgactgga attcctggtg tagcggtgga atgcgcagat atcaggagga acaccgatgg    360
cgaaggcagg tcactgggcc gttactgacg ctgaggagcg aaagcgtggg gagcgaacag    420
gattagatac cctggtagtc cacgctgtaa acgttgggaa ctaggtgtgg ggatgctatc    480
ctgtgtttct gcgccgtagc taacgcatta agttccccgc ctggggagta cggccgcaag    540
gctaaaactc aaaggaattg acgggggccc gcacaagcgg cggagcatgc ggattaattc    600
gatgcaacgc gaagaacctt accaaggctt gacatacact gcgacatgcc agagatggtg    660
tggccttcgg ggtggtgtac aggtggtgca tggttgtcgt cagctcgtgt cgtgagatgt    720
tgggttaagt cccgcaacga gcgcaaccct tgcctcatgt tgccagcacg ttatggtggg    780
gactcgtgag ggactgccgg ggttaactcg gaggagggtg gggatgacgt caaatcatca    840
tgccccttat gtcttgggct tcacgcatgc tacaatggcc agtacagagg gttgcgatac    900
cgtgaggtgg ggctaatctc ttaaagctgg tctcggttcg gattgggtc tgcaactcga    960 ccccatgaag ttggagtcgc tagtaatcgc agatcagcat tgctgcggtg aatacgttct   1020
cgggcct                                                             1027

<210> SEQ ID NO 77
<211> LENGTH: 1025
<212> TYPE: DNA
<213> ORGANISM: uncultured Prevotella sp.

<400> SEQUENCE: 77
tgaggaatat tggtcaatgg gcgagagcct gaaccagcca agtagcgtgc aggatgacgg     60
ccctatgggt tgtaaactgc ttttatgcgg ggataaagtg cgtgacgtgt catgcattgc    120
aggtaccgca tgaataagga ccggctaatt ccgtgccagc agccgcggta atacggaagg    180
tccgggcgtt atccggattt attgggttta aagggagcgt aggccgccag ataagcgtgt    240
tgtgaaatgt accggctcaa ccggtgaatt gcagcgcgaa ctgtttggct tgagtgcacg    300
gtaagcaggc ggaattcatg gtgtagcggt gaaatgctta gatatcatga agaactccga    360
```

```
ttgcgaaggc agcttgctgc agtgcgactg acgctgatgc tcgaaggtgc gggtatcaaa      420
caggattaga taccctggta gtccgcacgg taaacgatgg atgcccgctg tccgcctttt      480
gtggcgggtg ccaagcgaaa gcgttaagc  atcccacctg gggagtacgc cggcaacggt      540
gaaactcaaa ggaattgacg ggggcccgca caagcggagg aacatgtggt ttaattcgat      600
gatacgcgag gaaccttacc cgggcttgaa ctgccagtga acgatacaga gatgttgagg      660
cccttcgggg cgctggtgga ggtgctgcat ggttgtcgtc agctcgtgcc gtgaggtgtc      720
ggcttaagtg ccataacgag cgcaacccct tttttcagtt gccatcaggt aatgctgggc      780
actctggaga tactgccacc gcaaggtgtg aggaaggtgg ggatgacgtc aaatcagcac      840
ggcccttacg tccggggcta cacacgtgtt acaatgggc  atacagagtg ttggcttaac      900
gcaagtttgg tctaatcttc aaagtgtctc ccagttcgga ctggggtctg caacccgacc      960
ccacgaagct ggattcgcta gtaatcgcgc atcagccatg gcgcggtgaa tacgttcccg     1020
ggcct                                                                 1025

<210> SEQ ID NO 78
<211> LENGTH: 1024
<212> TYPE: DNA
<213> ORGANISM: uncultured Prevotella sp.

<400> SEQUENCE: 78
tgaggaatat tggtcaatgg acgagagtct gaaccagcca agtagcgtgc aggatgacgg       60
ccctatgggt tgtaaactgc ttttgtttgg gaataatcga cattacgtgt aatgttttgc      120
atgtaccatt cgaataagga ccggctaatt ccgtgccagc agccgcggta atacggaagg      180
tccaggcgtt atccggattt attgggttta aagggagtgt aggcggttgg ttaagcgtgt      240
tgtgaaatgt agatgctcaa catctgactt gcagcgcgaa ctggctgact tgagtacaca      300
caacgtaggc ggaattcatg gtgtagcggt gaaatgctta gatatcatga gaactccga       360 ttgcgaaggc agcttacggg agtgttactg acgcttaagc tcgaaggtgc gggtatcgaa      420
caggattaga taccctggta gtccgcacag taaacgatgg atgcccgctg ttagcacctg      480
gtgttagcgg ctaagcgaaa gcattaagca tcccacctgg ggagtacgcc ggcaacggtg      540
aaactcaaag gaattgacgg ggcccgcac  aagcggagga acatgtggtt taattcgatg      600
atacgcgagg aaccttaccc gggcttgaat tgtaggagca cgatacagag atgttgaggt      660
ccttcgggac tccatgaag  gtgctgcatg gttgtcgtca gctcgtgccg tgaggtgtcg      720
gcttaagtgc cataacgagc gcaacccctt ccttagttg  ccatcaggta atgctgggca      780
ctctgaggat actgccaccg taaggtgtga ggaaggtggg gatgacgtca aatcagcacg      840
gcccttacgt ccggggctac acacgtgtta caatggccgg tacagaatgt tggttgcatg      900
taaatgtaat ctaatcttta aagccggtcc cagttcggac tgaggtctgc aacccgacct      960
cacgaagctg gattcgctag taatcgcgca tcagccatgg cgcggtgaat acgttcccgg     1020
gcct                                                                  1024

<210> SEQ ID NO 79
<211> LENGTH: 1026
<212> TYPE: DNA
<213> ORGANISM: uncultured Prevotella sp.

<400> SEQUENCE: 79
tgaggaatat tggtcaatgg gcgcgagcct gaaccagcca agtagcgtgc aggacgacgg       60
```

```
ccctatgggt tgtaaactgc ttttatgcgg ggataaagga gtccacgtgt ggattttgc      120 aggtaccgca tgaataagga ccggctaatt ccgtgccagc agccgcggta atacggaagg      180
tccgggcgtt atccggattt attgggttta aagggagcgt aggccgcgtt ttaagcgtgt      240
tgtgaaatgt aggcgcccaa cgtctgcatc gcagcgcgaa ctggaacgct tgagtacgcg      300
caacgttggc ggaattcgtc gtgtagcggt gaaatgctta gatatgacga agaactccga      360
ttgcgaaggc agctgacggg agcggcactg acgcttaagc tcgaaggtgc gggtatcaaa      420
caggattaga taccctggta gtccgcacag taaacgatgg atgcccgctg tgtgccattt      480
atggtacgcg gctaagcgaa agcgttaagc atcccacctg gggagtacgc cggcaacggt      540
gaaactcaaa ggaattgacg ggggcccgca caagcggagg aacatgtggt ttaattcgat      600
gatacgcgag gaaccttacc cgggcttgaa ttgcagatgt ttatatcaga gatgatatat      660
tcccttcggg gcatttgtga aggtgctgca tggttgtcgt cagctcgtgc cgtgaggtgt      720
cggcttaagt gccataacga gcgcaacccc tttttttagt tgccatcagg tagtgctggg      780
cactctagag atactgccac cgtaaggtgt gaggaaggtg gggatgacgt caaatcagca      840
cggcccttac gtccggggct acacacgtgt tacaatgggg ggtacagaga gttggttgta      900
cgcaagtgca atctaatcct aaaaaccatt ctcagttcgg actgggtct gcaacccgac       960 cccacgaagc tggattcgct agtaatcgcg catcagccat ggcgcggtga atacgttccc      1020
gggcct                                                                1026

<210> SEQ ID NO 80
<211> LENGTH: 1025
<212> TYPE: DNA
<213> ORGANISM: uncultured Prevotella sp.

<400> SEQUENCE: 80
tgaggaatat tggtcaatgg gcgtgagcct gaaccagcca agtagcgtgc aggaagacgg       60
ccctatgggt tgtaaactgc ttttatgcgg ggataaagga gtccacgtgt ggattttgc      120 aggtaccgca tgaataagga ccggctaatt ccgtgccagc agccgcggta atacggaagg      180
tccgggcgtt atccggattt attgggttta aagggagcgt aggccgcgtt ttaagcgtgt      240
tgtgaaatgt agacgcccaa cgtctgcatc gcagcgcgaa ctgggacgct tgagtacgcg      300
caacgttggc ggaattcgtc gtgtagcggt gaaatgctta gatatgacga ggaactccga      360
ttgcgaaggc agctgacggg agcggcactg acgcttaagc tcgaaggtgc gggtatcaaa      420
caggattaga taccctggta gtccgcacag taaacgatgg atgcccgctg tgtgcctatt      480
atggtacgcg gctaagcgaa agcgttaagc atcccacctg gggagtacgc cggcaacggt      540
gaaactcaaa ggaattgacg ggggcccgca caagcggagg aacatgtggt ttaattcgat      600
gatacgcgag gaaccttacc cgggcttgaa ctgccggtgc acgatccaga gatggtgagg      660
cccttcgggg cgcggtgga ggtgctgcat ggttgtcgtc agctcgtgcc gtgaggtgtc       720
ggcttaagtg ccataacgag cgcaaccccct ctccgtagtt gccatcaggt aatgctgggc     780
actctgcgga tactgccacc gcaaggtgcg aggaaggtgg ggatgacgtc aaatcagcac      840
ggcccttacg tccggggcta cacacgtgtt acaatggggc atacagagtg ttggcttaac      900
gcaagtttgg tctaatcttc aaagtgtctc ccagttcgga ttggggtctg caacccgacc      960
ccatgaagct ggattcgcta gtaatcgcgc atcagccatg gcgcggtgaa tacgttcccg      1020
ggcct                                                                 1025
```

<210> SEQ ID NO 81
<211> LENGTH: 1025
<212> TYPE: DNA
<213> ORGANISM: uncultured bacterium

<400> SEQUENCE: 81

| | | | | | | |
|---|---|---|---|---|---|---|
| tgaggaatat | tggtcaatgg | gcgggagcct | gaaccagcca | agtagcgtgc | aggaagacgg | 60 |
| ccctatgggt | tgtaaactgc | ttttatgcgg | ggataaagga | gtccacgtgt | gggcttttgc | 120 |
| aggtaccgca | tgaataagga | ccggctaatt | ccgtgccagc | agccgcggta | atacggaagg | 180 |
| tccgggcgtt | atccggattt | attgggttta | aagggagcgt | aggccgcgtt | ttaagcgtgt | 240 |
| tgtgaaatgt | aggcgcccaa | cgtctgcatc | gcagcgcgaa | ctggaacgct | tgagtacgcg | 300 |
| caacgttggc | ggaattcgtc | gtgtagcggt | gaaatgctta | gatatgacga | agaactccga | 360 |
| ttgcgaaggc | agctgacggg | agcggcactg | acgcttaagc | tcgaaggtgc | gggtatcaaa | 420 |
| caggattaga | taccctggta | gtccgcacgg | taaacgatgg | atgctcgctg | tgtgcctttt | 480 |
| gtggtacgcg | gctaagcgaa | agcgttaagc | atcccacctg | gggagtacgc | cggcaacggt | 540 |
| gaaactcaaa | ggaattgacg | ggggcccgca | caagcggagg | aacatgtggt | ttaattcgat | 600 |
| gatacgcgag | gaaccttacc | cgggcttgaa | ctgccggcga | acgatccaga | gatggtgagg | 660 |
| cccctcgggg | cgccggtgga | ggtgctgcat | ggttgtcgtc | agctcgtgcc | gtgaggtgtc | 720 |
| ggcttaagtg | ccataacgag | cgcaaccccct | ctccgtagtt | gccatcaggt | agtgctgggc | 780 |
| actctgcgga | cactgccacc | gcaaggtgcg | aggaaggtgg | ggatgacgtc | aaatcagcac | 840 |
| ggccccttacg | tccggggcta | cacacgtgtt | acaatggggg | gcagcgagc | tcggccgcgc | 900 |
| gcaagctcgg | tccaatcaag | aaatcccccc | tcagttcgga | ctggggtctg | caacccgacc | 960 |
| ccacgaagct | ggattcgcta | gtaatcgcgc | atcagccatg | gcgcggtgaa | tacgttcccg | 1020 |
| ggcct | | | | | | 1025 |

<210> SEQ ID NO 82
<211> LENGTH: 997
<212> TYPE: DNA
<213> ORGANISM: uncultured candidate division TM7 bacterium

<400> SEQUENCE: 82

| | | | | | | |
|---|---|---|---|---|---|---|
| tgaggaatat | tccacaatgg | gcgaaagcct | gatggagcaa | tgccgcgtgc | aggatgaagg | 60 |
| ccctcgggtc | gtaaactgct | tttattagag | aagaatatga | cggtaactaa | tgaataaggg | 120 |
| acggctaact | acgtgccagc | agccgcggtc | atacgtaggt | cccaagcgtt | atccggagtg | 180 |
| actgggcgta | aagagttgcg | taggcggcta | agtaagcgag | taatgaaaac | tatcggctca | 240 |
| accggtagcc | tgttattcga | actgcttggc | tcgagattat | cagaggtcgc | tggaattcct | 300 |
| agtgtagcag | tgaaatgcgt | agatattagg | aagaacacca | atggcgtagg | caggcgactg | 360 |
| gggtatttct | gacgctaagg | cacgaaagcg | tgggagcga | accggattag | ataccccgggt | 420 |
| agtccacgcc | gtaaacgatg | gatgctaatt | gttcggggta | tcgaccccctt | gagtaataaa | 480 |
| gctaacgcgt | taagcatccc | gcctgtggag | tacggccgca | aggctaaaac | ataaaggaat | 540 |
| tgacggggac | ccgcacaagc | ggtggaggat | gttctttaat | tcgatgataa | gcgaagaacc | 600 |
| ttaccagggc | ttgacatccc | tagaatttct | ccgaaggag | agagtgcttt | taagaacta | 660 |
| ggtgacagat | cctgcatggc | cgtcgtcagc | tcgtgtcgtg | agatgtttgg | ttaagtccat | 720 |
| caacgagcgc | aacccttatc | gttagttgta | ttttctaac | gagactgccc | cggtaacggg | 780 |
| gaggaaggag | gggatgatgt | caggtcagta | ttggtcttac | gtcctgggct | agaaacgtcc | 840 |

-continued

```
tacaatggct agtacaatgg gcagcgaatc cgcgaggtga agcaaatccc atcaaagcta    900
gtcccagttc ggattgcagg ctgaaactcg cctgcatgaa gtcggaatcg ctagtaatcg    960
cagatcagca cgctgtcggt gaatacgttc ccgggtc                             997
```

<210> SEQ ID NO 83
<211> LENGTH: 1001
<212> TYPE: DNA
<213> ORGANISM: uncultured Eggerthella sp.

<400> SEQUENCE: 83

```
tggggaatat tgcacaatgg agggaactct gatgcagcga cgccgcgtga acgaagaagg     60
ctttcgagtc gtaaagttct tttatatggg aagataatga cggtaccata agaaaaagcc    120
ccggctaact acgtgccagc agccgcggta atacgtaggg ggctagcgtt gtccggaatc    180
actgggcgta aagggttcgc aggcggaaat gcaagtcagg tgtaaaaggc agtagcttaa    240
ctactgtaag catttgaaac tgcatatctt gagaagagta gaggtaagtg gaattttttag    300 tgtagcggtg aaatgcgtag atattaaaaa gaataccggt ggcgaaggcg acttactggg    360
ctcattctga cgctgaggaa cgaaagcgtg ggtagcaaac aggattagat accctggtag    420
tccacgctgt aaacgatgag tgctaggtat cggaagaatt cggtgccgca gttaacacat    480
taagcactcc gcctggggag tacgtgcgca agcatgaaac tcaaaggaat tgacggggac    540
ccgcacaagc agcggagcat gtggtttaat tcgaagcaac gcgaagaacc ttaccagggc    600
ttgacatact gaggaccggt atagagatat accctcttct tcggaagcct caatacaggt    660
ggtgcatggt tgtcgtcagc tcgtgtcgtg agatgttcag ttaagtctgg caacgagcgc    720
aacccctatc tttagttacc agcatttcgg atggggactc taaagagact gccgatgata    780
aatcggagga aggtggggat gacgtcaaat catcatgccc tatatgccct gggctacaca    840
cgtgctacaa tggaagatac aaagggaagc gaaatagtga tattaagcaa acctcaaaaa    900
gtctttccca gttcggattg tactctgcaa ctcgagtaca tgaagatgga gttgctagta    960
atcgcagatc agaatgctgc ggtgaatgcg ttcccgggtc t                       1001
```

<210> SEQ ID NO 84
<211> LENGTH: 1001
<212> TYPE: DNA
<213> ORGANISM: uncultured Peptoniphilus sp.

<400> SEQUENCE: 84

```
tggggaatat tgcacaatgg gggaaaccct gatgcagcga cgccgcgtga gcgaagaagg     60
ccttcgggtc gtaaagctct tttatatggg aagataatga cggtaccata agaaaaagcc    120
ccggctaact acgtgccagc agccgcggta atacgtaggg ggctagcgtt gtccggaatc    180
actgggcgta aagggttcgc aggcggcaat gcaagtcaga tgtaaaaggc aaaggctcaa    240
cctttgtaag catctgaaac tgtatagctt gagaagtgta gaggcaagtg gaattttttag    300 tgtagcggtg aaatgcgtag atattaaaaa gaataccggt ggcgaaggcg acttgctggg    360
cacaatctga cgctgaggaa cgaaagcgtg gggagcaaac aggattagat accctggtag    420
tccacgccgt aaacgatgag tgctaggtgt cggtataaat cggtgccgca gttaacacaa    480
taagcactcc gcctggggag tacgtgcgca agcatgaaac tcaaaggaat tgacggggac    540
ccgcacaagc agcggagcat gtggtttaat tcgaagcaac gcgaagaacc ttaccagggc    600
ttgacatata agagacgaac ttagagataa gttttcttct tcggaagccc ttatacaggt    660
ggtgcatggt tgtcgtcagc tcgtgtcgtg agatgttggg ttaagtcccg caacgagcgc    720
```

```
aacccttatt actagttacc agcatttcgg atggggactc tagaaagact gccgatgata    780
aatcggagga aggtggggat gacgtcaaat catcatgccc tatatgccct gggcaacaca    840
cgtgctacaa tggccgtaac aaagagaagc gaaatcgcaa ggtcaagcaa acctcaaaaa    900
gacggtctca gttcggattg ttctctgcaa ctcgagaaca tgaagtcgga gttgctagta    960
atcgcagatc agaatgctgc ggtgaatgcg ttcccgggtc t                       1001
```

<210> SEQ ID NO 85
<211> LENGTH: 1003
<212> TYPE: DNA
<213> ORGANISM: uncultured Peptostreptococcus sp.

<400> SEQUENCE: 85

```
tggggaatat tgcacaatgg gggaaaccct gatgcagcga cgccgcgtga gcgaagaagg     60
ctttcgagtc gtaaagctct gtcctatgag aagataatga cggtatcata ggaggaagcc    120
ctggctaaat acgtgccagc agccgcggta atacgtatgg ggcgagcgtt gtccggaatt    180
attgggcgta aagggtacgt aggcggtttt ttaagtcagg tgtcaaagcg tggagcttaa    240
ctccattaag cacttgaaac tgaaagactt gagtgaagga gaggaaagtg gaattcctag    300
tgtagcggtg aaatgcgtag atattaggag gaataccggt ggcgaaggcg actttctgga    360
cttttactga cgctcaggta cgaaagcgtg gggagcaaac aggattagat accctggtag    420
tccacgccgt aaacgatgaa tgctaggtgt tgggagtcaa atctcggtgc cgaagttaac    480
acattaagca ttccgcctgg ggagtacggt ggcaacactg aaactcaaag gaattgacgg    540
ggacccgcac aagcagcgga gcatgtggtt taattcgaag caacgcgaag aaccttacca    600
aggcttgaca tatagttgag ttattgagaa attgataagt ccctcgggac aactatacag    660
gtggtgcatg gttgtcgtca gctcgtgtcg tgagatgttg ggttaagtcc cgcaacgagc    720 gcaacccttta ttttcagtta ccagcattta aggtggggac tctgaagaga ctgccgatga    780
caaatcggag gaaggtgggg atgacgtcaa atcatcatgc cctttatgtc ttgggctaca    840
cacgtgctac aatggtcggt acaacgagaa gcgagatagt gatgttaagc gaaactctaa    900
aagccgatct cagttcggat tgtaggctgc aactcgccta catgaagtcg gagttgctag    960
taatcgcgaa tcagaacgtc gcggtgaatg cgttcccggg tct                     1003
```

<210> SEQ ID NO 86
<211> LENGTH: 1004
<212> TYPE: DNA
<213> ORGANISM: uncultured Anaerococcus sp.

<400> SEQUENCE: 86

```
tggggaattt tgcacaatgg gggaaaccct gatgcagcga cgccgcgtga tttagaaggc     60 cttcggggttg taaaaatctt ttgtatggga agaaaatgac agtaccatac gaataaggac    120
cggctaatta cgtgccagca gccgcggtaa tacgtaaggt ccgagcgttg tccggaatca    180
ttgggcgtaa agggtacgta ggcggataag caagttagag gtgaaatcct atagctcaac    240
tatagtaagc tttttaaaact gctcatcttg aggtatggaa gggaaagtgg aattcctagt    300
gtagcggtga aatgcgcaga tattaggagg aataccggtg gcgaaggcga ctttctggcc    360
ataaactgac gctgaggtac gaaagcgtgg gtagcaaaca ggattagata ccctggtagt    420
ccacgccgta aacgatgagt gttaggtgtc tggaataatc tgggtgccgc agctaacgca    480
ataaacactc cgcctgggga gtacgcacgc aagtgtgaaa ctcaaaggaa ttgacgggga    540
```

```
cccgcacaag cagcggagca tgtggtttaa ttcgacgcaa cgcgaagaac cttaccaagt    600
cttgacatat tacggaggga attagagata gttccttact tcttcggaag actgtaatac    660
aggtggtgca tggttgtcgt cagctcgtgt cgtgagatgt tgggttaagt cccataacga    720
gcgcaacccc tatatttagt taccatcatt aagttgggga ctctagatat actgccggtg    780
ataaaccgga ggaaggtggg gatgacgtca atcatcatg  ccctttatga cttgggctac    840
acacgtgcta caatggcagg tacacaggga agcgagactc gaagttaag  caaaactcaa    900 aaagcctgtc ccagttcgga ttgcactctg caactcgagt gcatgaagtt ggagttgcta    960
gtaatcgtgg atcagaatgc cgcggtgaat gcgttcccgg gtct                    1004

<210> SEQ ID NO 87
<211> LENGTH: 1018
<212> TYPE: DNA
<213> ORGANISM: uncultured Gardnerella sp.

<400> SEQUENCE: 87
tggggaatat tgcgcaatgg gggaaaccct gacgcagcga cgccgcgtgc gggatgaagg     60
ccttcgggtt gtaaaccgct tttgattggg agcaagcttt cgggtgagtg tacctttcga    120
ataagcgccg gctaactacg tgccagcagc cgcggtaata cgtagggcgc aagcgttatc    180
cggaattatt gggcgtaaag agcttgtagg cggttcgtcg cgtctggtgt gaaagcccat    240
cgcttaacgg tgggtctgcg ccgggtacgg gcgggctaga gtgcagtagg ggaaactgga    300
attctcggtg taacggtgga atgtgtagat atcgggaaga acaccaatgg cgaaggcagg    360
tttctgggct gttactgacg ctgagaagcg aaagcgtggg gagcgaacag gattagatac    420
cctggtagtc cacgccgtaa acggtggacg ctggatgtgg ggcccattcc acgggttccg    480
tgtcggagct aacgcgttaa gcgtcccgcc tggggagtac ggccgcaagg ctaaaactca    540
aagaaattga cggggcccg  cacaagcggc ggagcatgcg gattaattcg atgcaacgcg    600 aagaaccttsa cctgggcttg acatgtgcct gacgactgca gagatgtggt tcctttcgg    660 ggcaggttca caggtggtgc atggtcgtcg tcagctcgtg tcgtgagatg ttgggttaag    720
tcccgcaacg agcgcaaccc tcgccctgtg ttgccagcgg gttatgccgg gaactcacgg    780
gggaccgccg gggttaactc ggaggaaggt ggggatgacg tcagatcatc atgcccctta    840
cgtccagggc ttcacgcatg ctacaatggc cagtacaacg ggttgcgaca tggtgacatg    900
gagctaatcc cttaaaactg gtctcagttc ggatcgtagt ctgcaactcg actacgtgaa    960
ggcggagtcg ctagtaatcg cgaatcagca acgtcgcggt gaatgcgttc ccgggcct    1018

<210> SEQ ID NO 88
<211> LENGTH: 1033
<212> TYPE: DNA
<213> ORGANISM: uncultured Aerococcus sp.

<400> SEQUENCE: 88
tagggaatct tccgcaatgg acgcaagtct gacggagcaa cgccgcgtga gtgaagaagg     60
ttttcggatc gtaaaactct gttgtaagag aagaacaaat tgtagagtaa ctgctacagt    120
cttgacggta tcttaccaga aagccacggc taactacgtg ccagcagccg cggtaatacg    180
taggtggcaa cgttgtccg  gatttattgg gcgtaaaggg ggcgcaggct gcttcttaag    240
tctgatgtga aagcccacgg cttaaccgtg gaagtgcatt ggaaactggg aagcttgagt    300
acagaagagg aaagtggaac tccatgtgta gcggtgaaat gcgtagatat atggaagaac    360
accagtggcg aaagcgactt tctggtctgt cactgacgct gaggcccgaa agcgtgggta    420
```

```
gcaaacagga ttagataccc tggtagtcca cgccgtaaac gatgagcgct aggtgttgga      480
gggtttccac ccttcagtgc cgcagctaac gcattaagcg ctccgcctgg ggagtacgac      540
cgcaaggttg aaactcaaag gaattgacgg gacccgcac aagcggtgga gcatgtggtt       600
taattcgaag caacgcgaag aaccttacca agtcttgaca tcctttgacc actctagaga      660
tagagctttc ccttcgggga caaagtgaca gtggtgcat ggttgtcgtc agctcgtgtc       720
gtgagatgtt gggttaagtc ccgcaacgag cgcaacccct attgttagtt gccagcattg      780
agttgggcac tctagcaaga ctgccggtga caaccggag gaaggcgggg atgacgtcaa       840
atcatcatgc cccttatgac ttgggctaca cacgtgctac aatggatggt acaacgggca      900
gcgagctcgc gagagtcagc gaatccctta aagccattct cagttcggat tgtagtctgc      960
aactcgacta catgaagccg gaatcgctag taatcgcgga tcagcacgcc gcggtgaata     1020
cgttcccggg tct                                                        1033

<210> SEQ ID NO 89
<211> LENGTH: 1038
<212> TYPE: DNA
<213> ORGANISM: uncultured Megasphaera sp.

<400> SEQUENCE: 89
tggggaatct tccgcaatgg acgaaagtct gacggagcaa cgccgcgtga gtgaagacgg       60
tcttcggatt gtaaagctct gttatacggg acgaacggca aggtggtaaa tagccatcat      120
gagtgacggt accgtaagag aaagccacgg ctaactacgt gccagcagcc gcggtaatac      180
gtaggtggca agcgttgtcc ggaattattg ggcgtaaagg cgcgcaggc ggttttttaa       240 gtcggtctta aaagtgcggg gcttaacccc gtgagggac cgaaactgga agacttgagt      300
gtcggagagg aaagcggaat tcctagtgta gcggtgaaat gcgtagatat taggaggaac      360
accggtggcg aaagcggctt tctggacgac aactgacgct gaggcgcgaa agcgtgggga      420
gcaaacagga ttagataccc tggtagtcca cgccgtaaac gatggatact aggtgtagga      480
ggtatcgact cctttctgtgc cgtagttaac gctataagta tcccgcctgg ggagtacggc     540
cgcaaggttg aaactcaaag gaattgacgg gggcccgcac aagcggtgga gtatgtggtt      600
taattcgacg caacgcgaag aaccttacca agccttgaca ttgatcgcaa ttttcagaga     660
tgagaagttc ctcttcggag gacgagaaaa caggtggtgc acggctgtcg tcagctcgtg      720
tcgtgagatg ttgggttaag tcccgcaacg agcgcaaccc ctatcttctg ttaccagcac     780
gtaatggtgg ggactcagga gagactgccg cagacaatgc ggaggaaggc ggggatgacg      840
tcaagtcatc atgcccctta tggcttgggc tacacacgta ctacaatggc tcttaataga      900
gggaagcgaa ggagtgatct ggagcaaacc ccaaaaacag agtctcagtt cggattgtag     960
gctgcaactc gcctacatga agcaggaatc gctagtaatc gcaggtcagc atactgcggt     1020
gaatacgttc ccgggcct                                                   1038

<210> SEQ ID NO 90
<211> LENGTH: 1038
<212> TYPE: DNA
<213> ORGANISM: uncultured bacterium

<400> SEQUENCE: 90
tggggaatct tccgcaatgg gcgaaagcct gacggagcaa cgccgcgtga gtgaagacgg       60 ccttcggggtt gtaaaactct gtgattcggg acgaaagata agtagacgaa taatctgcat     120
```

-continued

```
aagtgacggt accgaaaaag caagccacgg ctaactacgt gccagcagcc gcggtaatac    180
gtaggtggca agcgttgtcc ggaattattg ggcgtaaagc gcgcgcaggc ggctacttaa    240
gtccatctta aaagtgcggg gcttaacccc gtgatgggat ggaaactgag aagctggagt    300
gtcggagagg aaagtggaat tcctagtgta gcggtgaaat gcgtagagat taggaagaac    360
accggtggcg aaggcgactt tctggacgac aactgacgct taggcgcgaa agcgtgggga    420
gcaaacagga ttagataccc tggtagtcca cgccgtaaac gatggatact aggtgtagga    480
ggtatcgacc ccttctgtgc cggagttaac gcaataagta tcccgcctgg gaagtacgat    540
cgcaagatta aaactcaaag gaattgacgg gggcccgcac aagcggtgga gtatgtggtt    600
taattcgacg caacgcgaag aaccttacca ggtcttgaca ttgatcgcta ttttcagaaa    660
tgagaagttt ccttcgggga cgagaaaaca ggtggtgc acggctgtcg tcagctcgtg    720
tcgtgagatg ttgggttaag tcccgcaacg agcgcaaccc ctatcatttg ttgccagcac    780
gcaaaggtgg gaactcaaat gagaccgccg cagacaatgc ggaggaaggc ggggacgacg    840
tcaagtcatc atgccccta tgacctgggc tacacacgta ctacaatggg tgtcaacaaa    900
gagaagcgaa ggagcgatcc ggagcaaacc tcaaaaacac accccagtt cagatcgcag    960 gctgcaactc gcctgcgtga agcaggaatc gctagtaatc gcgggtcagc ataccgcggt   1020
gaatacgttc ccgggcct                                                 1038
```

<210> SEQ ID NO 91
<211> LENGTH: 1030
<212> TYPE: DNA
<213> ORGANISM: uncultured bacterium

<400> SEQUENCE: 91

```
tgaggaatat tggtcaatgg gcgcgagcct gaaccagcca agtcgcgtga gggacgacgg     60
tcctacggat tgtaaacctc tttaggcggg gagtaatgtg ctctacgagt agagtagtga    120
gagtacccgc agaataagca tcggctaact ccgtgccagc agccgcggta atacggagga    180
tgcgagcgtt atccggattt attgggttta aagggtgcgc aggctgtgca tcaagtcagc    240
ggtaaaatct cggggctcaa ccccgtttag ccgttgaaac tggtgtgctg gagtgtgcgc    300
gaggaaggcg gaatgcgcgg tgtagcggtg aaatgcatag atattgcgca gaactccgat    360
tgcgaaggca gccttccagt gcatgactga cgctgaggca cgaaagcgtg gtatcgaac    420 aggattagat accctggtag tccacgcagt aaacgatgaa tactatcttt ccgtcgcgcc    480 tgagcgggg gaggacaagc gaaagcgtta agtattccac ctggggagta cgccggcaac    540
ggtgaaactc aaaggaattg acggggccc gcacaagcgg aggaacatgt ggtttaattc    600
gatgatacgc gaggaacctt acccgggctc aaacgctgct agatcggtgt ggaaacacgc    660
cttcccttcg gggctgtcag cgaggtgctg catggttgtc gtcagctcgt gccgtgaggt    720
gtcggcttaa gtgccataac gagcgcaacc cccatctcca gttgccatcg gttcaagccg    780
ggcactctgg agagactgcc ggcgcaagcc gtgaggaggg cggggatgac gtcaaatcag    840 cacgccctt acgtccgggg cgacacacgt gttacaatgg cggagttaca gcgggaagcc    900
aggcggcgac gtcgagctga tcccgaaaat ccgtctcagt tcggatcgga gtctgcaacc    960
cgactccgtg aagctggatt cgctagtaat cgcgcatcag ccatggcgcg gtgaatacgt   1020
tcccgggcct                                                          1030
```

<210> SEQ ID NO 92
<211> LENGTH: 1025

<212> TYPE: DNA
<213> ORGANISM: uncultured Prevotella sp.

<400> SEQUENCE: 92

```
tgaggaatat tggtcaatgg gcgtgagcct gaaccagcca agtagcgtgc aggaagacgg      60
ccctatgggt tgtaaactgc ttttatgcgg ggataaagga gtccacgtgt gggcttttgc     120
aggtaccgca tgaataagga ccggctaatt ccgtgccagc agccgcggta atacggaagg     180
tccgggcgtt atccggattt attgggttta aagggagcgt aggccgcgtt ttaagcgtgt     240
tgtgaaatgt aggcgcccaa cgtctgcatc gcagcgcgaa ctggaacgct tgagtacgcg     300
caacgttggc ggaattcgtc gtgtagcggt gaaatgctta gatatgacga agaactccga     360
ttgcgaaggc agctgacggg agcggcactg acgcttaagc tcgaaggtgc gggtatcaaa     420
caggattaga taccctggta gtccgcacgg taaacgatgg atgcccgctg tgcgcctttc     480
ggggcgcgcg gccaagcgaa agcgttaagc atcccacctg gggagtacgc cggcaacggt     540
gaaactcaaa ggaattgacg ggggcccgca caagcggagg aacatgtggt ttaattcgat     600
gatacgcgag gaaccttacc cgggcttgaa ctgccggcga acgatccaga gatggtgagg     660
cccctcgggg cgtcggtgga ggtgctgcat ggttgtcgtc agctcgtgcc gtgaggtgtc     720
ggcttaagtg ccataacgag cgcaaccccct ctccgtagtt gccatcaggt agtgctgggc     780
actctgcgga cactgccacc gcaaggtgcg aggaaggtgg ggatgacgtc aaatcagcac     840
ggcccttacg tccggggcta cacacgtgtt acaatggggg gcacagcgag tcggccgcgc     900
gcaagctcgg tccaatcaag aaatcccccc tcagttcgga ctggggtctg caacccgacc     960
ccacgaagct ggattcgcta gtaatcgcgc atcagccatg gcgcggtgaa tacgttcccg    1020
ggcct                                                                1025
```

<210> SEQ ID NO 93
<211> LENGTH: 1031
<212> TYPE: DNA
<213> ORGANISM: uncultured bacterium

<400> SEQUENCE: 93

```
tgaggaatat tggtcaatgg gcgcgagcct gaaccagcca agtcgcgtga gggacgacgg      60
ttcctacgga ttgtaaacct ctttaggcgg gagtaatgt gctctacgag tagagtagtg      120
agagtacccg cagaataagc atcggctaac tccgtgccag cagccgcggt aatacggagg     180
atgcgagcgt tatccggatt tattgggttt aaagggtgcg caggctgtgc atcaagtcag     240
cggtaaaatc tcggggctca accccgttta gccgttgaaa ctggtgtgct ggagtgtgcg     300
cgaggaaggc ggaatgcgcg gtgtagcggt gaaatgcata gatattgcgc agaactccga     360
ttgcgaaggc agccttccag tgcatgactg acgctgaggc acgaaagcgt gggtatcgaa     420
caggattaga taccctggta gtccacgcag taaacgatga atactatctt tccgtcgcga     480
ttgagcgggg ggaggacaag cgaaagcgtt aagtattcca cctggggagt acgccggcaa     540
cggtgaaact caaaggaatt gacgggggcc cgcacaagcg gaggaacatg tggtttaatt     600
cgatgatacg cgaggaacct taccccgggct caaacgctga tagaccggtg tggaaacacg     660
ccttcccttc ggggctgtca gcgaggtgct gcatggttgt cgtcagctcg tgccgtgagg     720
tgtcggctta agtgccataa cgagcgcaac ccccatctcc agttgccatc ggttaaagcc     780
gggcactctg gagagactgc cggcgcaagc cgtgaggagg cggggatga cgtcaaatca     840
gcacggccct tacgtccggg gcgacacacg tgttacaatg gcggagttac agcgggaagc     900
```

```
caggcggcga cgtcgagctg atcccgaaaa tccgtctcag ttcggatcgg agtctgcaac    960
ccgactccgt gaagctggat cgctagtaa tcgcgcatca gccatggcgc ggtgaatacg   1020
ttcccgggcc t                                                        1031
```

<210> SEQ ID NO 94
<211> LENGTH: 1010
<212> TYPE: DNA
<213> ORGANISM: uncultured Ureaplasma sp.

<400> SEQUENCE: 94

```
tagggaattt tcacaatgg gcgcaagcct tatgaagcaa tgccgcgtga acgatgaagg    60
tcttatagat tgtaaagttc ttttatatgg gaagaaacgc taaaatagga aatgatttta   120
gtttgactgt accatttgaa taagtatcgg ctaactatgt gccagcagcc gcggtaatac   180
ataggatgca agcgttatcc ggatttactg ggcgtaaaac gagcgcaggc gggtttgtaa   240
gtttggtatt aaatctagat gcttaacgtc tagctgtatc aaaaactgta aacctagagt   300
gtagtaggga gttggggaac tccatgtgga gcggtaaaat gcgtagatat atggaagaac   360
accggtggcg aaggcgccaa cttggactat cactgacgct taggctcgaa agtgtgggga   420
gcaaatagga ttagataccc tagtagtcca caccgtaaac gatcatcatt aaatgtcggc   480
ccgaatgggt cggtgttgta gctaacgcat taaatgatgt gcctgggtag tacattcgca   540
agaatgaaac tcaaacggaa ttgacgggga cccgcacaag tggtggagca tgttgcttaa   600
tttgacaata cacgtagaac cttacctagg tttgacatct attgcgatgc tatagaaata   660
tagttgaggt taacaatatg acaggtggtg catggttgtc gtcagctcgt gtcgtgagat   720
gttgggttaa gtcccgcaac gagcgcaacc cctttcgtta gttactttc tagcgatact   780
gctaccgcaa ggtagaggaa ggtggggatg acgtcaaatc atcatgcccc ttatatctag   840
ggctgcaaac gtgctacaat ggctaataca aactgctgca aaatcgtaag atgaagcgaa   900
acagaaaaag ttagtctcag ttcggataga gggctgcaat tcgtcctctt gaagttggaa   960
tcactagtaa tcgcgaatca gacatgtcgc ggtgaatacg ttctcgggtc                1010
```

<210> SEQ ID NO 95
<211> LENGTH: 1018
<212> TYPE: DNA
<213> ORGANISM: uncultured Staphylococcus sp.

<400> SEQUENCE: 95

```
tgggcgaaag cctgacggag caacgccgcg tgagtgatga aggtcttcgg atcgtaaaac    60
tctgttatta gggaagaaca aatgtgtaag taactatgca cgtcttgacg gtacctaatc   120
agaaagccac ggctaactac gtgccagcag ccgcggtaat acgtaggtgg caagcgttat   180
ccggaattat tgggcgtaaa gcgcgcgtag gcggtttttt aagtctgatg tgaaagccca   240
cggctcaacc gtggagggtc attggaaact ggaaaacttg agtgcagaag aggaaagtgg   300
aattccatgt gtagcggtga aatgcgcaga gatatggagg aacaccagtg gcgaaggcga   360
ctttctggtc tgtaactgac gctgatgtgc gaaagcgtgg ggatcaaaca ggattagata   420
ccctggtagt ccacgccgta aacgatgagt gctaagtgtt agggggtttc cgccccttag   480
tgctgcagct aacgcattaa gcactccgcc tggggagtac gaccgcaagg ttgaaactca   540
aaggaattga cggggacccg cacaagcggt ggagcatgtg gtttaattcg aagcaacgcg   600
aagaacctta ccaaatcttg acatcctctg acccctctag agatagagtt ttcccccttcg   660
ggggacagag tgacaggtgg tgcatggttg tcgtcagctc gtgtcgtgag atgttgggtt   720
```

| | |
|---|---|
| aagtcccgca acgagcgcaa cccttaagct tagttgccat cattaagttg ggcactctaa | 780 |
| gttgactgcc ggtgacaaac cggaggaagg tggggatgac gtcaaatcat catgccccTT | 840 |
| atgatttggg ctacacacgt gctacaatgg acaatacaaa gggtagcgaa accgcgaggt | 900 |
| caagcaaatc ccataaagtt gttctcagtt cggattgtag tctgcaactc gactatatga | 960 |
| agctggaatc gctagtaatc gtagatcagc atgctacggt gaatacgttc ccgggtct | 1018 |

<210> SEQ ID NO 96
<211> LENGTH: 989
<212> TYPE: DNA
<213> ORGANISM: uncultured Clostridium sp.

<400> SEQUENCE: 96

| | |
|---|---|
| tgggggaaac cctgatgcag caacgccgcg tgagtgatga cggtcttcgg attgtaaagc | 60 |
| tctgtctttg gggacgataa tgacggtacc caaggaggaa gccacggcta actacgtgcc | 120 |
| agcagccgcg gtaatacgta ggtggcgagc gttatccgga attattgggc gtaaagggag | 180 |
| cgtaggcgga taattaagtg ggatgtgaaa tactcaggct caacctgggg gctgcattcc | 240 |
| aaactgatta tctagagtgc aggagaggag agtggaattc ctagtgtagc ggtgaaatgc | 300 |
| gtagagatta ggaagaacac cagtggcgaa ggcgactctc tggactgtaa ctgacgctga | 360 |
| ggctcgaaag cgtggggagc aaacaggatt agataccctg gtagtccacg ccgtaaacga | 420 |
| tgaatactag gtgtgggggt ttcaacacct ccgtgccgcc gctaacgcat taagtattcc | 480 |
| gcctggggag tacggtcgca agattaaaac tcaaaggaat tgacggggac ccgcacaagc | 540 |
| agcggagcat gtggtttaat tcgaagcaac gcgaagaacc ttacctacac ttgacatccc | 600 |
| ttgcattacc cttaatcggg gaaatctctt cggagacaag gtgacaggtg gtgcatggtt | 660 |
| gtcgtcagct cgtgtcgtga gatgttgggt taagtcccgc aacgagcgca ccccTATTG | 720 |
| ttagttgcta ccattaagtt gagcactcta gcgagactgc ctgggttaac taggaggaag | 780 |
| gtggggatga cgtcaaatca tcatgcccct tatgtgtagg gctacacacg tgctacaatg | 840 |
| gcaagtacag agagacgcaa aaccgtgagg tcgagcaaat cccttaaaac ttgtcccagt | 900 |
| tcggattgta ggctgaaact cgcctacatg aagccggagt tgctagtaat cgcgaatcag | 960 |
| aatgtcgcgg tgaatacgtt cccgggtct | 989 |

<210> SEQ ID NO 97
<211> LENGTH: 1036
<212> TYPE: DNA
<213> ORGANISM: uncultured Veillonella sp.

<400> SEQUENCE: 97

| | |
|---|---|
| tggggaatct tccgcaatgg acgaaagtct gacggagcaa cgccgcgtga gtgatgacgg | 60 |
| tcttcggatt gtaaagctct gttaatcggg acgaatggtt tgtgtgcaaa tagtgcatag | 120 |
| acatgacggt accggaatag aaagccacgg ctaactacgt gccagcagcc gcggtaatac | 180 |
| gtaggtggca agcgttgtcc ggaattattg ggcgtaaagc gcgcgcaggc ggactagcca | 240 |
| gtcagtctta aaagttcggg gcttaacccc gtgatgggat tgaaactact agtctagagt | 300 |
| atcggagagg aaagtggaat tcctagtgta gcggtgaaat gcgtagatat taggaagaac | 360 |
| accagtggcg aaggcgactt tctggacgaa cactgacgct gaggcgcgaa agccagggga | 420 |
| gcgaacggga ttagatiaccc cggtagtcct ggccgtaaac gatgggtact aagtgtggga | 480 |
| ggtatcgacc ccttccgtgc tgcagttaac gcaataagta ccccgcctgg ggagtacggt | 540 |

```
cgcaagactg aaactcaaag gaattgacgg gggcccgcac aagcggtgga gtatgtggtt    600
taattcgacg caacgcgaag aaccttacca ggtcttgaca ttgatggaca gaactagaga    660 tagttttct  tcttcggaag ccagaaaaca ggtggtgcac ggttgtcgtc agctcgtgtc    720
gtgagatgtt gggttaagtc ccgcaacgag cgcaacccct atcttatgtt gccagcacgt    780
aatggtggga actcatgaga gactgccgca gacaatgcgg aggaaggcgg ggatgacgtc    840
aaatcatcat gccccttatg acctgggcta cacacgtact acaatgggag ttaataaaga    900
gaagcgaaac cgcgaggtgg agcgaacctc acaaacactc tctcagttcg gattgcaggc    960
tgcaactcgc ctgcatgaag tcggaatcgc tagtaatcgc aggtcagcat actgcggtga    1020
atacgttccc gggcct                                                    1036

<210> SEQ ID NO 98
<211> LENGTH: 1025
<212> TYPE: DNA
<213> ORGANISM: uncultured bacterium

<400> SEQUENCE: 98
tgaggaatat tggtcaatgg gcgggagcct gaaccagcca agtagcgtgc aggaagacgg     60
ccctatgggt tgtaaactgc ttttatgcgg ggataaagga gtccacgtgt gggcttttgc    120
aggtaccgca tgaataagga ccggctaatt ccgtgccagc agccgcggta atacggaagg    180
tccgggcgtt atccggattt attgggttta aagggagcgt aggccgcgtt ttaagcgtgt    240
tgtgaaatgt aggcgcccaa cgtctgcatc gcagcgcgaa ctggaacgct gagtacgcg     300 caacgttggc ggaattcgtc gtgtagcggt gaaatgctta gatatgacga agaactccga    360
ttgcgaaggc agctgacggg agcggcactg acgcttaagc tcgaaggtgc gggtatcaaa    420
caggattaga taccctggta gtccgcacgg taaacgatgg atgctcgctg tgtgccttt     480 gtggtacgcg gctaagcgaa agcgttaagc atcccacctg gggagtacgc cggcaacggt    540
gaaactcaaa ggaattgacg ggggcccgca caagcggagg aacatgtggt ttaattcgat    600
gatacgcgag gaaccttacc cgggcttgaa ctgccggcga acgatccaga gatggtgagg    660
cccctcgggg cgccggtgga ggtgctgcat ggttgtcgtc agctcgtgcc gtgaggtgtc    720
ggcttaagtg ccataacgag cgcaaccccct ctccgtagtt gccatcaggt agtgctgggc    780
actctgcgga cactgccacc gcaaggtgcg aggaaggtgg ggatgacgtc aaatcagcac    840
ggcccttacg tccggggcta cacacgtgtt acaatggggg gcacagcgag tcggccgcgc    900
gcaagctcgg tccaatcaag aaatcccccc tcagttcgga ctggggtctg caacccgacc    960
ccacgaagct ggattcgcta gtaatcgcgc atcagccatg gcgcggtgaa tacgttcccg    1020
ggcct                                                                1025

<210> SEQ ID NO 99
<211> LENGTH: 1007
<212> TYPE: DNA
<213> ORGANISM: uncultured bacterium, bacterial vaginosis-associated
       bacterium 1

<400> SEQUENCE: 99
tggggaatat tgcacaatgg gcgaaagcct gatgcagcga cgccgcgtga gcgaagaagt     60
atttcggtat gtaaagctct atcagaaggg aagaaaatga cggtaccctta ctaagaagct    120 ccggctaaat acgtgccagc agccgcggta atacgtatgg agcaagcgtt atccggattt    180
actgggtgta aagggagtgt aggcggcact ataagtctga tgtgaaaacc taaggcttaa    240
```

```
ccataggatt gcattggaaa ctgtagagct ggagtatcgg agaggcaagc ggaattcctg    300
gtgtagtggt gaaatacgta gatatcagga agaacatcgg tggcgaaggc ggcttgctgg    360
acgataactg acgctaaggc tcgaaagcgt gggaagcgaa caggattaga taccctggta    420
gtccacgctg taaacgatga acactaggtg ttgggaggct aagcctttca gtgccgcagc    480
aaacgcaata agtgttccac ctggggagta cgttcgcaag aatgaaactc aaaggaattg    540
acggggaccc gcacaagcgg tggagcatgt ggtttaattc gaagcaacgc gaagaacctt    600
accaagtctt gacatccctg tgacagtata tgtaatgtat attttctacg aacacagga    660 gacaggtggt gcatggttgt cgtcagctcg tgtcgtgaga tgttgggtta agtcccgcaa    720
cgagcgcaac ccttgtactt agtagccagc attaaggtgg gcactctaag tagactgccg    780
gggtgaaccc ggaggaaggt ggggatgacg tcaaatcatc atgcccctta tgacttgggc    840
tacacacgtg ctacaatggc gtgaacagag ggaagcgaag gagcgatccg gagcaaatct    900
cataaagcac gtcccagttc ggactgcagt ctgcaactcg actgcacgaa gctggaatcg    960
ctagtaatcg cagatcatca tgctgcggtg aatacgttcc cgggtct                 1007
```

<210> SEQ ID NO 100
<211> LENGTH: 1009
<212> TYPE: DNA
<213> ORGANISM: uncultured bacterium, bacterial vaginosis-associated bacterium 2

<400> SEQUENCE: 100

```
tggggaatat tgggcaatgg gcgaaagcct gacccagcaa cgccgcgtga gtgatgaagg    60
ccttcgggtt gtaaaactct ttggacaggg acgaagaaag tgacggtacc tgtagaacaa    120
gccacggcta actacgtgcc agcagccgcg gtaatacgta ggtggcgagc gttatccgga    180
tttactgggc gtaaagggcg tgtaggcggc tagataagtg tgatgtttaa atccaaggct    240
taaccttggg gttcattaca aactgtttag cttgagtgct ggagaggata gtggaattcc    300
tagtgtagcg gtaaatgcg tagatattag gaggaacacc ggtggcgaag gcggctatct    360
ggacagtaac tgacgctgag gcgcgaaagc gtggggagca acaggattag ataccctggg    420
tagtccacgc cgtaaacgat gaatactagc tgtaggaggt atcgacccct tctgtggcgc    480
agttaacaca ataagtattc cgcctgggga gtacggccgc aaggttaaaa ctcaaaggaa    540
ttgacgggga cccgcacaag cagtggatta tgtggtttaa ttcgaagcaa cgcgaagaac    600
cttaccagga cttgacatcc tctgacgatt caggagactg aattttctct tcggagacag    660
agagacaggt ggtgcatggt tgtcgtcagc tcgtgtcgtg agatgttggg ttaagtcccg    720
caacgagcgc aacccctatt gattgttgct aacagtaaga tgagcactca attgagactg    780
ccgttgataa aacggaggaa ggtggggacg acgtcaaatc atcatgcccc ttatgttctg    840
ggctacacac gtaatacaat ggctgtgaca gagggaagca agagggcgac cttaagcgaa    900
tcccaaaacg cagtctcagt tcggattgca ggctgcaact cgcctgcatg aagtcggaat    960
tgctagtaat ggcaggtcag catactgccg tgaatacgtt cccgggtct               1009
```

<210> SEQ ID NO 101
<211> LENGTH: 1010
<212> TYPE: DNA
<213> ORGANISM: uncultured bacterium, bacterial vaginosis-associated bacterium 3

<400> SEQUENCE: 101

```
tggggaatat tgggcaatgg gcgaaagcct gacccagcaa cgccgcgtga agtatgaagg    60
```

```
ccttcgggtt gtaaacttct ttgatcaggg aagaaacaaa tgacggtacc tgaaaaacaa      120
gccacggcta actacgtgcc agcagccgcg gtaatacgta ggtggcgagc gttatccgga      180
tttactgggt gtaaagggcg tgcaggcggg ctgataagtc agatgtgaaa tccccgagct      240
taactcggga actgcatctg atactgttgg tcttgagtgc tggagaggat agtggaattc      300
ctagtgtagc ggtaaaatgc gcagatatta ggaggaacac cagtggcgaa ggcggctatc      360
tggacagtaa ctgacgctga ggcgcgaaag cgtgggtagc aaacaggatt agataccctg      420
gtagtccacg ccgtaaacga tgattactag gtgtaggagg tatcgacccc ttctgtgccg      480
gagttaacac aataagtaat ccacctgggg agtacggccg caaggttgaa actcaaagga      540
attgacgggg gcccgcacaa gcagtggagt atgtggttta attcgacgca acgcgaagaa      600
ccttaccagg gtttgacatc ccttgaacga tgtagagata cataattccc ttcggggaca      660
aggagacagg tggtgcatgg ttgtcgtcag ctcgtgtcgt gagatgttgg gttaagtccc      720
gcaacgagcg caacccctat tgccagttgc catcatttag ttgggcactc aggcgagact      780
gccgttgata aaacggagga aggtggggat gacgtcaaat catcatgccc cttatatcct      840
gggctacaca cgtactacaa tggctacaac agagagcagc gacgtcgcga ggcgaagcaa      900
atccccaaat gtagtctcag ttcggattgc aggctgcaac tcgcctgcat gaagccggaa      960
ttgctagtaa tggcaggtca gcatactgcc gtgaatacgt tctcgggcct                1010
```

<210> SEQ ID NO 102
<211> LENGTH: 1009
<212> TYPE: DNA
<213> ORGANISM: uncultured Leptotrichia sp.

<400> SEQUENCE: 102

```
tggggaatat tggacaatgg agggaactct gatccagcaa ttctgtgtgt gtgaagaagg       60
ttttaggact gtaaaacact tttagtaggg aagaaaaaaa tgacggtacc tacagaagaa      120
gcaacggcta aatacgtgcc agcagccgcg gtaatacgta tgttgcgagc gttatccgga      180
attattgggc ttaaagggca tctaggcggt aagacaagtt gaaggtgaaa acctgtggct      240
caaccatagg cttgcctaca aaactgttga actagagtac tggaaaggtg gtggaacta      300
cacgagtaga ggtgaaattc gtagatatgt gtaggaatgc cgatgatgaa gataactcac      360
tggacagaaa ctgacgctga agtgcgaaag ctaggggagc aaacaggatt agataccctg      420
gtagtcctag ctgtaaacga tgatcactgg gtgtggggat gcgaagtctc tgtgccgaag      480
caaaagcgat aagtgatccg cctggggagt acgttcgcaa gaatgaaact caaaggaatt      540
gacggggcc cgcacaagtg gtggagcatg tggtttaatt cgacgcaacg cgaggaacct      600
taccagatct tgacatcctc gggagagtat agaagtatac ttgtgccttc gggaaccgag      660
agacaggtgg tgcatggctg tcgacagctc gtgttgtgag atgttgggtt aagtcccgca      720
acgagcgaaa cccctatcat tagttgccat cattaagttg gggactctaa tgaaactgcc      780
tacgaagagt aggaggaagg tggggatgac gtcaagtcat catgcccctt atgatctggg      840
ctacacacgt gctacaatgg gtagtacaaa gagaagcttt gtagcgatac atggcgaaac      900
ttaaaaagct attcttagtt cggattgaag tctgcaactc gacttcatga agttggaatc      960
actagtaatc gtgaatcagc aatgtcacgg tgaatacgtt ctcgggcct                 1009
```

<210> SEQ ID NO 103
<211> LENGTH: 1007
<212> TYPE: DNA

<213> ORGANISM: Bacterial vaginosis associated bacterium 1

<400> SEQUENCE: 103

```
tggggaatat tgcacaatgg gcgaaagcct gatgcagcga cgccgcgtga gcgaagaagt    60
atttcggtat gtaaagctct atcagaaggg aagaaaatga cggtacctta ctaagaagct   120
ccggctaaat acgtgccagc agccgcggta atacgtatgg agcaagcgtt atccggattt   180
actgggtgta aagggagtgt aggcggcact ataagtctga tgtgaaaacc taaggcttaa   240
ccataggatt gcattggaaa ctgtagagct ggagtatcgg agaggcaagc ggaattcctg   300
gtgtagtggt gaaatacgta gatatcagga agaacatcgg tggcgaaggc ggcttgctgg   360
acgataactg acgctaaggc tcgaaagcgt gggaagcgaa caggattaga taccctggta   420
gtccacgctg taaacgatga acactaggtg ttgggaggct aagcctttca gtgccgcagc   480
aaacgcaata agtgttccac ctggggagta cgttcgcaag aatgaaactc aaaggaattg   540
acggggaccc gcacaagcgg tggagcatgt ggtttaattc gaagcaacgc gaagaacctt   600
accaagtctt gacatccctg tgacagtata tgtaatgtat attttctacg aacacagga    660
gacaggtggt gcatggttgt cgtcagctcg tgtcgtgaga tgttgggtta agtcccgcaa   720
cgagcgcaac ccttgtactt agtagccagc attaaggtgg gcactctaag tagactgccg   780
gggtgaaccc ggaggaaggt ggggatgacg tcaaatcatc atgccccta tgacttgggc    840
tacacacgtg ctacaatggc gtgaacagag ggaagcgaag gagcgatccg gagcaaatct   900
cataaagcac gtcccagttc ggactgcagt ctgcaactcg actgcacgaa gctggaatcg   960
ctagtaatcg cagatcatca tgctgcggtg aatacgttcc cgggtct                1007
```

<210> SEQ ID NO 104
<211> LENGTH: 1009
<212> TYPE: DNA
<213> ORGANISM: Bacterial vaginosis associated bacterium 2

<400> SEQUENCE: 104

```
tggggaatat tgggcaatgg gcgaaagcct gacccagcaa cgccgcgtga gtgatgaagg    60
ccttcgggtt gtaaaactct ttggacaggg acgaagaaag tgacggtacc tgtagaacaa   120
gccacggcta actacgtgcc agcagccgcg gtaatacgta ggtggcgagc gttatccgga   180
tttactgggc gtaaagggcg tgtaggcggc tagataagtg tgatgtttaa atccaaggct   240
taaccttggg gttcattaca aactgtttag cttgagtgct ggagaggata gtggaattcc   300
tagtgtagcg gtaaaatgcg tagatattag gaggaacacc ggtggcgaag gcggctatct   360
ggacagtaac tgacgctgag gcgcgaaagc gtggggagca acaggatta gataccctgg   420
tagtccacgc cgtaaacgat gaatactagc tgtaggaggt atcgacccct tctgtggcgc   480
agttaacaca ataagtattc cgcctgggga gtacggccgc aaggttaaaa ctcaaaggaa   540
ttgacgggga cccgcacaag cagtggatta tgtggtttaa ttcgaagcaa cgcgaagaac   600
cttaccagga cttgacatcc tctgacgatt caggagactg aattttctct cggagacag    660
agagacaggt ggtgcatggt tgtcgtcagc tcgtgtcgtg agatgttggg ttaagtcccg   720
caacgagcgc aaccccctatt gattgttgct aacagtaaga tgagcactca attgagactg   780
ccgttgataa aacggaggaa ggtggggacg acgtcaaatc atcatgcccc ttatgttctg    840
ggctacacac gtaatacaat ggctgtgaca gagggaagca agagggcgac cttaagcgaa   900
tcccaaaacg cagtctcagt tcggattgca ggctgcaact cgcctgcatg aagtcggaat   960
tgctagtaat ggcaggtcag catactgccg tgaatacgtt cccgggtct               1009
```

<210> SEQ ID NO 105
<211> LENGTH: 1010
<212> TYPE: DNA
<213> ORGANISM: Bacterial vaginosis associated bacterium 3

<400> SEQUENCE: 105

| | | | | | |
|---|---|---|---|---|---|
| tggggaatat | tgggcaatgg | gcgaaagcct | gacccagcaa | cgccgcgtga | agtatgaagg | 60 |
| ccttcgggtt | gtaaacttct | tgatcaggg | aagaaacaaa | tgacggtacc | tgaaaaacaa | 120 |
| gccacggcta | actacgtgcc | agcagccgcg | gtaatacgta | ggtggcgagc | gttatccgga | 180 |
| tttactgggt | gtaaagggcg | tgcaggcggg | ctgataagtc | agatgtgaaa | tccccgagct | 240 |
| taactcggga | actgcatctg | atactgttgg | tcttgagtgc | tggagaggat | agtggaattc | 300 |
| ctagtgtagc | ggtaaaatgc | gcagatatta | ggaggaacac | cagtggcgaa | ggcggctatc | 360 |
| tggacagtaa | ctgacgctga | ggcgcgaaag | cgtgggtagc | aaacaggatt | agataccctg | 420 |
| gtagtccacg | ccgtaaacga | tgattactag | gtgtaggagg | tatcgacccc | ttctgtgccg | 480 |
| gagttaacac | aataagtaat | ccacctgggg | agtacggccg | caaggttgaa | actcaaagga | 540 |
| attgacgggg | gcccgcacaa | gcagtggagt | atgtggttta | attcgacgca | acgcgaagaa | 600 |
| ccttaccagg | gtttgacatc | ccttgaacga | tgtagagata | cataattccc | ttcggggaca | 660 |
| aggagacagg | tggtgcatgg | ttgtcgtcag | ctcgtgtcgt | gagatgttgg | gttaagtccc | 720 |
| gcaacgagcg | caaccctat | tgccagttgc | catcatttag | ttgggcactc | aggcgagact | 780 |
| gccgttgata | aaacggagga | aggtggggat | gacgtcaaat | catcatgccc | cttatatcct | 840 |
| gggctacaca | cgtactacaa | tggctacaac | agagagcagc | gacgtcgcga | ggcgaagcaa | 900 |
| atccccaaat | gtagtctcag | ttcggattgc | aggctgcaac | tcgcctgcat | gaagccggaa | 960 |
| ttgctagtaa | tggcaggtca | gcatactgcc | gtgaatacgt | tctcgggcct | | 1010 |

<210> SEQ ID NO 106
<211> LENGTH: 21
<212> TYPE: DNA
<213> ORGANISM: Artificial
<220> FEATURE:
<223> OTHER INFORMATION: PCR primer

<400> SEQUENCE: 106
gatgccaaca gtatccgtcc g                                         21

<210> SEQ ID NO 107
<211> LENGTH: 22
<212> TYPE: DNA
<213> ORGANISM: Artificial
<220> FEATURE:
<223> OTHER INFORMATION: PCR primer

<400> SEQUENCE: 107
cctctccgac actcaagttc ga                                        22

<210> SEQ ID NO 108
<211> LENGTH: 22
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' VIC label
<220> FEATURE:

```
<221> NAME/KEY: misc_feature
<222> LOCATION: (22)..(22)
<223> OTHER INFORMATION: 3' TAMRA label

<400> SEQUENCE: 108
gtaccgtaag agaaagccac gg                                              22

<210> SEQ ID NO 109
<211> LENGTH: 18
<212> TYPE: DNA
<213> ORGANISM: Artificial
<220> FEATURE:
<223> OTHER INFORMATION: PCR primer

<400> SEQUENCE: 109
ggagtgtagg cggcacta                                                   18

<210> SEQ ID NO 110
<211> LENGTH: 21
<212> TYPE: DNA
<213> ORGANISM: Artificial
<220> FEATURE:
<223> OTHER INFORMATION: PCR Primer

<400> SEQUENCE: 110
tagagctgga gtatcggaga g                                               21

<210> SEQ ID NO 111
<211> LENGTH: 28
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM label

<400> SEQUENCE: 111
acctaaggct taaccatagg attgcatt                                        28

<210> SEQ ID NO 112
<211> LENGTH: 22
<212> TYPE: DNA
<213> ORGANISM: Artificial
<220> FEATURE:
<223> OTHER INFORMATION: PCR primer

<400> SEQUENCE: 112
ttaaccttgg ggttcattac aa                                              22

<210> SEQ ID NO 113
<211> LENGTH: 24
<212> TYPE: DNA
<213> ORGANISM: Artificial
<220> FEATURE:
<223> OTHER INFORMATION: PCR primer

<400> SEQUENCE: 113
gaatacttat tgtgttaact gcgc                                            24

<210> SEQ ID NO 114
<211> LENGTH: 23
<212> TYPE: DNA
<213> ORGANISM: Artificial
<220> FEATURE:
<223> OTHER INFORMATION: Oligonucleotide probe
```

```
<220> FEATURE:
<221> NAME/KEY: misc_feature
<222> LOCATION: (1)..(1)
<223> OTHER INFORMATION: 5' FAM label
<220> FEATURE:
<221> NAME/KEY: misc_feature
<222> LOCATION: (23)..(23)
<223> OTHER INFORMATION: 3' TAMRA label

<400> SEQUENCE: 114
tctccagcac tcaagctaaa cag                                              23

<210> SEQ ID NO 115
<211> LENGTH: 23
<212> TYPE: DNA
<213> ORGANISM: Artificial
<220> FEATURE:
<223> OTHER INFORMATION: PCR primer

<400> SEQUENCE: 115
gcggctagat aagtgtgatg ttt                                              23

<210> SEQ ID NO 116
<211> LENGTH: 21
<212> TYPE: DNA
<213> ORGANISM: Artificial
<220> FEATURE:
<223> OTHER INFORMATION: PCR primer

<400> SEQUENCE: 116
tttagcttga gtgctggaga g                                                21

<210> SEQ ID NO 117
<211> LENGTH: 28
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM label

<400> SEQUENCE: 117
caaggcttaa ccttggggtt cattacaa                                         28

<210> SEQ ID NO 118
<211> LENGTH: 21
<212> TYPE: DNA
<213> ORGANISM: Artificial
<220> FEATURE:
<223> OTHER INFORMATION: PCR primer

<400> SEQUENCE: 118
catttagttg ggcactcagg c                                                21

<210> SEQ ID NO 119
<211> LENGTH: 22
<212> TYPE: DNA
<213> ORGANISM: Artificial
<220> FEATURE:
<223> OTHER INFORMATION: PCR primer

<400> SEQUENCE: 119
ggcgaagcaa atccccaaat gt                                               22

<210> SEQ ID NO 120
```

```
<211> LENGTH: 25
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (25)..(25)
<223> OTHER INFORMATION: 3' TAMRA label

<400> SEQUENCE: 120
tactacaatg gctacaacag agagc                                          25

<210> SEQ ID NO 121
<211> LENGTH: 21
<212> TYPE: DNA
<213> ORGANISM: Artificial
<220> FEATURE:
<223> OTHER INFORMATION: PCR primer

<400> SEQUENCE: 121
acctgggctt gacatgtgcc t                                              21

<210> SEQ ID NO 122
<211> LENGTH: 21
<212> TYPE: DNA
<213> ORGANISM: Artificial
<220> FEATURE:
<223> OTHER INFORMATION: PCR primer

<400> SEQUENCE: 122
caggttcaca ggtggtgcat g                                              21

<210> SEQ ID NO 123
<211> LENGTH: 24
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM label
<220> FEATURE:
<221> NAME/KEY: misc_feature
<222> LOCATION: (24)..(24)
<223> OTHER INFORMATION: 3' TAMRA label

<400> SEQUENCE: 123
ctgcagagat gtggtttccy ttcg                                           24

<210> SEQ ID NO 124
<211> LENGTH: 23
<212> TYPE: DNA
<213> ORGANISM: Artificial
<220> FEATURE:
<223> OTHER INFORMATION: PCR primer

<400> SEQUENCE: 124
aattattggg cttaaagggc atc                                            23

<210> SEQ ID NO 125
<211> LENGTH: 25
<212> TYPE: DNA
<213> ORGANISM: Artificial
<220> FEATURE:
<223> OTHER INFORMATION: PCR primer

<400> SEQUENCE: 125
```

```
ctacaaaact gttgaactag agtac                                           25
```

<210> SEQ ID NO 126
<211> LENGTH: 26
<212> TYPE: DNA
<213> ORGANISM: Artificial
<220> FEATURE:
<223> OTHER INFORMATION: PCR primer

<400> SEQUENCE: 126

```
ctacaaaact gtataactag agtact                                          26
```

<210> SEQ ID NO 127
<211> LENGTH: 26
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM label
<220> FEATURE:
<221> NAME/KEY: misc_feature
<222> LOCATION: (26)..(26)
<223> OTHER INFORMATION: 3' TAMRA label

<400> SEQUENCE: 127

```
acaagttgaa ggtgaaaacc trtggc                                          26
```

<210> SEQ ID NO 128
<211> LENGTH: 23
<212> TYPE: DNA
<213> ORGANISM: Artificial
<220> FEATURE:
<223> OTHER INFORMATION: PCR primer

<400> SEQUENCE: 128

```
akcattaagt tgggcactct awt                                             23
```

<210> SEQ ID NO 129
<211> LENGTH: 21
<212> TYPE: DNA
<213> ORGANISM: Artificial
<220> FEATURE:
<223> OTHER INFORMATION: PCR primer

<400> SEQUENCE: 129

```
cctgygaagg caagcggatc t                                               21
```

<210> SEQ ID NO 130
<211> LENGTH: 28
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM label
<220> FEATURE:
<221> NAME/KEY: misc_feature
<222> LOCATION: (28)..(28)
<223> OTHER INFORMATION: 3' TAMRA label

<400> SEQUENCE: 130

```
tcgcttctcg ttgtacygyc cattgtag                                        28
```